(12) United States Patent
Buchanan et al.

(10) Patent No.: US 7,763,624 B2
(45) Date of Patent: Jul. 27, 2010

(54) SUBSTITUTED PYRAZOLO[3,4-D]PYRIMIDINES AS ACK-1 AND LCK INHIBITORS

(75) Inventors: John L. Buchanan, Newton, MA (US); William H. Buckner, Kittery, ME (US); Mario G. Cardozo, San Francisco, CA (US); Erin F. DiMauro, Cambridge, MA (US); Jiasheng Fu, Foster City, CA (US); Xiaolin Hao, Foster City, CA (US); Xian Yun Jiao, San Mateo, CA (US); Frank Kayser, San Francisco, CA (US); David J. Kopecky, San Francisco, CA (US); Craig E. Masse, Cambridge, MA (US); Susan A. Tomlinson, Cambridge, MA (US); Ryan White, Somerville, MA (US); Xiaotian Zhu, Newton, MA (US)

(73) Assignee: Amgen Inc., Thousand Oaks, CA (US)

( * ) Notice: Subject to any disclaimer, the term of this patent is extended or adjusted under 35 U.S.C. 154(b) by 50 days.

(21) Appl. No.: 11/506,381

(22) Filed: Aug. 18, 2006

(65) Prior Publication Data

US 2007/0072851 A1 Mar. 29, 2007

Related U.S. Application Data

(60) Provisional application No. 60/710,706, filed on Aug. 22, 2005, provisional application No. 60/715,022, filed on Sep. 7, 2005.

(51) Int. Cl.
| C07D 487/04 | (2006.01) |
| --- | --- |
| A61K 31/519 | (2006.01) |
| A61K 31/496 | (2006.01) |
| A61P 35/00 | (2006.01) |
| C07D 231/56 | (2006.01) |
| A61K 31/416 | (2006.01) |

(52) U.S. Cl. .......... 514/262.1; 544/262; 544/61; 544/118; 514/228.5; 514/234.5; 514/252.16; 514/407; 548/362.1

(58) Field of Classification Search .......... 544/262, 544/61, 118; 514/262.1, 228.5, 234.5, 252.16
See application file for complete search history.

(56) References Cited

U.S. PATENT DOCUMENTS

| 4,163,846 | A | 8/1979 | Percival et al. |
| --- | --- | --- | --- |
| 6,552,026 | B2 | 4/2003 | Pees et al. |
| 6,713,474 | B2 | 3/2004 | Hirst et al. |
| 6,730,680 | B2 | 5/2004 | Pees et al. |
| 6,833,371 | B2 | 12/2004 | Atkinson et al. |
| 2003/0175763 | A1 | 9/2003 | Degenhardt et al. |
| 2003/0176450 | A1 | 9/2003 | Atkinson et al. |
| 2004/0204400 | A1 | 10/2004 | Chern et al. |
| 2006/0106035 | A1 | 5/2006 | Hendrix et al. |
| 2006/0258685 | A1 | 11/2006 | Wagner et al. |

| 2007/0037828 | A1 | 2/2007 | Gebauer et al. |
| --- | --- | --- | --- |

FOREIGN PATENT DOCUMENTS

| EP | 593575 | 5/1997 |
| --- | --- | --- |
| EP | 674642 | 8/2000 |
| JP | 2005008581 | 1/2005 |
| WO | WO 90/03370 | 4/1990 |
| WO | WO 93/01198 | 1/1993 |
| WO | WO 94/13677 | 6/1994 |
| WO | WO 03/037900 | 5/2003 |
| WO | WO2004/018474 | 3/2004 |
| WO | WO 2004/031248 | 4/2004 |
| WO | WO 2004/076450 | 9/2004 |
| WO | WO 2004/076458 | 9/2004 |
| WO | WO 2004/099210 | 11/2004 |
| WO | WO 2004/106341 | 12/2004 |
| WO | WO 2004/113303 | 12/2004 |
| WO | WO 2005/000851 | 1/2005 |
| WO | WO 2005/016528 | 2/2005 |
| WO | WO 2005/021003 | 3/2005 |
| WO | WO 2005/028434 | 3/2005 |

OTHER PUBLICATIONS

Wolff, Manfred E., Burger's Medicinal Chemistry, 5ed, Part I, John Wiley & Sons, 1995, pp. 975-977.*
Banker, G.S. et al, "Modern Pharmaceutics, 3ed.", Marcel Dekker, New York, 1996, p. 596.*
Viggapunta et. al., Advanced Drug Delivery Reviews, 2001, 48, pp. 3-26.*
Abram. C.L. et al. "Src Family Tyrosine Kinases and Growth Factor Signaling," Experimental Cell Research, 254:1-13, 2000.

(Continued)

*Primary Examiner*—Susanna Moore
(74) *Attorney, Agent, or Firm*—Foley & Lardner LLP

(57) ABSTRACT

The present invention relates to compounds of Formula I

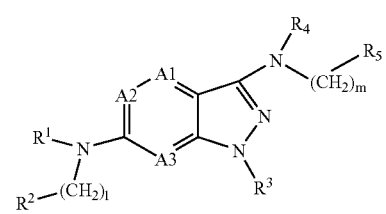

or a stereomer, a tautomer, a solvate, a pharmaceutically acceptable salt, or a prodrug thereof, pharmaceutical formulations containing the compounds, methods of treatments using the compounds, for example, protein tyrosine kinase-associated disorders such as immunologic and oncologic disorders and methods of preparing medicaments comprising the compounds.

34 Claims, No Drawings

OTHER PUBLICATIONS

Altmann, E. et al. "7-Pyrrolidinyl- and 7-Piperidinyl-5-aryl-pyrrolo[2,3-d]- pyrimidines- Potent Inhibitors of the Tyrosine Kinase c-Src." Bioorganic and Medicinal Chemistry Letters, 11:853-856, 2001.

Anderson, S.J. et al. "Involvement of the Protein Tyrosine Kinase p56$^{lck}$ in T Cell Signaling and Thymocyte Development." Advances in Immunology, 56: 151-178, 1994.

Appleby, M.W. et al. "Defective T Cell Receptor Signaling in Mice Lacking the Thymic Isoform of p59$^{fyn}$." Cell, 70:751-763, 1992.

Bolen, J.B. et al. "Leukocyte Protein Tyrosine Kinases: Potential Targets for Drug Discovery." Annual Reviews in Immunology, 15:371-404, 1997.

Burchat, A.F. et al. "Pyrazolo[3,4-d]pyrimidines Containing an Extended 3-Substituent as Potent Inhibitors of Lck—a Selectivity Insight." Bioorganic and Medicinal Chemistry Letters, 12:1687-1690, 2002.

Chen, P. et al. "Synthesis and SAR of Novel Imidazoquinoxaline-Based Lck Inhibitors: Improvement of Cell Potency." Bioorganic and Medicinal Chemistry Letters, 12:3153-3156, 2002.

Goldman, F.D. et al. "Defective Expression of p56Ick in an Infant with Severe Combined Immunodeficiency." Journal of Clinical Investigation, 102(2):421-429, 1998.

Hanke, J.H. et al. "Discovery of a Novel, Potent, and Src Family-selective Tyrosine Kinase Inhibitor." Journal of Biological Chemistry, 271(2):695-701, 1996.

Kane, L.P. et al. "Signal transduction by the TCR for antigen." Current Opinion in Immunology, 12:242-249, 2000.

Manser, E. et al. "A non-receptor tyrosine kinase that inhibits the GTPase activity of p21$^{cdc42}$." Nature, 363(6427):364-367, 1993.

Paul, R. et al. "Src deficiency or blockade of Src activity in mice provides cerebral protection following stroke." Nature Medicine, 7(2):222-227, 2001.

Soriano, P. et al. "Targeted Disruption of the c-*src* Proto-Oncogene Leads to Osteopetrosis in Mice." Cell, 64:693-702, 1991.

Turner, H. et al. "Signalling through the high-affinity IgE receptor FcERI." Nature, 402:B24-B30, 1999.

Vicentini, L. et al. "Fgr Deficiency Results in Defective Eosinophil Recruitment to the Lung During Allergic Airway Inflammation." Journal of Immunology, 168:6446-6454, 2002.

Wang, Y.D. et al. "Inhibitors of Src Tyrosine Kinase: The Preparation and Structure—Activity Relationship of 4-Anilino-3-cyanoquinolines and 4-Anilinoquinazolines." Bioorganic and Medicinal Chemistry Letters, 10: 2477-2480, 2000.

* cited by examiner

SUBSTITUTED PYRAZOLO[3,4-D]PYRIMIDINES AS ACK-1 AND LCK INHIBITORS

CROSS-REFERENCE TO RELATED APPLICATIONS

This application claims the benefit of U.S. Provisional Application Nos. 60/710,706 filed Aug. 22, 2005 and 60/715,022 filed Sep. 7, 2005, which are incorporated herein by reference in their entireties.

FIELD OF THE INVENTION

This invention generally relates to pyrazolopyridine and pyrazolopyrimidine compounds, pharmaceutical formulations containing the compounds, methods of treatment using the compounds, and methods of preparing medicaments comprising the compounds.

BACKGROUND OF THE INVENTION

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of organ transplantation rejection, allergic reactions, and asthma.

T cells are activated by specific antigens through T cell receptors (TCR), which are expressed on the cell surface. This activation triggers a series of intracellular signaling cascades mediated by enzymes expressed within the cell (Kane, L P et al. Current Opinion in Immunol. 2000, 12, 242). These cascades lead to gene regulation events that result in the production of cytokines, including interleukin-2 (IL-2). IL-2 is a critical cytokine in T cell activation, leading to proliferation and amplification of specific immune responses.

Kinase enzymes have been shown to be important in the intracellular signal transduction. One class of kinase enzymes involved in signal transduction is the Src-family of protein tyrosine kinases (PTK's), which includes, for example: Lck, Fyn(B), Fyn(T), Lyn, Src, Yes, Hck, Fgr and Blk (for review see: Bolen, J B and Brugge, J S Annu. Rev. Immunol 1997, 15, 371). Gene disruption studies suggest that inhibition of some members of the Src family of kinases would potentially lead to therapeutic benefit. Src(−/−) mice have abnormalities in bone remodeling or osteopetrosis (Soriano, P. Cell 1991, 64, 693), suggesting that inhibition of the src kinase might be useful in diseases of bone resorption, such as osteoporosis. Lck(−/−) mice have defects in T cell maturation and activation (Anderson, S J et al. Adv. Immunol. 1994, 56, 151), suggesting that inhibition of the Lck kinase might be useful in diseases of T cell mediated inflammation. In addition, human patients have been identified with mutations effecting Lck kinase activity (Goldman, F D et al. J. Clin. Invest. 1998, 102, 421). These patients suffer from a severe combined immunodeficiency disorder (SCID).

Src-family kinases are also important for signaling downstream of other immune cell receptors. Fyn, like Lck, is involved in TCR signaling in T cells (Appleby, M W et al. Cell 1992, 70, 751). Hck and Fgr are involved in Fcγ receptor signaling leading to neutrophil activation (Vicentini, L. et al. J. Immunol. 2002, 168, 6446). Lyn and Src also participate in Fcγ receptor signaling leading to release of histamine and other allergic mediators (Turner, H. and Kinet, J-P Nature 1999, 402, B24). These findings suggest that Src family kinase inhibitors may be useful in treating allergic diseases and asthma.

Src kinases have also been found to be activated in tumors including sarcoma, melanoma, breast, and colon cancers suggesting that Src kinase inhibitors may be useful anti-cancer agents (Abram, C L and Courtneidge, S A Exp. Cell Res. 2000, 254, 1). Src kinase inhibitors have also been reported to be effective in an animal model of cerebral ischemia (R. Paul et al. Nature Medicine 2001, 7, 222), suggesting that Src kinase inhibitors may be effective at limiting brain damage following stroke.

Cancer is the second leading cause of death in the United States (Boring, et al., CA Cancer J. Clin., 43:7, 1993), and features uncontrolled cellular growth, which results either in local invasion of normal tissue or systemic spread (metastasis) of the abnormal growth. Cancer is caused by inherited or acquired mutations in cancer genes, which have normal cellular functions and which induce or otherwise contribute to cancer once mutated or expressed at an abnormal level. Certain well-studied tumors carry several different independently mutated genes, including activated oncogenes and inactivated tumor suppressor genes. Each of these mutations appears to be responsible for imparting some of the traits that, in aggregate, represent the full neoplastic phenotype (Land et al., Science, 222:771, 1983; Ruley, Nature, 4:602, 1983; Hunter, Cell, 64:249, 1991).

One such trait is gene amplification. Gene amplification involves a chromosomal region bearing specific genes undergoing a relative increase in DNA copy number, thereby increasing the copies of any genes that are present. In general, gene amplification results in increased levels of transcription and translation, producing higher amounts of the corresponding gene mRNA and protein. Amplification of genes causes deleterious effects, which contribute to cancer formation and proliferation (Lengauer et al. Nature, 396:643-649, 1999). Gene amplification has been established as an important genetic alteration in solid tumors (Knuutila et al., Am. J. Pathol., 152(5):1107-23, 1998; Knuutila et al., Cancer Genet. Cytogenet., 100(1):25-30, 1998).

Another trait of tumor cells is the over-expression or differential expression of whole collections of genes. In precancerous or cancerous cells, and tissues, where both amplification of a gene and over-expression of the gene product occur, then that gene and its product present both a diagnostic target as well as a therapeutic opportunity for intervention. In many cases, the amplified cancer genes encode an enzyme, such as a kinase, and the discovery and characterization of inhibitors of the enzymatic activity of this gene product will be a promising avenue that leads to novel therapeutics for cancer treatment.

ACK1 is a gene that is frequently amplified and over-expressed in primary human tumors (U.S. Patent Publication No. 20030175763). ACK1 kinase activity is regulated in the context of cell attachment and detachment, and certain cancer cells depend on ACK1's kinase activity for adhesion, anchorage independent growth and survival. Down regulation of ACK1 kinase activity or ACK1 expression levels can result in reduced tumor growth in animal models. Accordingly, Ack is a target believed to be useful in the regulation of cancer.

The ACK1 gene encodes an intracellular, non-receptor tyrosine kinase that binds cdc42Hs in its GTP-bound form and inhibits both the intrinsic and GTPase-activating protein (GAP)-stimulated GTPase activity of p21cdc42, a Ras-like protein involved in cell growth (Manser et al., Nature 363 (6427): 364-367, 1993). This binding is mediated by a unique polypeptide of 47 amino acids C-terminal to an SH3 domain. ACK1 gene contains a tyrosine kinase domain and is reported to possess tyrosine kinase activity. The protein may be involved in a regulatory mechanism that sustains the GTP-bound active form of cdc42Hs and which is directly linked to a tyrosine phosphorylation signal transduction pathway.

While various groups have published on inhibitors of Src family kinase or ACK-1, disclosing various chemical compounds, including 2-phenylamino-imidazo[4,5-h]isoquinolin-9-ones (Snow, R J et al. J. Med. Chem. 2002, 45, 3394), pyrazolo [3,4-d]pyrimidines (Burchat, A F et al. Bioorganic and Med. Chem. Letters 2002, 12, 1987 and Hanke, J H et al. J. Biol. Chem. 1996, 271, 695), pyrrolo [2,3-d]pyrimidines (Altmann, E et al. Bioorganic and Med. Chem. Letters 2001, 11, 853), anilinoquinazolines (Wang, Y D et al. Bioorganic and Med. Chem. Letters 2000, 10, 2477), and imidazoquinoxalines (Chen, P. et al. Bioorganic and Med. Chem. Letters 2002, 12, 3153), none of these groups describe the compounds of the present invention, and particularly as modulators of kinase enzymes such as Lck and ACK-1, and useful for the regulation of T-cell mediated immune response, autoimmune disease, organ transplantation, allergies, asthma, cancer and the like.

SUMMARY OF THE INVENTION

The present invention provides compounds of Formula I

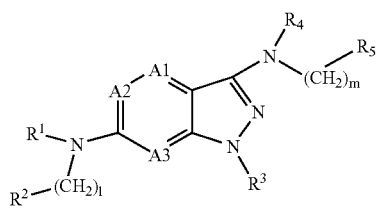

I or a stereomer, a tautomer, a solvate, a pharmaceutically acceptable salt, or a prodrug thereof, wherein $R^1$, $R^2$, $l$, $A^1$, $A^2$, $A^3$, $R^3$, $R^4$, m and $R^5$ are as defined in Detailed Description below.

The instant invention also provides compounds of Formula II

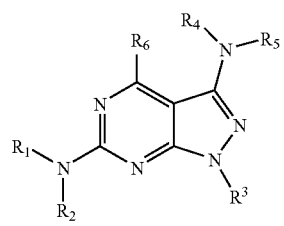

II or a stereomer, a tautomer, a solvate, a pharmaceutically acceptable salt, or a prodrug thereof, wherein $R^1$, $R^2$, $R^3$, $R^4$ and $R^5$ are as defined in Detailed Description below.

In one aspect, the invention provides pharmaceutical composition comprising a pharmaceutically acceptable carrier and compounds of Formulae I and II.

The compounds of Formulae I and II are capable of modulating protein tyrosine kinase enzymes of the Src family, such as Lck, as well as other protein kinase enzymes such as ACK-1. Accordingly, these compounds are useful in the treatment, including preventative, prophylactic and therapeutic treatment, of protein tyrosine kinase-associated disorders, including but not limited to, immunologic and oncologic disorders.

"Protein tyrosine kinase-associated disorders" are disorders which result from aberrant tyrosine kinase activity, and/or which are alleviated by the regulation, and inhibition in particular, of one or more of these kinase enzymes. For example, Lck inhibitors are of value in the treatment of a number of such disorders (for example, the treatment of autoimmune diseases), as Lck inhibition blocks T cell activation. It is believed that the compounds of Formula I modulate T cell activation by way of inhibition of one or more of the multiple protein tyrosine kinases involved in early signal transduction steps leading to T cell activation, for example, by way of inhibition of Lck kinase.

Accordingly, in one aspect of the invention, the compounds of Formula I are useful for the treatment of T cell mediated diseases, including inhibition of T cell activation and proliferation. In another embodiment, the invention provides compounds, which selectively block T cell activation and proliferation. Further, the compounds may block the activation of endothelial cell protein tyrosine kinase by oxidative stress thereby limiting surface expression of adhesion molecules that induce neutrophil binding, and they also can inhibit protein tyrosine kinase necessary for neutrophil activation. The compounds would be useful, therefore, in the treatment of ischemia and reperfusion injury. In another aspect of the invention, methods for the treatment of protein tyrosine kinase-associated disorders are provided. The method comprises administering to a subject at least one compound of Formula I in an amount effective to treat the disorder.

To treat patients for such disorders and conditions, another aspect of the invention provides a composition comprising a compound of Formula I and a pharmaceutically acceptable carrier. Such a composition can be administered to the subject, such as a human, for the purpose of treating the disorder. Other therapeutic agents such as those described below may be employed in combination with the inventive compounds, such as in a combined composition, in the present methods. Alternatively, such other therapeutic agent(s) may be administered prior to, simultaneously with, or following the administration of the compound(s) of the present invention.

With respect to the tyrosine kinase associated disorders, the compound(s) of the present invention may be used in treating related conditions including, without limitation, arthritis (such as rheumatoid arthritis, psoriatic arthritis or osteoarthritis); transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracielma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides methods for treating the aforementioned disorders such as atopic dermatitis by administration of a therapeutically effective amount of a compound of the present invention, which is an inhibitor of protein tyrosine kinase, to a patient suffering from dermatitis and potentially in need of such treatment.

The compounds of the invention are also capable of modulating other kinase enzymes, such as ACK-1. Modulating ACK-1 can be useful for treating various ACK-1-mediated poliferative diseases, such as cancer and cancer-related conditions. Accordingly, this is one route by which the compounds can be useful for treating cancer.

Src-family kinases other than Lck, such as Hck and Fgr, are important in the Fcγ receptor induced respiratory burst of neutrophils as well as the Fcγ receptor responses of monocytes and macrophages. The compounds of the present invention may inhibit the Fcγ induced respiratory burst response in neutrophils, and may also inhibit the Fcγ dependent production of TNFα. The ability to inhibit Fcγ receptor dependent neutrophil, monocyte and macrophage responses would result in additional anti-inflammatory activity for the present compounds in addition to their effects on T cells. This activity would be especially of value, for example, in the treatment of inflammatory diseases, such as arthritis or inflammatory bowel disease. The present compounds may also be of value for the treatment of autoimmune glomerulonephritis and other instances of glomerulonephritis induced by deposition of immune complexes in the kidney that trigger Fcγ receptor responses and which can lead to kidney damage.

In addition, certain Src family kinases, such as Lyn and Fyn(B), may be important in the Fcε receptor induced degranulation of mast cells and basophils that plays an important role in asthma, allergic rhinitis, and other allergic disease. Fcε receptors are stimulated by IgE-antigen complexes. The compounds of the present invention may inhibit the Fcε induced degranulation responses. The ability to inhibit Fcε receptor dependent mast cell and basophil responses may result in additional anti-inflammatory activity for the present compounds beyond their effect on T cells.

The combined activity of the present compounds towards monocytes, macrophages, T cells, etc. may prove to be a valuable tool in the treatment of any of the aforementioned disorders. In yet another aspect of the invention, the compounds are useful for the treatment of the aforementioned exemplary disorders irrespective of their etiology, whether or not associated with PTK.

The foregoing merely summarizes certain aspects of the invention and is not intended, nor should it be construed, as limiting the invention in any way.

DETAILED DESCRIPTION OF THE INVENTION

I. Summary

The invention is directed to compounds of Formula I

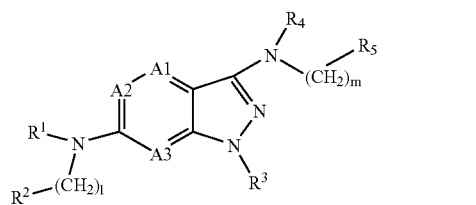

or a stereomer, a tautomer, a solvate, a pharmaceutically acceptable salt, or a prodrug thereof, pharmaceutical formulations containing the compounds, methods of treatments using the compounds, for example, protein tyrosine kinase-associated disorders such as immunologic and oncologic disorders and methods of preparing medicaments comprising the compounds.

II. Definitions

Unless otherwise specified, the following terms found in the specification and claims have the following meanings and/or definitions.

| | |
|---|---|
| ACK1: | Activated p21cdc42Hs associated kinase |
| aq: | Aqueous |
| ATP: | Adenosine triphosphate |
| BSA: | Bovine Serum Albumin |
| DBU: | 1,8-diazabicyclo [5.4.0] undec-7-ene |
| DCE: | Dichloroethane |
| DCM: | Dichloromethane |
| DIEA: | Diisopropylethylamine |
| DMA: | N,N-Dimethylacetamide |
| DME: | Dimethoxyethane |
| DMF: | N,N-Dimethylformamide |
| DMSO: | Dimethylsulfoxide |
| dppf: | 1,1'(diphenylphosphino)ferrocene |
| DTT: | Dithiothreitol |
| EDTA: | Ethylene diamine tetraacetic acid |
| EtOAc: | Ethyl acetate |
| EtOH: | Ethanol |
| FCS: | Fetal Calf Serum |
| g: | Gram(s) |
| h: | Hour(s) |
| HBTU: | O-Benzotriazol-1-yl-N,N,N',N'-tetramethyluronium hexafluorophosphate |
| Hepes: | N-[2-Hydroxyethyl]piperazine-N'-[2-ethanesulfonic acid] |
| IC$_{50}$ value: | The concentration of an inhibitor that causes a 50% reduction in a measured activity. |
| IPA | isopropyl alcohol |
| Lck | Lymphocyte specific tyrosine kinase |
| LiHMDS: | Lithium bis(trimethylsilyl)amide |
| MeI: | Methyl iodide |
| MeCN: | Acetonitrile |
| MeOH: | Methanol |
| min: | Minute(s) |
| mmol: | Millimole(s) |
| NBS: | N-Bromo succinimide |
| Ni-NTA: | Nickel-nitriloacetic acid |
| NIS: | N-Iodosuccinimide |
| NMP: | N-methylpyrrolidone |
| rt: | Room temperature |
| TFA: | Trifluoroacetic acid |
| THF: | Tetrahydrofuran |

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the invention. Procedures for inserting such labels into the compounds of the invention will be readily apparent to those skilled in the art based on the disclosure herein.

In general, "substituted" as used herein refers to a group, such as those defined below, in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfoxide groups, sulfone groups, and sulfonyl groups such as sulfonyl halides and sulfonamides; a nitrogen atom in groups such as amines, amides, alkylamines, dialkylamines, arylamines, alkylarylamines, diarylamines, N-oxides, ureas, imines, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carboxylic acid, ester and carbamate groups; and nitrogen in groups such as imines, oximes, hydrazones, and nitriles.

Substituents, including alkyl and ring groups, may be either monovalent or polyvalent depending on the context of their usage. For example, if description contained the group $R^1$-$R^2$-$R^3$ and $R^2$ was defined as $C_{1-6}$alkyl, then the $R^2$ alkyl would be considered polyvalent because it must be bonded to at least $R^1$ and $R^3$. Alternatively, if $R^1$ was defined as $C_{1-6}$alkyl, then the $R^1$ alkyl would be monovalent (excepting any further substitution language).

In general, "unsubstituted" as used herein with reference to a group, means that the group does not have one or more bonds to a hydrogen or carbon atom contained therein replaced by a bond to non-hydrogen or non-carbon atom, as described above.

In general, "alkyl" as used herein either alone or within other terms such as "haloalkyl", "alkylamino" and "cycloalkyl", refers to linear, branched or cyclic radicals having one to about twelve carbon atoms. "Cycloalkyl" is also used exclusively herein to refer specifically to fully or partially saturated cyclic alkyl radicals. Examples of "alkyl" radicals include methyl, ethyl, n-propyl, isopropyl, n-butyl, isobutyl, sec-butyl, tert-butyl, pentyl, isoamyl, hexyl, cyclopropyl, cyclopentyl, cyclohexyl and the like.

In general, "$C_{a-b}$alkyl" as used herein refers to an alkyl group comprising from a to b carbon atoms in a branched, cyclical or linear relationship or any combination of the three. The alkyl groups described in this section may also contain double or triple bonds. Examples of $C_{1-8}$alkyl include, but are not limited to the following:

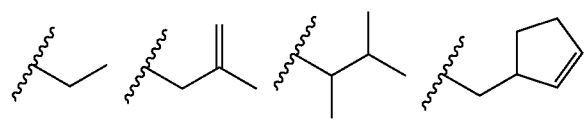

In general, "aralkyl" as used herein refers to linear or branched aryl-containing radicals each having alkyl portions of one to about ten carbon atoms. Examples of such radicals include benzyl, 2-phenyl-propane, and the like.

In general, "halogen" and "halo" as used herein, refers to a halogen atoms selected from F, Cl, Br and I.

In general, "haloalkyl", as used herein refers to radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

In general, "$C_{a-b}$haloalkyl" as used herein refers to an alkyl group, as described above, wherein any number—at least one—of the hydrogen atoms attached to the alkyl chain are replaced by F, Cl, Br or I. Examples of haloalkyl includes, without limitation, trifluoromethyl, pentafluoroethyl and the like.

In general, "heteroalkyl" as used herein refers to an alkyl having one or more of the carbon atoms replaced by a heteroatom, selected from nitrogen, oxygen and sulfur. For example, a heteroalkyl would include an ether or a thioether chain, or an alkoxide moiety, wherein the heteroatom is in the linear region of the moeity. The term also includes moieties where the heteroatom is in a branched region. For example, the term includes 2-amino-n-hexane or 5-hydroxy-pentane.

In general, "hydroxyalkyl" as used herein refers to linear or branched alkyl radicals having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

In general, "alkoxy" as used herein refers to linear or branched oxy-containing radicals each having alkyl portions of one to about ten carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of lower haloalkoxy radicals having one to three carbon atoms include fluoromethoxy, chloromethoxy, trifluoromethoxy, trifluoroethoxy, fluoroethoxy and fluoropropoxy.

In general, "sulfonyl", as used herein whether alone or linked to other terms such as alkylsulfonyl, refers to divalent radicals —$SO_2$—.

In general, "aryl", as used herein alone or in combination, refers to a carbocyclic aromatic system containing one, two or three rings wherein such rings may be attached together in a fused manner. The term "aryl" includes, without limitation, aromatic radicals such as phenyl, naphthyl, indenyl, tetrahydronaphthyl, and indanyl. The "aryl" group may have 1 to 3 substituents such as alkyl, hydroxyl, halo, haloalkyl, nitro, cyano, alkoxy and alkylamino. "Aryl" also includes the moiety wherein the aromatic carbocycle is fused with a $C_{3-6}$cycloalkyl bridge, wherein the bridge optionally includes 1, 2 or 3 heteroatoms selected from N, O and S. For example, phenyl substituted with —O—CH$_2$—O— forms the aryl benzodioxolyl substituent.

In general, "heterocyclyl" as used herein, refers to saturated and partially saturated (or partially unsaturated) heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, oxo, alkoxy, amino and alkylamino.

Examples of saturated heterocyclyl radicals include saturated 3 to 6-membered heteromonocyclic groups containing 1 to 4 nitrogen atoms [e.g., pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g., morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

In general, "heteroaryl" as used herein, refers fully to unsaturated heteroatom-containing ring radicals, where the heteroatoms may be selected from nitrogen, sulfur and oxygen. Examples of heteroaryl radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heteroaryl" also embraces radicals where heterocyclic radicals are fused/condensed with aryl radicals (also referred to herein as "arylheterocycloalkyl"): unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Exemplary heterocyclic radicals include five to ten membered fused or unfused radicals. Specific examples of heteroaryl radicals include quinolyl, isoquinolyl, imidazolyl, pyridyl, thienyl, thiazolyl, oxazolyl, furyl, and pyrazinyl. Other exemplary heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Further examples of suitable heterocycles, some of which have been described above, include, without limitation, the following:

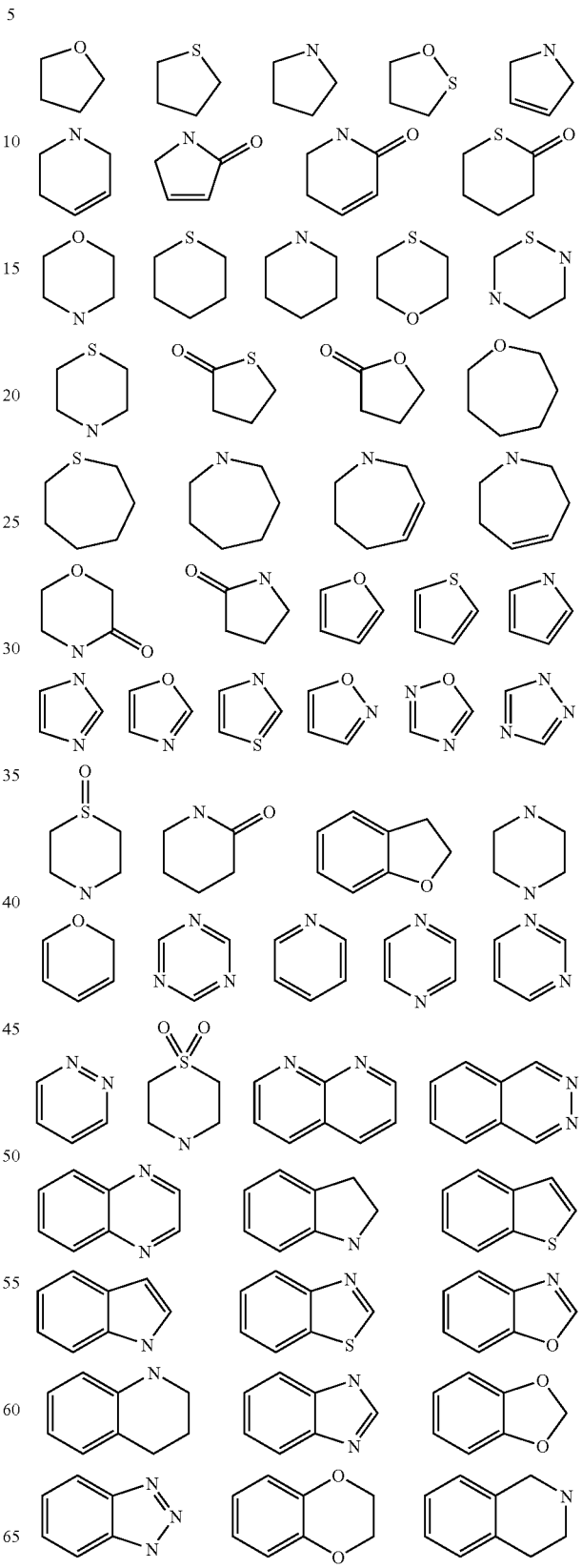

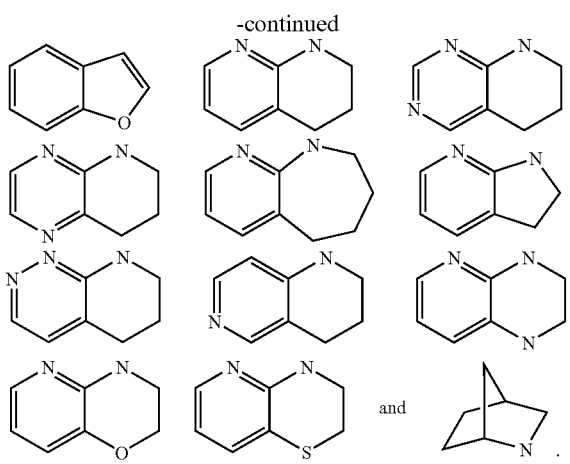

"Saturated or unsaturated" means a substitutent that is completely saturated, completely unsaturated, or has any degree of unsaturation in between. Examples of a saturated or unsaturated 6-membered ring carbocycle would include phenyl, cyclohexyl, cyclohexenyl and cyclohexadienyl.

In general, "salt" refers to a salt form of a free base compound of the present invention, as appreciated by persons of ordinary skill in the art. Salts may be prepared by conventional means, known to those skilled in the art. In general, "pharmaceutically-acceptable", when used in reference to a salt, refers to salt forms of a given compound, which are within governmental regulatory safety guidelines for ingestion and/or administration to a subject. The term "pharmaceutically-acceptable salts" embraces salts commonly used to form alkali metal salts and to form addition salts of free acids or free bases. The nature of the salt is not critical, provided that it is pharmaceutically acceptable.

Suitable pharmaceutically-acceptable acid addition salts of compounds of Formulae I and II may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically acceptable base addition salts of compounds of Formulae I and II include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine.

Additional examples of such acid and base addition salts can be found in Berge et al., J. Pharm. Sci., 66, 1 (1977). All of these salts may be prepared by conventional means from the corresponding compound of the invention by reacting, for example, the appropriate acid or base with the compound of Formula I and II.

Also, the basic nitrogen-containing groups of compounds of Formulae I and II can be quaternized with such agents as lower alkyl halides including, without limitation, methyl, ethyl, propyl, and butyl chloride, bromides and iodides; dialkyl sulfates including dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products may be obtained by quaternizing such basic nitrogen groups in compounds of Formulae I and II.

In general, "derivative" as used herein, refers to simple modifications, readily apparent to those of ordinary skill in the art, on the parent core structure of Formulae I and II, which does not significantly affect (generally decrease) the activity of the compound in-vitro as well as in vivo, in a subject. The term, "derivative" as used herein, is contemplated to include pharmaceutically acceptable derivatives of compounds of Formulae I and II.

In general, "pharmaceutically acceptable" when used with reference to a derivative, is consistent in meaning with reference to a salt, and refers to a derivative that is pharmacologically safe for consumption, generally as determined by a governmental or authorized regulatory body.

In general, "leaving group" as used herein, refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Exemplary leaving groups are indicated herein where appropriate.

In general, "protecting group" as used herein, refers to groups well known in the art which are used to prevent selected reactive groups, such as carboxy, amino, hydroxy, mercapto and the like, from undergoing undesired reactions, such as nucleophilic, electrophilic, oxidation, reduction and the like. Protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, for example those having 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups, including aralkyl groups for example, are also suitable for protecting carboxy, hydroxy and mercapto groups. Alkyl groups are also suitable groups for protecting hydroxy and mercapto groups, such as tert-butyl.

Silyl protecting groups are groups containing silicon atoms, which are optionally substituted, by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. One method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

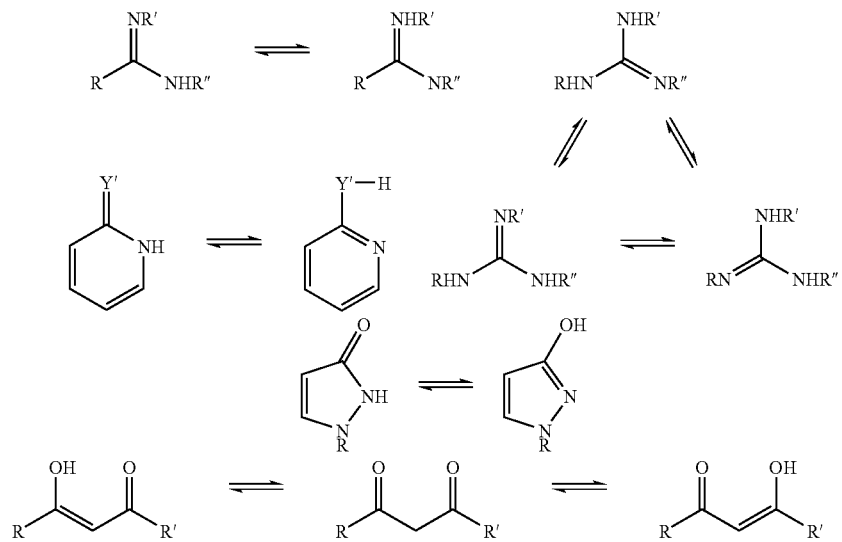

and though one form is named, described, displayed and/or claimed herein, all the tautomeric forms are intended to be inherently included in such name, description, display and/or claim.

Prodrugs of the compounds of this invention are also contemplated by this invention. A "prodrug" is a compound, which when administered to the body of a subject (such as a mammal), breaks down in the subject's metabolic pathway to provide an active compound of Formulae I and II. More specifically, a prodrug is an active or inactive "masked" compound that is modified chemically through in vivo physiological action, such as hydrolysis, metabolism and the like, into a compound of this invention following administration of the prodrug to a subject or patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985).

One common form of a prodrug is a masked carboxylic acid group. Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

In general, "stereoisomer" as used herein refers to a compound having one or more asymmetric centers. Chiral centers in a compound generally cause that compound to exist in many different conformations or stereoisomers. The term "stereoisomers" includes enantiomers, diastereomers, atropisomers and geometric isomers. Stereoisomers generally possess different chemical properties and/or biological activity, as appreciated by those skilled in the art. For example, one stereoisomer may be more active and/or may exhibit beneficial effects in comparison to other stereoisomer(s) or when separated from the other stereoisomer(s). However, it is well within the skill of the ordinary artisan to separate, and/or to selectively prepare said stereoisomers. Accordingly, "stereoisomers" of the present invention necessarily include mixtures of stereoisomers, including racemic mixtures, individual stereoisomers, and optically active forms.

In general, "solvate" when used with reference to a compound refers to a compound, which is associated with one or more molecules of a solvent, such as an organic solvent, inorganic solvent, aqueous solvent or mixtures thereof. The compounds of Formulae I and II may also be solvated, especially hydrated. Hydration may occur during manufacturing of the compounds or compositions comprising the compounds, or the hydration may occur over time due to the hygroscopic nature of the compounds. Compounds of the invention may exist as organic solvates as well, including DMF, ether, and alcohol solvates among others. The identification and preparation of any particular solvate is within the skill of the ordinary artisan of synthetic organic or medicinal chemistry.

In general, "cytokine" as used herein, refers to a secreted protein that affects the functions of other cells, particularly as it relates to the modulation of interactions between cells of the immune system or cells involved in the inflammatory response. Examples of cytokines include but are not limited to interleukin 1 (IL-1), such as IL-1β, interleukin 6 (IL-6), interleukin 8 (IL-8) and TNF, such as TNF-α (tumor necrosis factor-α).

"Treating" or "treatment of" within the context of the instant invention, means an alleviation, in whole or in part, of symptoms associated with a disorder or disease, or halt of further progression or worsening of those symptoms, or prevention or prophylaxis of the disease or disorder. Similarly, as used herein, an "effective amount" or "therapeutically effective amount" of a compound of the invention refers to an amount of the compound that alleviates, in whole or in part, symptoms associated with a disorder or disease, or halts of further progression or worsening of those symptoms, or prevents or provides prophylaxis for the disease or disorder. For example, within the context of treating patients in need of an inhibitor of ACK1, successful treatment may include a reduction in tumor adhesion and anchorage; an alleviation of symptoms related to a cancerous growth or tumor, or proliferation of diseased tissue; a halting in the progression of a disease such as cancer or in the growth of cancerous cells.

In general, "Lck- or ACK-1-mediated disease or disease state" refers to all disease states wherein Lck and/or ACK-1 plays a role, either directly as Lck and/or ACK-1 itself, or by Lck and/or ACK-1 inducing another cytokine or disease-causing agent to be released.

As used herein, the term "subject" is intended to mean a human or other mammal, exhibiting, or at risk of developing, ACK1 or LCK-mediated disease.

III. Compounds and Compositions

The invention provides compounds of Formula I

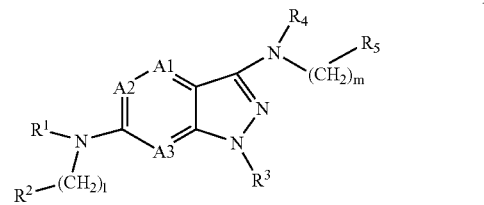

or a stereomer, a tautomer, a solvate, a pharmaceutically acceptable salt, or a prodrug thereof, wherein $A^1$, $A^2$, and $A^3$ are each independently $CR^6$ or N, wherein at least one but no more than two of $A^1$, $A^2$ and $A^3$ are N;

$R^1$ is hydrogen, optionally substituted $C_{1-6}$ alkyl, optionally substituted $C_{2-6}$ alkenyl, optionally substituted $C_{2-6}$ alkynyl, wherein the substituents are selected from halo, cyano, $C_{1-6}$ alkyl, $C_{1-6}$ haloalkyl and $C_{1-6}$ alkoxy;

$R^2$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $R^7$, $NR^8R^9$, $OR^{10}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$;

$R^3$ is optionally substituted alkyl, optionally substituted alkenyl, optionally substituted alkynyl, or an optionally substituted heteroalkyl, wherein the substituents are selected from $R^{17}$, $NR^8R^9$, $OR^{10}$; $SR^{11}$, $COOR^{12}$, $C(O)R^{13}$, $OC(O)R^{13}$, $R^{13}OR^{10}$, $C(O)NR^8R^9$, $C(S)NR^8R^9$, $NR^{14}C(O)R^{15}$, $NR^{14}C(S)R^{15}$, $NR^{14}C(O)NR^8R^9$, $NR^{14}C(S)NR^8R^9$, $NR^{14}(COOR^{12})$, $OC(O)NR^8R^9$, $C(O)NR^8R^9$, $C(S)NR^8R^9$, $NR^{14}C(S)R^{15}$, $NR^{14}C(O)NR^8R^9$, $OC(O)NR^8R^9$, $S(O)_2R^8$, $S(O)_2NR^8R^9$, $NR^{14}S(O)_2NR^8R^9$, $NR^8S(O)_2R^9$, $S(O)_2R^8$, $S(O)_2NR^8R^9$, $NR^{14}S(O)_2NR^8R^9$, and $NR^{14}S(O)_2R^{15}$;

$R^4$ is hydrogen, optionally substituted $C_{1-6}$ alkyl, optionally substituted $C_{2-6}$ alkenyl, optionally substituted $C_{2-6}$ alkynyl, wherein the substituents are selected from halo, $NO_2$, cyano, $C_{1-6}$ alkyl, $C_{1-6}$ haloalkyl and $C_{1-6}$ alkoxy;

$R^5$ is optionally substituted aryl, optionally substituted cycloalkyl, optionally substituted heterocycloalkyl, or optionally substituted heteroaryl, wherein the substituents are selected from $R^7$, $NR^8R^9$, $OR^{10}$; $R^{10}OR^{11}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ and $NR^{17}S(O)_2R^{16}$;

$R^6$ is hydrogen, halogen or optionally substituted $C_{1-6}$ alkyl, wherein the substituents are selected from H, halo, haloalkyl, CN, $NO_2$, OH and $NR^8R^9$;

l and m are independently 0, 1, 2, 3, or 4;

$R^7$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, wherein each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S, or $R^7$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $C_{1-8}$-alkyl, $C_{2-8}$-alkenyl, $C_{2-8}$-alkynyl, $NR^8R^9$, $OR^{10}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$;

$R^8$ and $R^9$ are each independently H, $C_{1-8}$-alkyl, $C_{3-8}$-cycloalkyl, $C_{2-8}$-alkenyl, $C_{2-8}$-alkynyl, $C_{1-8}$-alkylamino-, $C_{1-8}$-dialkylamino-, $C_{1-8}$-alkoxyl, $C_{1-8}$-thioalkyl, $C_{1-8}$-alkoxy-$C_{1-8}$-alkyl, aryl, heteroaryl, or heterocyclyl;

$R^{10}$, $R^{11}$, and $R^{16}$ are each independently H, $C_{1-8}$-alkyl, $C_{2-8}$-alkenyl, $C_{2-8}$-alkynyl, $C_{1-8}$-alkoxy-$C_{1-8}$-alkyl, $C_{3-8}$-cycloalkyl, aryl, heterocyclyl, $C_{1-8}$-alkyl-heterocyclyl or heterocyclyl-$C_{1-8}$-alkyl;

$R^{12}$, $R^{13}$, $R^{14}$, and $R^{15}$ are each independently H, $C_{1-8}$-alkyl, $C_{3-8}$-cycloalkyl, $C_{2-8}$-alkenyl, $C_{2-8}$-alkynyl, $C_{1-8}$-alkylamino-, $C_{1-8}$-dialkylamino-, $C_{1-8}$-alkoxyl, $C_{1-8}$-thioalkyl, aryl, heteroaryl, heterocyclyl or alkylheterocyclyl; and $R^{17}$ is H, halo, CN, $NO_2$, or Cy;

Cy is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $C_{1-8}$-alkyl, $C_{2-8}$-alkenyl, $C_{2-8}$-alkynyl, $NR^8R^9$, $OR^{10}$, $SR^{11}$, $COOR^{12}$, $C(O)R^{13}$, $R^{13}OR^{10}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$.

In one aspect, $A^1$ is $CR^6$, and $A^2$ and $A^3$ are both N. In another aspect, $A^3$ is N, and $A^1$ and $A^2$ are both $CR^6$. In a further aspect, $A^2$ is $CR^6$, and $A^1$ and $A^3$ are both N. In another aspect, $A^2$ is N, and $A^1$ and $A^3$ are both $CR^6$.

In one aspect, l and m can be both 0.

In one aspect, $R^1$ can be H.

In one aspect, $R^2$ can be phenyl. In another aspect, $R^2$ is phenylene and $R^7$ is halogen or is $OR^{10}$.

In one aspect, $R^{10}$ is heterocyclyl, $C_{1-8}$-alkyl-heterocyclyl or heterocyclyl-$C_{1-8}$-alkyl. In another aspect, $R^{10}$ is piperazinyl, methylpiperazinylene, piperazinylalkylene, pyrrolidinyl, or dimethylpiperazinyl.

In one aspect, $R^3$ is optionally substituted alkyl or alkenyl. In another aspect, $R^3$ is alkyl substituted with one or more $OR^{10}$. In a further aspect, $R^3$ can be alkyl substituted with one or more $R^{17}$. In one aspect, $R^{17}$ can be Cy. In one aspect, $R^{17}$ can be optionally substituted pyrrolidinyl, furanyl, thiophenyl, 2H-pyrrolyl, pyrrolyl, 2-pyrrolinyl, 3-pyrrolinyl, 1,3-dioxolanyl, oxazolyl, thiazolyl, imidazolyl, 2-imidazolinyl, imidaxzolidinyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, pyridinyl, piperidinyl, 1,4-dioxanyl, morpholinyl, 1,4-dithianyl, thiomorpholinyl, pyradazinyl, pyrimidinyl, pyrazinyl, oxioerazinyl, 1,3,5-triazinyl or 1,3,5-trithianyl.

In one aspect, $R^{10}$ can be hydrogen or $C_{1-8}$-alkyl.

In one aspect, $R^3$ can be alkyl substituted with one or more $NR^8R^9$. In one aspect, $R^8$ and $R^9$ can be independently hydrogen or $C_{1-8}$-alkyl. In another aspect, $R^3$ can be alkyl substituted with one or more $COOR^{12}$, one or more $C(O)R^{13}$, or one or more $C(O)NR^8R^9$.

In one aspect, $R^4$ can be hydrogen or optionally substituted $C_{1-6}$ alkyl. In another aspect, $R^4$ can be hydrogen and $R^5$ can be optionally substituted aryl.

The invention further provides compounds of Formula II

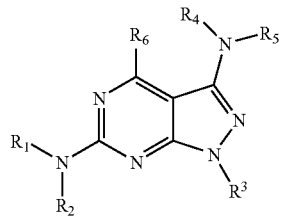

II or a stereomer, a tautomer, a solvate, a pharmaceutically acceptable salt, or a prodrug thereof, wherein $R^1$ is hydrogen or $C_{1-6}$ alkyl optionally substituted with 1-3 substituents of halo, cyano, $C_{1-6}$ alkyl, $C_{1-6}$ haloalkyl or $C_{1-6}$ alkoxy;

$R^2$ is $C_{3-10}$-cycloalkyl, phenyl, naphthyl, pyridyl, pyrimidinyl, pyridazinyl, triazinyl, piperidinyl, piperazinyl, pyrrolyl, imidazolyl, pyrazolyl, triazolyl, pyrrolidinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, phthalazinyl, morpholinyl, thiophenyl, furyl, dihydrofuryl, tetrahydrofuryl, thiazolyl, oxazolyl, isoxazolyl, isothiazolyl, indolyl, isoindolyl, indolinyl, benzofuranyl, dihydrobenzofuranyl, benzothiophenyl, benzimidazolyl, benzoxazolyl, benzisoxazolyl or benzothiazolyl, each of which is optionally substituted independently with 1-3 substituents of $R^7$, $NR^8R^9$, $OR^{10}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$;

$R^3$ is optionally substituted alkyl, optionally substituted alkenyl, optionally substituted alkynyl, or an optionally substituted heteroalkyl, wherein the substituents are selected from $R^{17}$, $NR^8R^9$, $OR^{10}$; $SR^{11}$, $COOR^{12}$, $C(O)R^{13}$, $OC(O)R^{13}$, $R^{13}OR^{10}$, $C(O)NR^8R^9$, $C(S)NR^8R^9$, $NR^{14}C(O)R^{15}$, $NR^{14}C(S)R^{15}$, $NR^{14}C(O)NR^8R^9$, $NR^{14}C(S)NR^8R^9$, $NR^{14}(COOR^{12})$, $OC(O)NR^8R^9$, $C(O)NR^8R^9$, $C(S)NR^8R^9$, $NR^{14}C(S)R^{15}$, $NR^{14}C(O)NR^8R^9$, $OC(O)NR^8R^9$, $S(O)_2R^8$, $S(O)_2NR^8R^9$, $NR^{14}S(O)_2NR^8R^9$, $NR^8S(O)_2R^9$, $S(O)_2R^8$, $S(O)_2NR^8R^9$, $NR^{14}S(O)_2NR^8R^9$ and $NR^{14}S(O)_2R^{15}$;

$R^4$ is hydrogen or $C_{1-6}$ alkyl optionally substituted with 1-3 substituents of halo, cyano, $C_{1-6}$ alkyl, $C_{1-6}$ haloalkyl or $C_{1-6}$ alkoxy;

$R^5$ is $C_{3-10}$-cycloalkyl, phenyl, naphthyl, pyridyl, pyrimidinyl, pyridazinyl, triazinyl, piperidinyl, piperazinyl, pyrrolyl, imidazolyl, pyrazolyl, triazolyl, pyrrolidinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, phthalazinyl, morpholinyl, thiophenyl, furyl, dihydrofuryl, tetrahydrofuryl, thiazolyl, oxazolyl, isoxazolyl, isothiazolyl, indolyl, isoindolyl, indolinyl, indazolyl, benzofuranyl, dihydrobenzofuranyl, benzothiophenyl, benzimidazolyl, benzoxazolyl, benzisoxazolyl or benzothiazolyl, each of which is optionally substituted independently with 1-3 substituents of $R^7$, $NR^8R^9$, $OR^{10}$; $R^{10}OR^{11}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ and $NR^{17}S(O)_2R^{16}$;

$R^6$ is hydrogen, halogen or $C_{1-6}$ alkyl optionally substituted with 1-3 substituents of halo, haloalkyl, CN, $NO_2$, OH and $NR^8R^9$;

$R^7$ is halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, wherein each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S, or $R^7$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $C_{1-8}$-alkyl, $C_{2-8}$-alkenyl, $C_{2-8}$-alkynyl, $NR^8R^9$, $OR^{10}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$;

$R^8$ and $R^9$ are each independently H, $C_{1-8}$-alkyl, $C_{3-8}$-cycloalkyl, $C_{2-8}$-alkenyl, $C_{2-8}$-alkynyl, $C_{1-8}$-alkylamino-, $C_{1-8}$-dialkylamino-, $C_{1-8}$-alkoxyl, $C_{1-8}$-thioalkyl, $C_{1-8}$-alkoxy-$C_{1-8}$-alkyl, aryl, heteroaryl, or heterocyclyl;

$R^{10}$, $R^{11}$, and $R^{16}$ are each independently H, $C_{1-8}$-alkyl, $C_{2-8}$-alkenyl, $C_{2-8}$-alkynyl, $C_{1-8}$-alkoxy-$C_{1-8}$-alkyl, $C_{3-8}$-cycloalkyl, aryl, heterocyclyl, $C_{1-8}$-alkyl-heterocyclyl or heterocyclyl-$C_{1-8}$-alkyl;

$R^{12}$, $R^{13}$, $R^{14}$ and $R^{15}$ are each independently H, $C_{1-8}$-alkyl, $C_{3-8}$-cycloalkyl, $C_{2-8}$-alkenyl, $C_{2-8}$-alkynyl, $C_{1-8}$-alkylamino-, $C_{1-8}$-dialkylamino-, $C_{1-8}$-alkoxyl, $C_{1-8}$-thioalkyl, aryl, heteroaryl, heterocyclyl or alkyl-heterocyclyl; and $R^{17}$ is halo, CN, $NO_2$, or ring selected from $C_{3-10}$-cycloalkyl, phenyl, naphthyl, pyridyl, pyrimidinyl, pyridazinyl, triazinyl, piperidinyl, piperazinyl, pyrrolyl, imidazolyl, pyrazolyl, triazolyl, pyrrolidinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, phthalazinyl, morpholinyl, thiophenyl, furyl, dihydrofuryl, tetrahydrofuryl, thiazolyl, oxazolyl, isoxazolyl, isothiazolyl, indolyl, isoindolyl, indolinyl, benzofuranyl, dihydrobenzofuranyl, benzothiophenyl, benzimidazolyl, benzoxazolyl, benzisoxazolyl and benzothiazolyl, each ring of which is optionally substituted independently with 1-3 substituents of halo, haloalkyl, CN, $NO_2$, $NH_2$, OH, $C_{1-8}$-alkyl, $C_{2-8}$-alkenyl, $C_{2-8}$-alkynyl, $C_{1-8}$-alkylamino-, $C_{1-8}$-dialkylamino-, $C_{1-8}$-alkoxyl or $C_{1-8}$-thioalkyl.

In one aspect, $R^1$ can be hydrogen; and $R^2$ can be phenyl, naphthyl, pyridyl, pyrimidinyl, pyridazinyl, triazinyl, pyrrolyl, imidazolyl, pyrazolyl, triazolyl, quinolinyl, isoquinolinyl, quinazolinyl, isoquinazolinyl, phthalazinyl, thiophenyl, furyl, thiazolyl, oxazolyl, isoxazolyl, isothiazolyl, indolyl, isoindolyl, indolinyl, benzofuranyl, benzothiophenyl, benzimidazolyl, benzoxazolyl, benzisoxazolyl or benzothiazolyl, each of which is optionally substituted independently with 1-3 substituents of $R^7$, $NR^8R^9$, $OR^{10}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2 NR^8R^9$ or $NR^{14} S(O)_2R^{16}$.

In one aspect, $R^4$ can be hydrogen; and $R^5$ can be phenyl, naphthyl, pyridyl, pyrimidinyl, pyridazinyl, triazinyl, pyrrolyl, imidazolyl, pyrazolyl, triazolyl, quinolinyl, isoquinolinyl, quinazolinyl, isoquinazolinyl, phthalazinyl, thiophenyl, furyl, thiazolyl, oxazolyl, isoxazolyl, isothiazolyl, indolyl, isoindolyl, indolinyl, benzofuranyl, benzothiophenyl, benzimidazolyl, benzoxazolyl, benzisoxazolyl or benzothiazolyl, each of which is optionally substituted independently with 1-3 substituents of $R^7$, $NR^8R^9$, $OR^{10}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2 NR^8R^9$ or $NR^{14}S(O)_2R^{16}$.

In one aspect, $R^3$ can be optionally substituted alkyl or optionally substituted alkenyl, wherein the substituents are selected from $R^{17}$, $NR^8R^9$, $OR^{10}$; $SR^{11}$, $COOR^{12}$, $C(O)R^{13}$, $OC(O)R^{13}$, $R^{13}OR^{10}$, $C(O)NR^8R^9$, $C(S)NR^8R^9$, $NR^{14}C(O)R^{15}$, $NR^{14}C(S)R^{15}$, $NR^{14}C(O)NR^8R^9$, $NR^{14}C(S)NR^8R^9$, $NR^{14}(COOR^{12})$, $OC(O)NR^8R^9$, $C(O)NR^8R^9$, $C(S)NR^8R^9$, $NR^{14}C(S)R^{15}$, $NR^{14}C(O)NR^8R^9$, $OC(O)NR^8R^9$, $S(O)_2R^8$, $S(O)_2NR^8R^9$, $NR^{14}S(O)_2NR^8R^9$, $NR^8S(O)_2R^9$, $S(O)_2R^8$, $S(O)_2NR^8R^9$, $NR^{14}S(O)_2NR^8R^9$ and $NR^{14}S(O)_2R^{15}$.

In one aspect, the inventions provides the compounds and pharmaceutically acceptable salts thereof, selected from:

1-(but-3-enyl)-$N^3$-(2,6-dimethylphenyl)-$N^6$-phenyl-1H-pyrazolo[3,4-d]pyrimidine-3,6-diamine;

4-(3-(2,6-dimethylphenylamino)-6-(phenylamino)-1H-pyrazolo[3,4-d]pyrimidin-1-yl)butane-1,2-diol;

1-(2-(1,3-dioxolan-4-yl)ethyl)-N3-(2,6-dimethylphenyl)-N6-phenyl-1H-pyrazolo[3,4-d]pyrimidine-3,6-diamine;

3-(3-(2,6-dimethylphenylamino)-6-(phenylamino)-1H-pyrazolo[3,4-d]pyrimidin-1-yl)propan-1-ol;

1-(3-(dimethylamino)propyl)-N3-(2,6-dimethylphenyl)-N6-phenyl-1H-pyrazolo[3,4-d]pyrimidine-3,6-diamine;

$N^3$-(2,6-dimethylphenyl)-1-(3-(methylamino)propyl)-$N^6$-phenyl-1H-pyrazolo[3,4-d]pyrimidine-3,6-diamine;

1-(3-(diethylamino)propyl)-$N^3$-(2,6-dimethylphenyl)-$N^6$-phenyl-1H-pyrazolo[3,4-d]pyrimidine-3,6-diamine;

$N^3$-(2,6-dimethylphenyl)-$N^6$-phenyl-1-(3-(pyrrolidin-1-yl)propyl)-1H-pyrazolo[3,4-d]pyrimidine-3,6-diamine;

1-(dimethylamino)-4-(3-(2,6-dimethylphenylamino)-6-(phenylamino)-1H-pyrazolo[3,4-d]pyrimidin-1-yl)butan-2-ol;

4-(3-(2,6-dimethylphenylamino)-6-(phenylamino)-1H-pyrazolo[3,4-d]pyrimidin-1-yl)-1-(pyrrolidin-1-yl)butan-2-ol;

4-(3-(2,6-dimethylphenylamino)-6-(phenylamino)-1H-pyrazolo[3,4-d]pyrimidin-1-yl)butan-2-ol;

4-(3-(2,6-dimethylphenylamino)-6-(phenylamino)-1H-pyrazolo[3,4-d]pyrimidin-1-yl)butan-2-ol;

$N^3$-(2,6-dimethyl-phenyl)-$N^6$-phenyl-1-(3-piperidin-1-yl-propyl)-1H-pyrazolo[3,4-d]pyrimidine-3,6-diamine;

$N^3$-(2,6-dimethyl-phenyl)-$N^6$-(4-piperazin-1-yl-phenyl)-1-(3-piperidin-1-yl-propyl)-1H-pyrazolo[3,4-d]pyrimidine-3,6-diamine;

$N^3$-(2,6-dimethyl-phenyl)-$N^6$-[4-(4-methyl-piperazin-1-yl)-phenyl]-1-(3-piperidin-1-yl-propyl)-1H-pyrazolo[3,4-d]pyrimidine-3,6-diamine;

$N^3$-(2,6-dimethyl-phenyl)-1-(2-morpholin-4-yl-ethyl)-$N^6$-phenyl-1H-pyrazolo[3,4-d]pyrimidine-3,6-diamine;

$N^3$-(2,6-dimethyl-phenyl)-$N^6$-[4-(2-methoxy-ethoxy)-phenyl]-1-(2-morpholin-4-yl-ethyl)-1H-pyrazolo[3,4-d]pyrimidine-3,6-diamine;

$N^3$-(2,6-dimethyl-phenyl)-$N^6$-[4-(4-methyl-piperazin-1-yl)-phenyl]-1-(2-morpholin-4-yl-ethyl)-1H-pyrazolo[3,4-d]pyrimidine-3,6-diamine;

$N^3$-(2,6-dimethyl-phenyl)-$N^6$-[4-(2-methoxy-ethoxy)-phenyl]-1-(3-methoxy-3-methyl-butyl)-1H-pyrazolo[3,4-d]pyrimidine-3,6-diamine;

$N^3$-(2,6-dimethyl-phenyl)-1-(3-methoxy-3-methyl-butyl)-$N^6$-[4-(methylpiperazin-1-yl)phenyl]-1H-pyrazolo[3,4-d]pyrimidine-3,6-diamine;

$N^3$-(2,6-dimethyl-phenyl)-1-(3-methoxy-3-methylbutyl)-$N^6$-(4-piperazin-1-yl-phenyl)-1H-pyrazolo[3,4-d]pyrimidine-3,6-diamine;

$N^3$-(2,6-dimethylphenyl)-$N^6$-[3-fluoro-4-(3-(piperidin-1-yl)propoxy)phenyl]-1-(3-methoxy-3-methylbutyl)-1H-pyrazolo[3,4-d]pyrimidine-3,6-diamine;

$N^3$-(2,6-dimethylphenyl)-1-(3-methoxy-3-methylbutyl)-1H-indazole-3,6-diamine;

$N^3$-(2,6-dimethylphenyl)-1-(3-methoxy-3-methylbutyl))-$N^6$-phenyl-1H-indazole-3,6-diamine;

$N^3$-(2,6-dimethylphenyl)-1-$N^6$-(4-(3,5-dimethylpiperazin-1-yl)phenyl)-1-(3-methoxy-3-methylbutyl)-1H-indazole-3,6-diamine;

$N^3$-(2,6-dimethylphenyl)-1-$N^6$-(4-piperazin-1-yl)phenyl)-1-((tetrahydro-2H-pyran-4-yl)methyl)-1H-indazole-3,6-diamine;

$N^3$-(2,6-dimethylphenyl)-1-$N^6$-(3-fluoro-4-(piperidin-1-yl)propoxy)phenyl)-1-((tetrahydro-2H-pyran-4-yl)methyl)-1H-indazole-3,6-diamine;

$N^3$-(2,6-dimethylphenyl)-$N^6$-phenyl-1-((tetrahydro-2H-pyran-4-yl)methyl)-1H-indazole-3,6-diamine;

ethyl-2-(3-(2,6-dimethylphenylamino)-6-(phenylamino)-1H-indazole-1-yl)acetate;

(R)—$N^3$-(2,6-dimethylphenyl)-$N^6$-(4-fluorophenyl)-1-(3-(2-(methoxymethyl)pyrrolidin-1-yl)propyl)-1H-indazole-3,6-diamine;

(R)—$N^3$-(2,6-dimethylphenyl)-1-(3-(2-(methoxymethyl)pyrrolidin-1-yl)propyl)-$N^6$-phenyl-1H-indazole-3,6-diamine;

(R)—$N^3$-(2,6-dimethylphenyl)-1-(3-(2-(methoxymethyl)pyrrolidin-1-yl)propyl)-$N^6$-(4-piperazin-1-yl)phenyl-1H-indazole-3,6-diamine;

(R)—$N^3$-(2,6-dimethylphenyl)-1-(3-(2-(methoxymethyl)pyrrolidin-1-yl)propyl)-1H-indazole-3,6-diamine;

2-(3-(2,6-dimethylphenylamino)-6-(phenylamino)-1H-indazol-1-yl)acetic acid;

2-(3-(2,6-dimethylphenylamino)-6-(phenylamino)-1H-indazol-1-yl)-1-(4-methylpiperazin-1-yl)ethanone;

2-(3-(2,6-dimethylphenylamino)-6-(phenylamino)-1H-indazol-1-yl)-1-(piperazin-1-yl)ethanone;

$N^3$-(2,6-dimethylphenyl)-1-(2-(4-methylpiperazin-1-yl)ethyl)-$N^6$-phenyl-1H-indazole-3,6-diamine;

1-(3-methoxy-3-methyl-butyl)-$N^3$, $N^6$-diphenyl-1H-pyrazolo[3,4-d]pyrimidine-3,6-diamine;

1-(3-methoxy-3-methyl-butyl)-$N^6$-[4-(4-methyl-piperazin-1-yl)-phenyl-$N^3$-phenyl-1H-pyrazolo[3,4-d]pyrimidine-3,6-diamine;

1-(3-methoxy-3-methyl-butyl)-$N^6$-phenyl-$N^3$-(2,4,6-trimethyl-phenyl)-1H-pyrazolo[3,4-d]pyrimidine-3,6-diamine;

$N^3$-(4-fluoro-2,6-dimethyl-phenyl)-1-(3-methoxy-3-methyl-butyl)-$N^6$-phenyl-1H-pyrazolo[3,4-d]pyrimidine-3,6-diamine;

$N^3$-(4-fluoro-2,6-dimethyl-phenyl)-1-(3-methoxy-3-methyl-butyl)-$N^6$-[4-(4-methyl-piperazin-1-yl)-phenyl]-1H-pyrazolo[3,4-d]pyrimidine-3,6-diamine;

$N^3$-(2,6-dichlorophenyl)-1-(3-methoxy-3-methylbutyl)-$N^6$-[4-(4-methyl-piperazin-1-yl)-phenyl]-1H-indazole-3,6-diamine;

9H-fluoren-9-yl)methyl 4-(4-(3-(2,6-dichlorophenylamino)-1-(3-methoxy-3-methyl-butyl)-1H-indazol-6-ylamino)phenyl)piperazine-1-carboxylate;

$N^3$-(2,6-dichlorophenyl)-$N^6$-(3-fluoro-4-(2-(pyrrolidin-1-yl)ethoxy)phenyl)-1-(3-methoxy-3-methylbutyl)-1H-pyrazolo[3,4-d]pyrimidine-3,6-diamine and $N^3$-(2,6-dichlorophenyl)-1-(3-methoxy-3-methylbutyl)-$N^6$-methyl-1H-pyrazolo[3,4-d]pyrimidine-3,6-diamine.

In one aspect, the invention provides pharmaceutical compositions comprising a pharmaceutically acceptable carrier and compounds summarized above.

IV. Methods of Use

For the treatment of Lck-mediated diseases, ACK-1 mediated diseases and/or other diseases listed above, the compounds of the present invention may be administered by several different modes, including without limitation, oral, parental, by spray inhalation, rectal, or topical, as discussed herein. The term parenteral as used herein, includes subcutaneous, intravenous, intramuscular, intrasternal, infusion techniques or intraperitoneal administration.

Treatment of diseases and disorders herein is intended to also include therapeutic administration of a compound of the invention (or a pharmaceutical salt, derivative or prodrug thereof) or a pharmaceutical composition containing said compound to a subject (i.e., an animal, for example a mammal, such as a human) believed to be in need of preventative treatment, such as, for example, pain, inflammation and the like. Treatment also encompasses administration of the compound or pharmaceutical composition to subjects not having been diagnosed as having a need thereof, i.e., prophylactic administration to the subject. Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

While it may be possible to administer a compound of the invention alone, in the methods described, the compound administered is generally present as an active ingredient in a desired dosage unit formulation, such as pharmaceutically acceptable composition containing conventional pharmaceutically acceptable carriers. Thus, in another aspect of the invention, there is provided a pharmaceutical composition comprising a compound of this invention in combination with a pharmaceutically acceptable carrier. Acceptable pharmaceutical carriers generally include diluents, excipients, adjuvants and the like as described herein.

A pharmaceutical composition of the invention may comprise an effective amount of a compound of the invention or an effective dosage amount of a compound of the invention. An effective dosage amount of a compound of the invention includes an amount less than, equal to, or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound may be administered by administering a portion of the composition.

The pharmaceutical compositions may generally be prepared by mixing one or more compounds of Formulae I or II including stereoisomers or tautomers, solvates, pharmaceutically acceptable salts, derivatives or prodrugs thereof, with pharmaceutically acceptable carriers, excipients, binders, adjuvants, diluents and the like, to form a desired administrable formulation to treat or ameliorate a variety of disorders related to the activity of Lck, particularly inflammation, or related to the activity ACK-1, particularly cancer.

Pharmaceutical compositions can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described herein, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (2000); and "Pharmaceutics The Science of Dosage Form Design, $2^{nd}$ Ed. (Aulton, ed.) Churchill Livingstone (2002). The following dosage forms are given by way of example and should not be construed as limiting the invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or stereoisomers, solvates, prodrugs, pharmaceutically acceptable salts or tautomers thereof, with at least one additive or excipient such as a starch or other additive and tableted, encapsulated or made into other desirable forms for conventional administration. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, and the like may be added for oral or parenteral administration.

For nasal administration, the pharmaceutical formulations may be a spray or aerosol containing an appropriate solvent and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms for parenteral administration generally include aqueous suspensions or oil suspensions, which may be prepared using a suitable dispersant or wetting agent and a suspending agent. Injectable forms may be in solution phase or a powder suitable for reconstitution as a solution. Both are prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is solid phase at room temperature but liquid phase at those temperatures suitable to release a drug inside the body, such as in the rectum. Various other agents and additives may be used in the preparation of suppositories as is well known to those of skill in the art.

The formulations of the invention may be designed to be short-acting, fast-releasing, long-acting, and sustained-releasing as described below. Thus, the pharmaceutical formulations may also be formulated for controlled release or for slow release. The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. Typically, the compound or compounds of the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The dosage regimen for treating Lck- or ACK1-mediated diseases and other diseases listed above with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, for example from about 0.1 mg to 10 mg/kg, or from about 0.25 mg to 1 mg/kg are useful for all methods of use disclosed herein.

For oral administration, the pharmaceutical composition may be in the form of, for example, a capsule, a tablet, a suspension, or liquid. The pharmaceutical composition can be made in the form of a dosage unit containing a given amount of the active ingredient. For example, these may contain an amount of active ingredient from about 1 to 2000 mg, for example from about 1 to 500 mg, or from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, such as from about 0.1 to about 10 mg/kg, or from about 0.25 mg to 1 mg/kg.

Formulations suitable for topical administration include liquid or semi-liquid preparations suitable for penetration through the skin (e.g., liniments, lotions, ointments, creams, or pastes) and drops suitable for administration to the eye, ear, or nose.

A suitable topical dose of active ingredient of a compound of the invention is 0.1 mg to 150 mg administered one to four, for example one or two times daily. For topical administration, the active ingredient may comprise from 0.001% to 10% w/w, e.g., from 1% to 2% by weight of the formulation, although it may comprise as much as 10% w/w, but typically not more than 5% w/w. In one aspect, the concentration is from 0.1% to 1% of the formulation.

The pharmaceutical compositions may be subjected to conventional pharmaceutical operations such as sterilization and/or may contain conventional adjuvants, such as preservatives, stabilizers, wetting agents, emulsifiers, buffers etc. The pharmaceutically active compounds of this invention can be processed in accordance with conventional methods of pharmacy to produce medicinal agents for administration to patients, including humans and other mammals.

While the compounds of the present invention can be administered as the sole active pharmaceutical agent, they can also be used in combination with one or more compounds of the invention or with one or more other agents. When administered as a combination, the therapeutic agents can be formulated and given to the subject as a single composition or the combination of therapeutic agents can be formulated and given to the subject as separate compositions that are given at the same time or different times.

Treatment may also include administering the pharmaceutical formulations of the present invention in combination with other therapies. For example, the compounds and pharmaceutical formulations of the present invention may be administered before, during, or after surgical procedure and/or radiation therapy. Alternatively, the compounds of the invention can also be administered in conjunction with other anti-proliferative agents including those used in antisense and gene therapy.

One category of suitable antiproliferative agents useful in the present invention is the alkylating agents, a group of highly reactive chemotherapeutics that form covalent linkages with nucleophilic centers (e.g., hydroxyl and carboxyl). Chemically, the alkylating agents can be divided into five groups: nitrogen mustards, ethylenimines, alkylsulfonates, triazenes, and nitrosureas. The nitrogen mustards are frequently useful in, for example, the treatment of chronic lymphocytic leukemia, Hodgkin's disease, malignant lymphoma, small cell lung cancer and breast and testicular cancer. Exemplary nitrogen mustards include chlorambucil, cyclophosphamide, ifosfamide, mechlorethamine, melphalan and uracil mustard. The ethylenimines, the most common of which is thiotepa, may be useful in bladder tumors and in breast and ovarian adenocarcinomas. The alkyl sulfonates are useful in the treatment of chronic myelogenous leukemia and other myeloproliferative disorders. Exemplary alkyl sulfonates include busulfan and piposulfan. The triazines, which include, e.g., dacarbazine, are useful in the treatment of malignant melanomas and sarcomas. Temozolomide, an analog of dacarbazine, may also be used in the methods and compositions of the present invention. Finally, the nitrosureas are especially useful against brain tumors, but also are effective for, e.g., multiple myeloma, malignant melanoma, and lymphoma. Exemplary nitrosureas include carmustine and lomustine.

Another category of antiproliferative agents suitable for use in the present invention is the antimetabolites, structural analogs of normally occurring metabolites that interfere with normal nucleic acid biosynthesis. This category of agents may be subdivided into the folic acid analogs, purine analogs and pyrimidine analogs based on the function of the metabolite with which the agent interferes. The most common folic acid analog is methotrexate, useful in the treatment of choriocarcinoma, leukemias, neoplasms and psoriasis. The purine analogs, such as mercaptopurine, thioguanine and azathioprine, may be useful in leukemias. The pyrimidine analogs are useful in the treatment of, for example, leukemia and carcinomas of the gastrointestinal tract, mammary gland, and bladder. Exemplary pyrimidine analogs include fluorouracil (5-FU), UFT (uracil and ftorafur), capecitabine, gemcitabine and cytarabine.

The vinca alkaloids, natural product-based agents that exert their cytotoxicity by binding to tubulin, represent another category of antiproliferative agents suitable for use in the present invention. The vinca alkaloids are useful in, for example, the treatment of lymphomas, leukemias, and lung, breast, testicular, bladder and head and neck cancers. Exemplary agents include vinblastine, vincristine, vinorelbine and vindesine. The taxanes, agents which promote microtubule assembly, and the podophyllotoxins, agents which inhibit topoisomerases, represent related categories of antiproliferative agents that may be useful in the methods and compositions of the present invention. Exemplary taxanes include paclitaxol and docetaxol, which are useful in breast and lung cancers, among others. Exemplary podophyllotoxins include etoposide (useful in, for example, lymphoma and Hodgkin's disease), teniposide, ironotecan (useful in, for example, colon, rectal and lung cancer) and topotecan, the latter two of which act via inhibition of topoisomerase I.

Antineoplastic antibiotics represent another category of antiproliferative agents useful in the methods and compositions of the present invention. These agents exert their effects by binding to or complexing with DNA. Exemplary agents include daunorubicin, doxorubicin, epirubicin, mitoxantrone, mitomycin, dactinomycin, plicamycin, and bleomycin. The antibiotics are useful in a diverse range of disorders, including Hodgkin's disease, leukemia, lymphoma, and lung cancer.

The methods and compositions of the present invention may comprise other antiproliferative agents, including the platinum complexes (e.g., cisplatin and carboplatin, which are especially useful in the treatment of lung, head and neck, ovarian and breast cancer); enzymes (e.g., L-asparaginase); hormone-related therapy hormone (e.g., tamoxifen, leuprolide, flutamide, megesterol acetate, diethylstilbestrol, prednisone and estradiol cypionate); hydroxyurea; methylhydrazine derivatives such as procarbazine; adrenocortical suppressants, e.g., mitotane, aminoglutethimide; aromatase inhibitors (e.g., anastrozole); and biologic response modifiers (e.g., interferon-A).

Furthermore, the methods and compositions of the present invention may comprise antiproliferative agents that result from the combination of two or more agents including, for example, prednimustine (a conjugate of prednisone and chlorambucil) and estramustine (a conjugate of nornitrogen mustard and estradiol).

The methods and compositions of the present invention may comprise a combination with another kinase inhibitor. Although the present invention is not limited to any particular kinase, kinase inhibitors contemplated for use include, without limitation, tyrphostin AG490 (2-cyano-3-(3,4-dihydroxyphenyl)-N-(benzyl)-2-propenamide), Iressa (ZD1839; Astra Zeneca); Gleevec (STI-571 or imatinib mesylate; Novartis); SU5416 (Pharmacia Corp./Sugen); and Tarceva (OSI-774; Roche/Genentech/OSI Pharmaceuticals).

IV. Methods of Synthesis

Methods for the preparation of the compounds described in the present invention are shown in the following schemes. One of skill in the art will understand that similar methods can be used for the synthesis of other compounds of the invention.

Scheme 1 shows a general method for preparation of compounds of the invention wherein, for the purposes of this section only, $R^1$ is an alkyl or heteroalkyl group, $R^2$-$R^5$ are alkyl, alkoxy, aminoalkyl, halide or H, and $R^6$ is alkyl or H. The synthetic route begins with readily available uracil-5-carboxylic acid 1. Chlorination of 1 with a combination of $PCl_5$ and $POCl_3$ at reflux provides acid chloride 2, which then undergoes amide formation by condensation of with a substituted aniline 3 in the presence of a weakly basic resin to give amide 4. Reaction of 4 with a monosubstituted hydrazine 5 and a tertiary amine base, for example $Et_3N$ or i-$Pr_2EtN$, in a suitable organic solvent, such as THF or ether, results in the formation of hydrazine 6. Compound 6 readily undergoes cyclization with a chlorinating reagent, such as $POCl_3$, $PCl_3$, $PCl_5$ or $SOCl_2$, at elevated temperature in a suitable organic solvent, for example benzene or toluene, to generate pyrazole 7. Condensation of 7 and a substituted aniline 8 in the presence of an acid, such as TFA, HCl or HCOOH, and a high boiling organic solvent, such as 1,4-dioxane, 1-butanol, or a mixture of 1,4-dioxane and 1-butanol, gives compounds of the structure 9. Similarly, compounds of the structure 10 are synthesized by reacting 7 with ammonia gas or an aminoalkane in the presence of an acid, such as TFA, HCl or HCOOH, and a high boiling organic solvent, such as 1,4-dioxane, 1-butanol, or a mixture of 1,4-dioxane and 1-butanol, in a sealed reaction vessel at elevated temperature.

Scheme 1

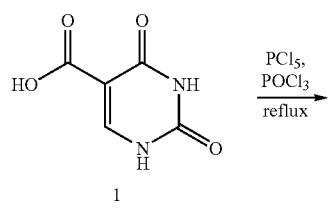

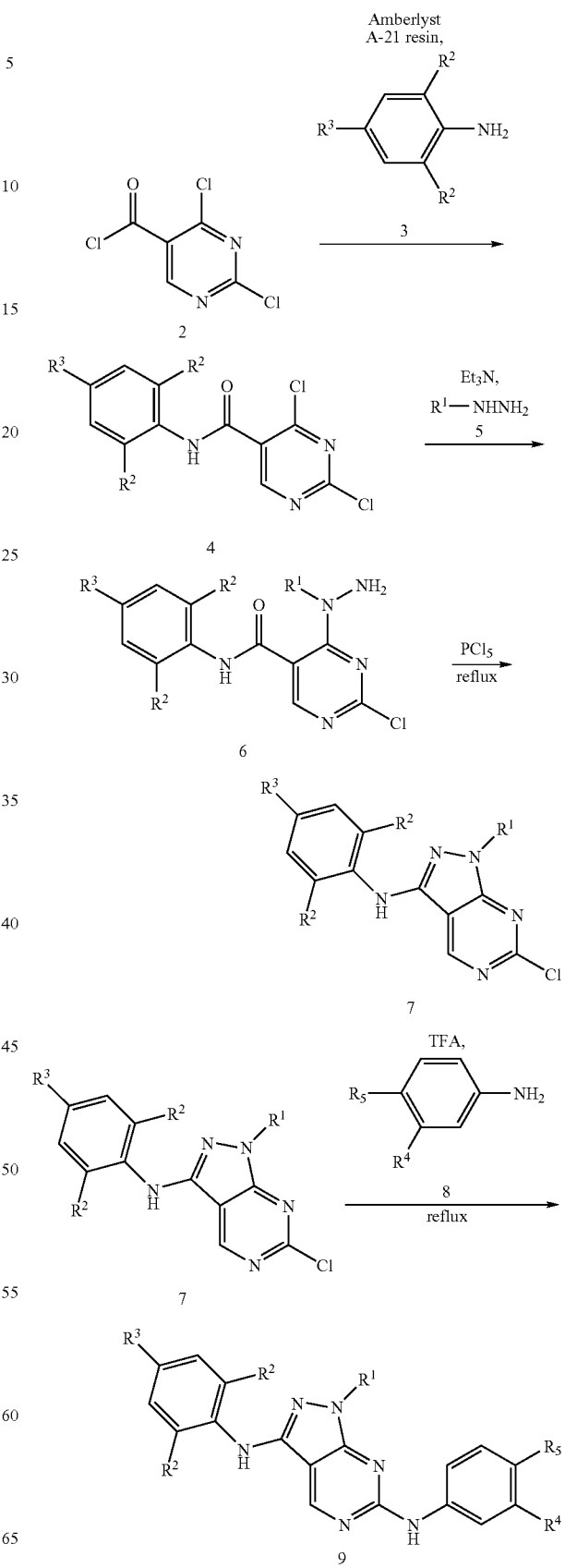

-continued

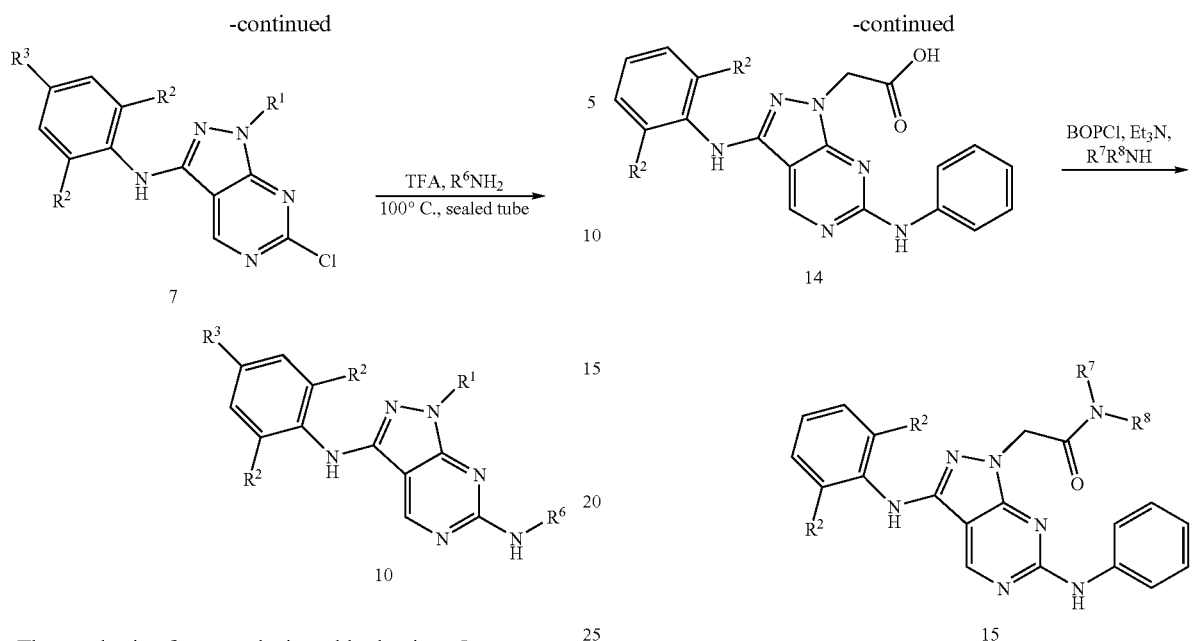

The synthesis of monosubstituted hydrazines 5, a precursor utilized in Scheme 1, is illustrated in Scheme 2. Condensation of commercially available hydrazine hydrate 11 with an alkylating agent 12, wherein LG indicates a leaving group such as a halogen atom, toluenesulfonate or methanesulfonate, in alcoholic solvent with heating followed by distillation provides 5 in a single step.

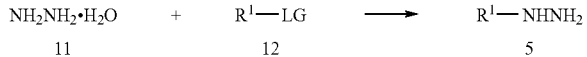

Schemes 3a-3d document the derivatization of a number of specific pyrazoles conforming to the general structure 9 (Scheme 1). All pyrazole precursors in Schemes 3a-3d were synthesized according to the general procedure illustrated in Scheme 1. As shown in Scheme 3a, hydrolysis of ester 13 with aqueous KOH or LiOH in a suitable organic solvent, such as THF or MeOH, affords acid 14. Standard amidation conditions, such as BOPCl/Et3N, DCC/DMAP, or EDC/HOBt, elicit the coupling of acid 14 with a primary or secondary amine to provide amide derivative 15. For derivatives 13-15, $R^2$ is a halide or alkyl group, and $R^7$-$R^8$ are alkyl or heteroalkyl substituents.

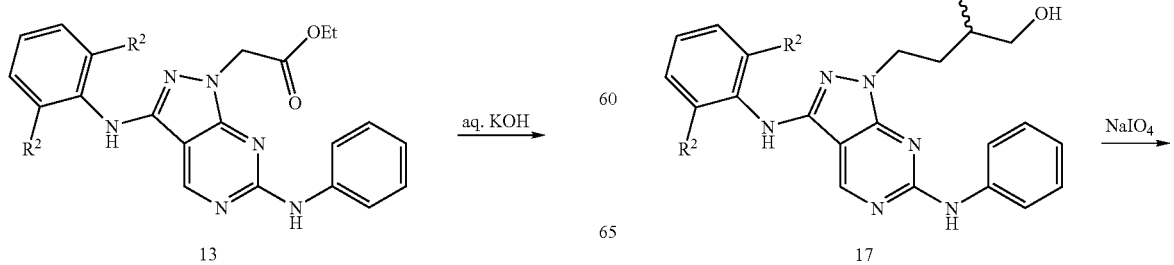

-continued

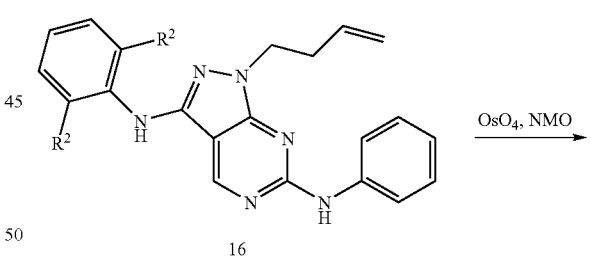

Schemes 3b-3c show the synthesis of a number of analogs derived from N-butenylpyrazole 16, where $R^2$ is a halide or alkyl group. In Scheme 3b, dihydroxylation of 16 affords diol 17, and 17 undergoes oxidative cleavage to aldehyde 18 by exposure to either $NaIO_4$ or $Pb(OAc)_4$. Reductive amination of 18 with acyclic or cyclic amines in the presence of an appropriate reducing agent, such as $NaBH(OAc)_3$ or $NaBH_3CN$, generates compounds of the structure 19, whereas reduction of 18 with an appropriate hydride donor, such as $NaBH_4$, $LiBH_4$, or DIBALH, gives alcohol 20.

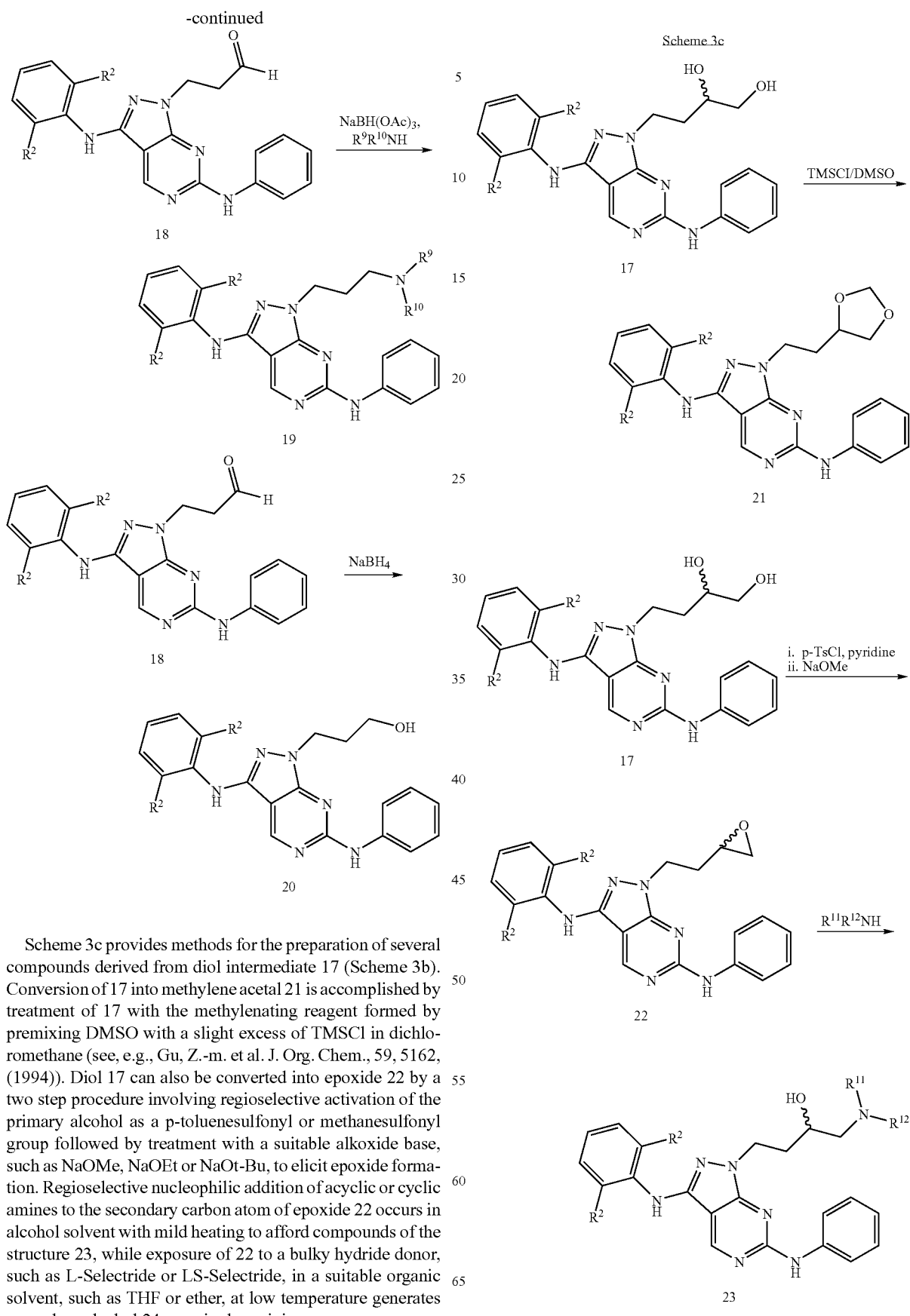

Scheme 3c provides methods for the preparation of several compounds derived from diol intermediate 17 (Scheme 3b). Conversion of 17 into methylene acetal 21 is accomplished by treatment of 17 with the methylenating reagent formed by premixing DMSO with a slight excess of TMSCl in dichloromethane (see, e.g., Gu, Z.-m. et al. J. Org. Chem., 59, 5162, (1994)). Diol 17 can also be converted into epoxide 22 by a two step procedure involving regioselective activation of the primary alcohol as a p-toluenesulfonyl or methanesulfonyl group followed by treatment with a suitable alkoxide base, such as NaOMe, NaOEt or NaOt-Bu, to elicit epoxide formation. Regioselective nucleophilic addition of acyclic or cyclic amines to the secondary carbon atom of epoxide 22 occurs in alcohol solvent with mild heating to afford compounds of the structure 23, while exposure of 22 to a bulky hydride donor, such as L-Selectride or LS-Selectride, in a suitable organic solvent, such as THF or ether, at low temperature generates secondary alcohol 24 as a single regioisomer.

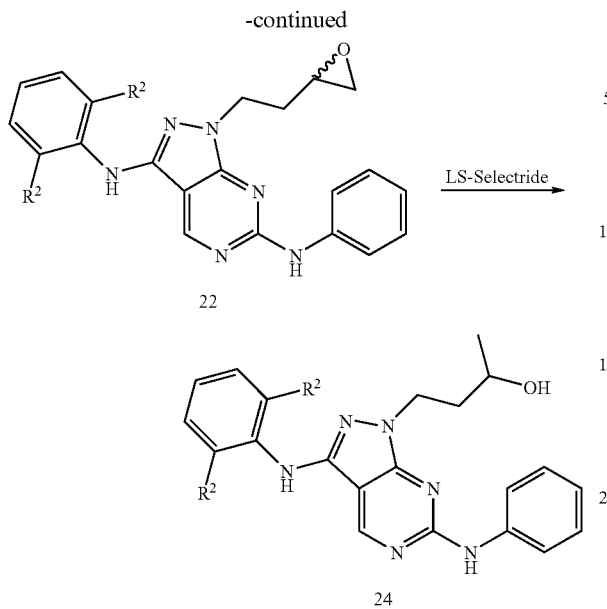

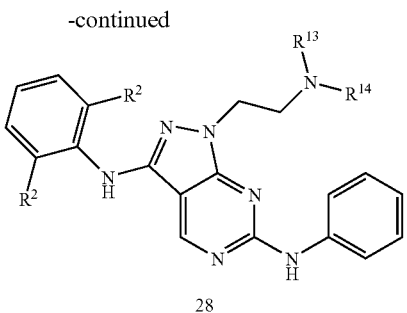

Several analogs were derived from N-allylpyrazole 25 as shown in Scheme 3d. For compound 25, $R^2$ is a halide or alkyl group. $OsO_4$-catalyzed dihydroxylation of 25 gives diol 26, and oxidative cleavage of 26 with either $NaIO_4$ or $Pb(OAc)_4$ provides aldehyde 27. Subsequent reductive amination of 27 with acyclic or cyclic amines in the presence of an appropriate reducing agent, such as $NaBH(OAc)_3$ or $NaBH_3CN$, generates compounds of the structure 28.

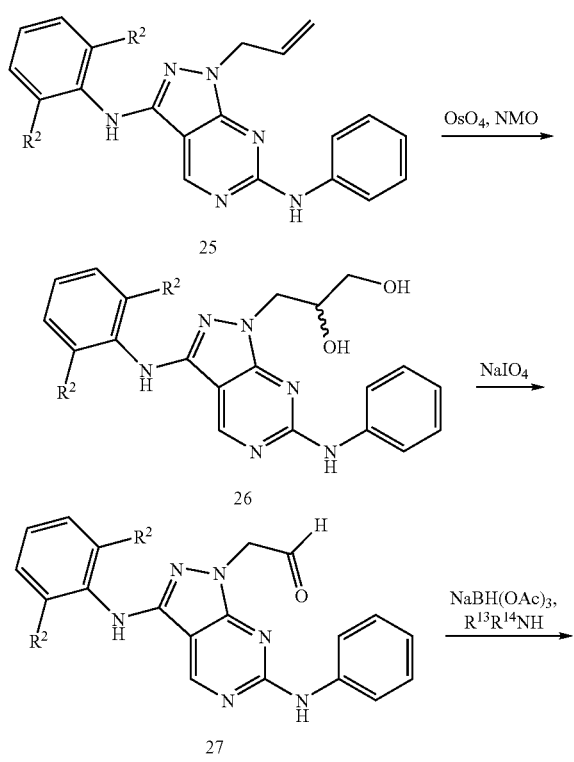

All process steps described herein can be carried out under known reaction conditions, such as under those specifically mentioned, in the absence of or usually in the presence of solvents or diluents, which can be inert to the reagents used and able to dissolve these, in the absence or presence of catalysts, condensing agents or neutralizing agents, for example ion exchangers, typically cation exchangers, for example in the protonated form, depending on the type of reaction and/or reactants at reduced, normal, or elevated temperature, for example in the range from about −100° C. to about 190° C., for example from about −80° C. to about 150° C., or, for another example, at about −80° C. to about 60° C., at RT, at about −20° C. to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing, for example, easier recovery of individual isomers.

The solvents from which those can be selected which are suitable for the reaction in question include, for example, water, esters, typically lower alkyl-lower alkanoates, e.g., EtOAc, ethers, typically aliphatic ethers, e.g., $Et_2O$, or cyclic ethers, e.g., THF, liquid aromatic hydrocarbons, typically benzene or toluene, alcohols, typically MeOH, EtOH, IPA or 1-propanol, nitrites, typically acetonitrile, halogenated hydrocarbons, typically $CH_2Cl_2$, acid amides, typically DMF, bases, typically heterocyclic nitrogen bases, e.g., pyridine, carboxylic acids, typically lower alkanecarboxylic acids, e.g., HOAc, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process.

The invention relates also to those forms of the process in which one starts from a compound obtainable at any stage as a transient species and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In one aspect, one starts from those starting materials which lead to the compounds described above. Starting materials of the invention are commercially available, or can be synthesized in analogy to or according to methods that are known in the art. In another aspect, new starting materials can be used and reaction conditions so selected as to enable the desired compounds to be obtained. In the preparation of starting materials, existing functional groups which do not participate in the reaction should, if necessary, be protected. Exemplary protecting groups, their introduction and their removal are described above or in the examples.

The compounds of Formulae I and II, including their salts, are also obtainable in the form of hydrates, or their crystals can include for example the solvent used for crystallization (present as solvates).

The following examples below, as do the schemes above, serve to illustrate various aspects of the invention. The schematic illustrations, detailed description of the methods and preparation of compounds of Formulae I and II, as well as the examples below and compounds described above fall within the scope, and serve to exemplify the scope of compounds contemplated in the invention. These detailed method descriptions are presented for illustrative purposes only and are not intended as a restriction on the scope of the present invention.

Example 1

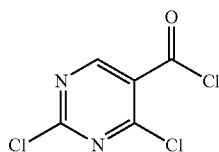

29

Step A. Synthesis of 2,4-dichloropyrimidine-5-carbonyl chloride 29

A suspension of 17.0 g (106 mmol) of 2,4-dihydroxypyrimidine-5-carboxylic acid hydrate and 81.1 g (370 mmol) of phosphorus pentachloride in 78 mL phosphorus oxychloride was heated at reflux for 16 h. The excess phosphorus oxychloride was removed by distillation and the residue was filtered. The filtered solids were rinsed with ethyl acetate and the filtrate was concentrated to give the title compound, which was used without further purification. $^1$H-NMR (CDCl13) δ 9.25 (s, 1H).

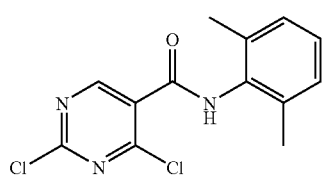

30

Step B. Synthesis of 2,4-dichloro-N-(2,6-dimethylphenyl)pyrimidine-5-carboxamide 30

To a mixture of 20.3 g (96 mmol) of 2,4-dichloropyrimidine-5-carbonyl chloride 29 and Amberlyst A21 (2.1 g) in 400 mL of EtOAc was added dropwise 11.7 mL of 2,6-dimethylaniline (95 mmol) at room temperature. The resulting mixture was heated to 50° C. for 12 h, and then was filtered. The filtrate was washed sequentially with water (200 mL), 1N HCl (50 mL), 1N NaOH (50 mL), and brine (100 mL). The combined organic layers were dried over Na$_2$SO$_4$, filtered, and the filtrate was washed with a small amount of DCM to give the title compound as a white solid. Mass Spectrum (ESI) m/e=297.1 (M+1).

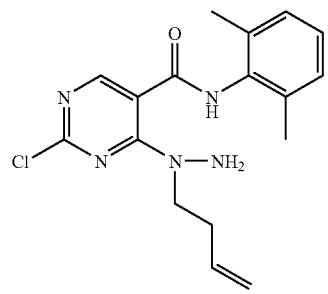

31

Step C. Synthesis of 4-(1-(but-3-enyl)hydrazinyl)-2-chloro-N-(2,6-dimethylphenyl)pyrimidine-5-carboxamide 31

A solution of 1.3 g (14.9 mmol) of 3-butenylhydrazine in 60 mL of THF was cooled to 0° C. and treated sequentially with 4.0 g (13.5 mmol) of 2,4-dichloro-N-(2,6-dimethylphenyl)pyrimidine-5-carboxamide 30 (Example 1, Step B) and 2.1 mL (14.9 mmol) of triethylamine. The resulting yellow slurry was warmed to room temperature and stirred for 23 h. The reaction mixture was quenched with saturated aqueous ammonium chloride (75 mL) and extracted with CH$_2$Cl$_2$ (3×100 mL). The combined organic layers were dried over Na$_2$SO$_4$, filtered, and the filtrate was purified by chromatography on silica gel (eluens CH$_2$Cl$_2$:MeOH, 17:3) to give the title compound. $^1$H-NMR (DMSO-d$_6$) δ 2.24 (s, 6H), 2.40-2.48 (m, 2H), 3.32 (s, 2H), 3.80 (t, J=7.3 Hz, 2H), 5.03 (dd, J=10.3 Hz, 1.1 Hz, 1H), 5.13 (dd, J=17.2 Hz, 1.5 Hz, 1H), 5.75-5.86 (m, 1H), 7.07 (s, 3H), 8.15 (s, 1H), 9.61 (s, 1H). Mass Spectrum (ESI) m/e=346.1 (M+1).

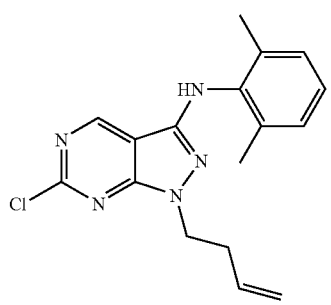

32

Step D. Synthesis of 1-(but-3-enyl)-6-chloro-N-(2,6-dimethylphenyl)-1H-pyrazolo[3,4-d]pyrimidin-3-amine 32

A mixture of 3.42 g (9.9 mmol) of 4-(1-(but-3-enyl)hydrazinyl)-2-chloro-N-(2,6-dimethylphenyl)pyrimidine-5-carboxamide 31 (Example 1, Step C) in 100 mL of toluene was treated with 2.16 g (95%, 9.9 mmol) of phosphorus pentachloride. The resulting orange slurry was heated at 100° C. for 1.75 h, and then was concentrated. The residue was dissolved in CH$_2$Cl$_2$ (250 mL) and washed with saturated aqueous sodium bicarbonate (150 mL). The aqueous layer was extracted with more CH$_2$Cl$_2$ (100 mL). The combined organic layers were dried over Na$_2$SO$_4$, filtered, and the filtrate was purified by chromatography on silica gel (hexanes: EtOAc, 4:1) to give the title compound 32. $^1$H-NMR (CDCl$_3$) δ 2.24 (s, 6H), 2.62-2.68 (m, 2H), 4.31 (t, J=7.2 Hz, 2H), 4.99 (dd, J=10.2 Hz, 1.6 Hz, 1H), 5.05 (dd, J=17.1 Hz, 1.6 Hz, 1H), 5.72-5.83 (m, 1H), 6.06 (s, 1H), 7.13-7.22 (m, 3H), 7.58 (s, 1H). Mass Spectrum (ESI) m/e=328.1 (M+1).

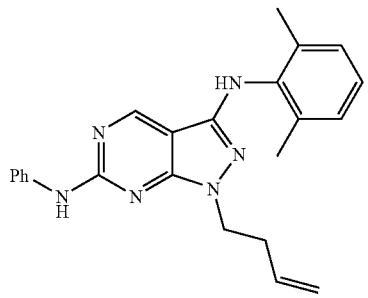

33

Step E. Synthesis of 1-(but-3-enyl)-N$^3$-(2,6-dimethylphenyl)-N$^6$-phenyl-1H-pyrazolo[3,4-d]pyrimidine-3,6-diamine 33

A solution of 815 mg (2.5 mmol) of 1-(but-3-enyl)-6-chloro-N-(2,6-dimethylphenyl)-1H-pyrazolo[3,4-d]pyrimidin-3-amine 32 (Example 1, Step D) in 17 mL of 1,4-dioxane was treated sequentially with 280 μl (3.1 mmol) of aniline and 415 μl (5.6 mmol) of TFA. The resulting orange solution was heated at reflux for 6 h, and then was concentrated. The residue was purified by chromatography on silica gel (hexanes:EtOAc, 3:1) to give the title compound 33. $^1$H-NMR (DMSO-d$_6$) δ 2.24 (s, 6H), 2.45-2.52 (m, 2H), 4.08 (t, J=6.8 Hz, 2H), 4.94 (d, J=10.2 Hz, 1.1 Hz, 1H), 5.02 (dd, J=17.2 Hz, 1.6 Hz, 1H), 5.78-5.88 (m, 1H), 6.95 (t, J=7.3 Hz, 1H), 7.06-7.14 (m, 3H), 7.28 (t, J=8.0 Hz, 2H), 7.84 (d, J=8.0 Hz, 2H), 8.10 (s, 1H), 8.39 (s, 1H), 9.66 (s, 1H). Mass Spectrum (ESI) m/e=385.2 (M+1).

Example 2

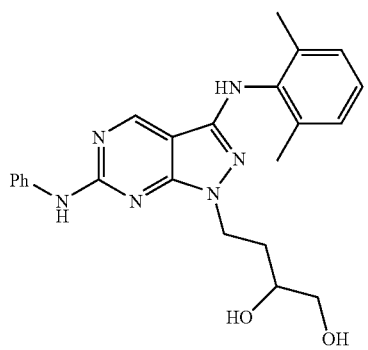

34

Step A. Synthesis of 4-(3-(2,6-dimethylphenylamino)-6-(phenylamino)-1H-pyrazolo[3,4-d]pyrimidin-1-yl)butane-1,2-diol 34

A mixture of 363 mg (0.9 mmol) of 1-(but-3-enyl)-N$^3$-(2,6-dimethylphenyl)-N$^6$-phenyl-1H-pyrazolo[3,4-d]pyrimidine-3,6-diamine 33 (Example 1, Step D) and a catalytic amount of OsO$_4$ in 28.5 mL acetone and 10 mL water was treated with 400 mg (97%, 3.3 mmol) of morpholine-N-oxide. The resulting yellow solution was stirred at room temperature for 18 h. The reaction mixture was diluted with water (95 mL) and extracted with CH$_2$Cl$_2$ (3×240 mL). The combined organic layers were dried over Na$_2$SO$_4$, filtered, and the filtrate was purified by chromatography on silica gel (eluens CH$_2$Cl$_2$:MeOH, 96:4) to give the title compound. $^1$H-NMR (DMSO-d$_6$) δ 1.58-1.69 (m, 1H), 1.91-2.01 (m, 1H), 2.20 (s, 6H), 3.19-3.27 (m, 1H), 3.28-3.36 (m, 1H), 3.88-3.97 (m, 1H), 4.05-4.19 (m, 2H), 4.48 (t, J=5.7 Hz, 1H), 4.56 (d, J=5.0 Hz, 1H), 6.94 (t, J=7.3 Hz, 1H), 7.05-7.14 (m, 3H), 7.27 (t, J=7.9 Hz, 2H), 7.85 (d, J=8.0 Hz, 2H), 8.08 (s, 1H), 8.36 (s, 1H), 9.65 (s, 1H). Mass Spectrum (ESI) m/e=419.2 (M+1).

Example 3

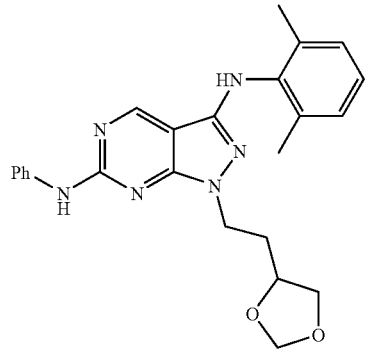

35

Step A. Synthesis of 1-(2-(1,3-dioxolan-4-yl)ethyl)-N$^3$-(2,6-dimethylphenyl)-N$^6$-phenyl-1H-pyrazolo[3,4-d]pyrimidine-3,6-diamine 35

A solution of 375 μl (2.9 mmol) of TMSCl in 2 mL CH$_2$Cl$_2$ was treated with 150 μl (2.1 mmol) of DMSO. The resulting colorless solution was stirred at room temperature for 1.25 h, during which time a white precipitate formed. The CH$_2$Cl$_2$ was decanted off and the white solid was rinsed with additional CH$_2$Cl$_2$ (1 mL). To this solid was added a solution of 14.3 mg (0.03 mmol) of 4-(3-(2,6-dimethylphenylamino)-6-(phenylamino)-1H-pyrazolo[3,4-d]pyrimidin-1-yl)butane-1,2-diol 34 (Example 2) in 2 mL of CH$_2$Cl$_2$. The resulting yellow slurry was stirred at room temperature for 9 d. The reaction mixture was quenched with a mixture of saturated aqueous sodium bicarbonate (5 mL) and water (5 mL) and was extracted with CH$_2$Cl$_2$ (10 mL). The organic layer was dried over Na$_2$SO$_4$ and filtered, and the filtrate was purified by HPLC (Capcell Pak C$_{18}$ 5 μm, gradient of 70% A:30% B to 20% A:80% B over 45 min; A=0.5% TFA in water, B=0.5% TFA in acetonitrile) to give the title compound. $^1$H-NMR (CD$_3$OD) δ 2.03-2.10 (m, 2H), 2.27 (s, 6H), 3.44 (dd, J=7.6 Hz, 6.6 Hz, 1H), 3.90 (t, J=7.2 Hz, 1H), 3.94-4.04 (m, 1H), 4.18-4.29 (m, 2H), 4.88 (s, 2H), 7.12 (t, J=7.3 Hz, 1H), 7.14-7.19 (m, 3H), 7.37 (t, J=7.9 Hz, 2H), 7.70 (d, J=7.9 Hz, 2H), 8.16 (s, 1H). Mass Spectrum (ESI) m/e=431.2 (M+1).

Example 4

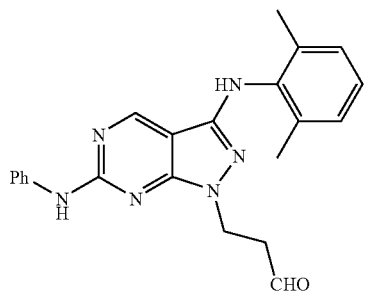

36

Step A. Synthesis of 3-(3-(2,6-dimethylphenylamino)-6-(phenylamino)-1H-pyrazolo[3,4-d]pyrimidin-1-yl)propanal 36

A solution of 114 mg (0.3 mmol) of 4-(3-(2,6-dimethylphenylamino)-6-(phenylamino)-1H-pyrazolo[3,4-d]pyrimidin-1-yl)butane-1,2-diol 34 (Example 2) in 10 mL of acetone and 7 mL of water was treated with 585 mg (2.7 mmol) of NaIO$_4$. The resulting tan slurry was stirred at room temperature for 6 h. The reaction mixture was diluted with CH$_2$Cl$_2$, filtered, and the filtrate was concentrated. The residue was dissolved in CH$_2$Cl$_2$ (75 mL) and washed with water (50 mL). The aqueous layer was extracted with more CH$_2$Cl$_2$ (2×75 mL). The combined organic layers were dried over Na$_2$SO$_4$ and filtered, and the filtrate was concentrated to give the title compound 36, which was used without further purification. $^1$H-NMR (CDCl$_3$) δ 2.27 (s, 6H), 3.05 (t, J=6.7 Hz, 2H), 4.52 (t, J=6.7 Hz, 2H), 5.30 (s, 1H), 5.89 (s, 1H), 7.06 (t, J=7.6 Hz, 1H), 7.13-7.19 (m, 3H), 7.34 (t, J=7.7 Hz, 2H), 7.42 (s, 1H), 7.64 (d, J=7.7 Hz, 2H), 9.89 (s, 1H). Mass Spectrum (ESI) m/e=387.2 (M+1).

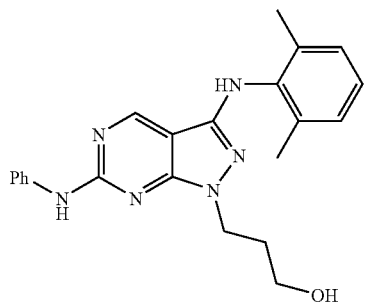

37

Step B. Synthesis of 3-(3-(2,6-dimethylphenylamino)-6-(phenylamino)-1H-pyrazolo[3,4-d]pyrimidin-1-yl)propan-1-ol 37

A slurry of 27 mg (0.07 mmol) of crude 3-(3-(2,6-dimethylphenylamino)-6-(phenylamino)-1H-pyrazolo[3,4-d]pyrimidin-1-yl)propanal 36 (Example 4, Step A) in 4 mL of absolute ethanol was treated with 17 mg (0.4 mmol) of NaBH$_4$. The resulting orange slurry was stirred at room temperature for 2 h. The reaction mixture was quenched with water (10 mL) and concentrated. The residue was extracted with CH$_2$Cl$_2$ (3×20 mL). The combined organic layers were dried over Na$_2$SO$_4$, filtered, and the filtrate was purified by chromatography on silica gel (eluens CH$_2$Cl$_2$:MeOH, 96:4) to give the title compound 37. 1H-NMR (CD3OD) δ1.96-2.04 (m, 2H), 2.26 (s, 6H), 3.54 (t, J=6.3 Hz, 2H), 4.20 (t, J=6.7 Hz, 2H), 6.99 (dt, J=7.4 Hz, 0.9 Hz, 1H), 7.09-7.17 (m, 3H), 7.30 (t, J=7.6 Hz, 2H), 7.75 (dd, J=8.6 Hz, 0.9 Hz, 2H), 8.09 (s, 1H). Mass Spectrum (ESI) m/e=389.2 (M+1).

Example 5

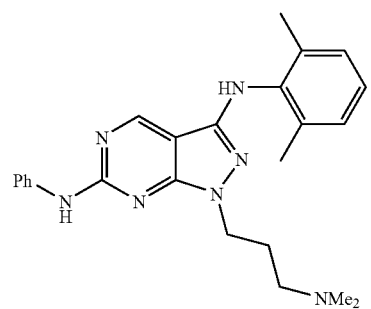

38

Step A. 1-(3-(Dimethylamino)propyl)-N$^3$-(2,6-dimethylphenyl)-N$^6$-phenyl-1H-pyrazolo[3,4-d]pyrimidine-3,6-diamine 38

A solution of 66 mg (0.2 mmol) of crude 3-(3-(2,6-dimethylphenylamino)-6-(phenylamino)-1H-pyrazolo[3,4-d]pyrimidin-1-yl)propanal 36 (Example 4, Step A) and 28 mg (0.3 mmol) of dimethylamine•HCl in 7 mL of 1,2-dichloroethane was treated sequentially with 60 mg (95%, 0.3 mmol) of NaBH(OAc)$_3$ and 75 μl (0.5 mmol) of triethylamine. The resulting brown slurry was stirred at room temperature for 17 h. The reaction mixture was quenched with saturated aqueous sodium bicarbonate (15 mL) and extracted with EtOAc (3×30 mL). The combined organic layers were dried over Na$_2$SO$_4$, filtered, and the filtrate was purified by chromatography on silica gel (CH$_2$Cl$_2$:MeOH, 44:6 grading to CH$_2$Cl$_2$:MeOH, 4:1) to give the title compound 38. $^1$H-NMR (CD$_3$OD) δ 2.06-2.14 (m, 2H), 2.28 (s, 6H), 2.49 (s, 6H), 2.72 (t, J=7.3 Hz, 2H), 4.19 (t, J=6.3 Hz, 2H), 7.01 (t, J=7.4 Hz, 1H), 7.12-7.19 (m, 3H), 7.31 (t, J=8.0 Hz, 2H), 7.75 (dd, J=8.6 Hz, 0.9 Hz, 2H), 8.27 (s, 1H). Mass Spectrum (ESI) m/e=416.1 (M+1).

Example 6

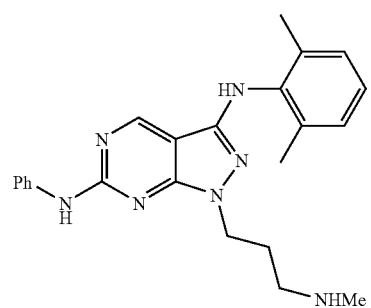

39

Step A. Synthesis of $N^3$-(2,6-dimethylphenyl)-1-(3-(methylamino)propyl)-$N^6$-phenyl-1H-pyrazolo[3,4-d]pyrimidine-3,6-diamine 39

A solution of 30 mg (0.08 mmol) of crude 3-(3-(2,6-dimethylphenylamino)-6-(phenylamino)-1H-pyrazolo[3,4-d]pyrimidin-1-yl)propanal 36 (Example 4, Step A) in 4 mL of THF was treated sequentially with and 80 µl (2.0 M, 0.2 mmol) of a THF solution of dimethylamine, 27 mg (95%, 0.1 mmol) of NaBH(OAc)$_3$ and 5 µl (0.08 mmol) of AcOH. The resulting green solution was stirred at room temperature for 23 h. The reaction mixture was quenched with saturated aqueous sodium bicarbonate (10 mL) and extracted with EtOAc (3×20 mL). The combined organic layers were dried over Na$_2$SO$_4$, filtered, and the filtrate was purified by HPLC (Capcell Pak C$_{18}$ 5 µm, gradient of 90% A: 10% B to 30% A:70% B over 45 min; A=0.5% TFA in water, B=0.5% TFA in acetonitrile) to give the title compound 39, which was converted directly to the tri-HCl salt. $^1$H-NMR (CD$_3$OD) δ 2.15-2.23 (m, 2H), 2.31 (s, 3H), 2.55 (s, 3H), 3.01-3.10 (m, 2H), 4.16-4.25 (m, 2H), 7.27 (t, J=7.1 Hz, 1H), 7.47 (t, J=7.0 Hz, 2H), 7.60-7.67 (m, 4H), 7.68-7.75 (m, 2H), 8.57 (s, 1H). Mass Spectrum (ESI) m/e=402.2 (M+1).

Example 7

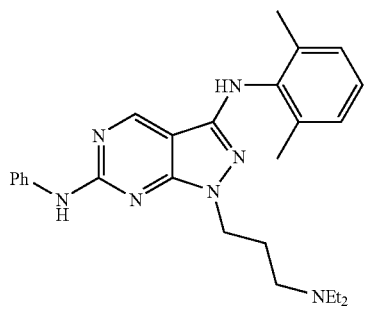

40

Synthesis of 1-(3-(diethylamino)propyl)-$N^3$-(2,6-dimethylphenyl)-$N^6$-phenyl-1H-pyrazolo[3,4-d]pyrimidine-3,6-diamine 40

The title compound 40 was prepared according to the procedure described in Example 5. $^1$H-NMR (CD$_3$OD) δ 1.16 (t, J=7.3 Hz, 6H), 2.11-2.22 (m, 2H), 2.27 (s, 6H), 2.94 (q, J=7.3 Hz, 4H), 3.03 (t, J=7.7 Hz, 2H), 4.21 (t, J=6.1 Hz, 2H), 7.02 (t, J=7.4 Hz, 1H), 7.12-7.19 (m, 3H), 7.32 (t, J=7.5 Hz, 2H), 7.75 (dd, J=8.7 Hz, 1.0 Hz, 2H), 8.15 (s, 1H). Mass Spectrum (ESI) m/e=444.1 (M+1).

Example 8

41

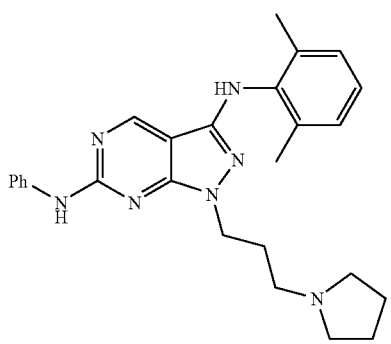

Synthesis of $N^3$-(2,6-dimethylphenyl)-$N^6$-phenyl-1-(3-(pyrrolidin-1-yl)propyl)-1H-pyrazolo[3,4-d]pyrimidine-3,6-diamine 41

The title compound 41 was prepared according to the procedure described in Example 5. $^1$H-NMR (CD$_3$OD) δ 1.87-1.93 (m, 4H), 2.14-2.22 (m, 2H), 2.28 (s, 6H), 2.99-3.08 (m, 6H), 4.21 (t, J=6.3 Hz, 2H), 7.03 (t, J=7.4 Hz, 1H), 7.12-7.18 (m, 3H), 7.32 (t, J=8.0 Hz, 2H), 7.75 (dd, J=8.6 Hz, 0.9 Hz, 2H), 8.26 (s, 1H). Mass Spectrum (ESI) m/e=442.3 (M+1).

Example 9

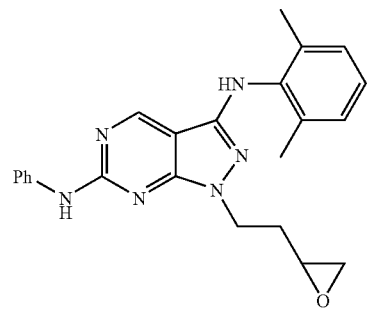

42

Step A. Synthesis of $N^3$-(2,6-dimethylphenyl)-1-(2-(oxiran-2-yl)ethyl)-$N^6$-phenyl-1H-pyrazolo[3,4-d]pyrimidine-3,6-diamine 42

A solution of 140 mg (0.3 mmol) of 4-(3-(2,6-dimethylphenylamino)-6-(phenylamino)-1H-pyrazolo[3,4-d]pyrimidin-1-yl)butane-1,2-diol 34 (Example 2) and 415 µl (5.1 mmol) of pyridine in 4 mL of CH$_2$Cl$_2$ was treated with 691 mg (3.6 mmol) of p-TsCl. The resulting brown solution was stirred at room temperature for 23.5 h. The reaction mixture was quenched with 1 N HCl (20 mL) and extracted with CH$_2$Cl$_2$ (2×20 mL). The combined organic layers were washed sequentially with water (20 mL), saturated aqueous sodium bicarbonate (20 mL) and brine (20 mL), then dried over Na$_2$SO$_4$ and filtered. The filtrate was purified by chromatography on silica gel (CH$_2$Cl$_2$:MeOH, 99:1) to give the mono-tosylate.

A solution of 180 mg (0.3 mmol) of the mono-tosylate in 4 mL CHCl$_3$ was cooled to 0° C. and treated with 110 µl (25 wt. %, 0.5 mmol) of a solution of NaOMe in MeOH. The resulting brown solution was stirred at 0° C. for 50 min. The reaction mixture was quenched with a mixture of saturated aqueous ammonium chloride (10 mL) and water (10 mL) and was extracted with CH$_2$Cl$_2$ (3×40 mL). The combined organic layers were dried over Na$_2$SO$_4$, filtered, and the filtrate was purified by chromatography on silica gel (CH$_2$Cl$_2$:MeOH, 99:1) to give the title compound 42. $^1$H-NMR (CDCl$_3$) δ 2.05-2.20 (m, 2H), 2.27 (s, 6H), 2.41-2.45 (m, 1H), 2.69 (t, J=4.5 Hz, 1H), 2.96-3.02 (m, 1H), 4.27-4.41 (m, 2H), 6.05 (s, 1H), 7.04 (t, J=7.3 Hz, 1H), 7.12-7.20 (m, 3H), 7.33 (t, J=7.8 Hz, 2H), 7.41 (s, 1H), 7.53 (s, 1H), 7.65 (d, J=8.2 Hz, 2H). Mass Spectrum (ESI) m/e=401.2 (M+1).

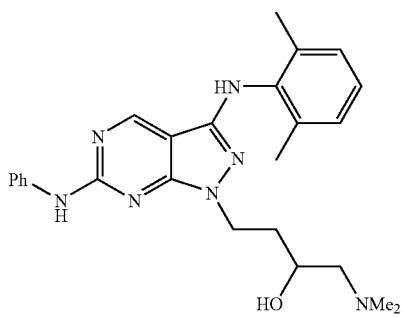

43

Step B. Synthesis of 1-(dimethylamino)-4-(3-(2,6-dimethylphenylamino)-6-(phenylamino)-1H-pyrazolo[3,4-d]pyrimidin-1-yl)butan-2-ol 43

A solution of 60 mg (0.15 mmol) of $N^3$-(2,6-dimethylphenyl)-1-(2-(oxiran-2-yl)ethyl)-$N^6$-phenyl-1H-pyrazolo[3,4-d]pyrimidine-3,6-diamine 42 (Example 9, Step A) in 4 mL of absolute ethanol was treated with 375 μl (2.0 M, 0.8 mmol) of a THF solution of dimethylamine. The resulting yellow solution was stirred at room temperature for 2.5 h and then heated to 40° C. for an additional 2 h. The reaction mixture was concentrated and the residue was purified by chromatography on silica gel (eluens $CH_2Cl_2$:MeOH, 19:1 grading to $CH_2Cl_2$:MeOH, 9:1) to give the title compound 43. $^1$H-NMR ($CD_3OD$) δ 1.75-1.84 (m, 1H), 1.95-2.05 (m, 1H), 2.19 (s, 6H), 2.26 (s, 6H), 2.27-2.43 (m, 2H), 3.63-3.70 (m, 1H), 4.17-4.31 (m, 2H), 7.00 (t, J=7.4 Hz, 1H), 7.09-7.16 (m, 3H), 7.30 (t, J=8.0 Hz, 2H), 7.75 (dd, J=8.7 Hz, 1.0 Hz, 2H), 8.10 (s, 1H). Mass Spectrum (ESI) m/e=446.2 (M+1).

Example 10

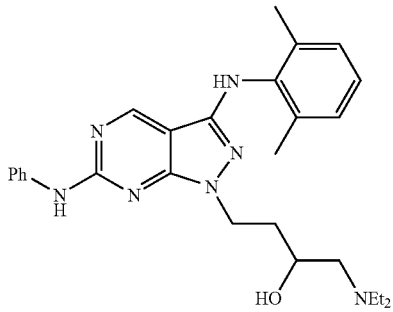

44

Synthesis of 1-(diethylamino)-4-(3-(2,6-dimethylphenylamino)-6-(phenylamino)-1H-pyrazolo[3,4-d]pyrimidin-1-yl)butan-2-ol 44

The title compound 44 was prepared according to the procedure described in Example 9. $^1$H-NMR ($CD_3OD$) δ 1.07-1.16 (m, 6H), 1.88-2.05 (m, 2H), 2.27 (s, 6H), 2.82-3.05 (m, 6H), 3.76-3.85 (m, 1H), 4.22-4.28 (m, 2H), 6.98-7.05 (m, 1H), 7.09-7.18 (m, 3H), 7.28-7.36 (m, 2H), 7.73-7.78 (m, 2H), 8.19 (s, 1H). Mass Spectrum (ESI) m/e=474.2 (M+1).

Example 11

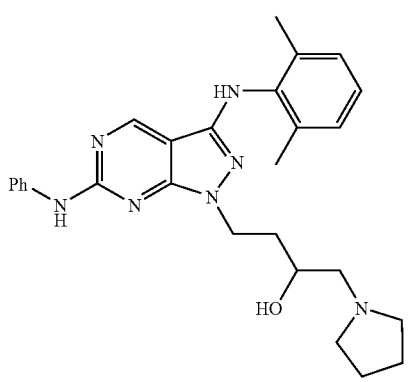

45

Synthesis of 4-(3-(2,6-dimethylphenylamino)-6-(phenylamino)-1H-pyrazolo[3,4-d]pyrimidin-1-yl)-1-(pyrrolidin-1-yl)butan-2-ol 45

The title compound was prepared according to the procedure described in Example 9. $^1$H-NMR ($CDCl_3$) δ 1.91-2.08 (m, 8H), 2.27 (s, 6H), 2.97-3.11 (m, 4H), 4.01-4.11 (m, 1H), 4.21-4.29 (m, 1H), 4.35-4.43 (m, 1H), 5.95 (s, 1H), 7.05 (t, J=7.4 Hz, 1H), 7.12-7.19 (m, 3H), 7.30-7.37 (m, 3H), 7.48 (s, 1H), 7.62 (d, J=8.0 Hz, 1.0 Hz, 2H). Mass Spectrum (ESI) m/e=472.3 (M+1).

Example 12

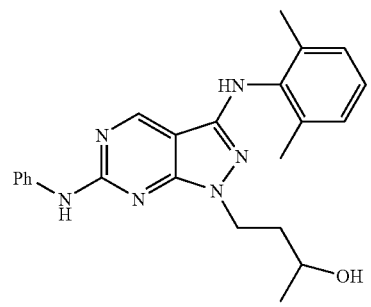

46

Synthesis of 4-(3-(2,6-dimethylphenylamino)-6-(phenylamino)-1H-pyrazolo[3,4-d]pyrimidin-1-yl)butan-2-ol 46

A solution of 9 mg (0.02 mmol) of $N^3$-(2,6-dimethylphenyl)-1-(2-(oxiran-2-yl)ethyl)-$N^6$-phenyl-1H-pyrazolo[3,4-d]pyrimidine-3,6-diamine 42 (Example 9, Step A) in 2.5 mL of $CH_2Cl_2$ was cooled to 0° C. and treated with 120 μl (1.0 M, 0.12 mmol) of a THF solution of LS-Selectride. The resulting tan solution was stirred at 0° C. for 1.25 h. The reaction mixture was quenched with saturated aqueous sodium potassium tartrate (8 mL) and stirred vigorously at room temperature overnight. The mixture was extracted with $CH_2Cl_2$ (10 mL), and the organic layer was dried over Na$_2$SO$_4$ and filtered. The filtrate was purified by chromatography on silica gel (eleuens CH$_2$Cl$_2$:MeOH, 98:2) to give the title compound 46. $^1$H-NMR (CD$_3$OD) δ 1.16 (d, J=6.3 Hz, 3H), 1.80-1.99 (m, 2H), 2.26 (s, 6H), 3.64-3.72 (m, 1H), 4.13-4.23 (m, 2H), 7.00 (t, J=7.4 Hz, 1H), 7.10-7.17 (m, 3H), 7.30 (t, J=8.0 Hz, 2H), 7.75 (d, J=7.7 Hz, 2H), 8.08 (s, 1H). Mass Spectrum (ESI) m/e=403.1 (M+1).

The following compounds (Table 1) were prepared as described in Example 1.

TABLE 1

| Example | Compound | R$^1$ | R$^2$ |
|---|---|---|---|
| 13 | 48 | phenyl | 4-(piperidin-1-yl)butyl |
| 14 | 49 | 4-(piperazin-1-yl)phenyl | 4-(piperidin-1-yl)butyl |
| 15 | 50 | 4-(4-methylpiperazin-1-yl)phenyl | 4-(piperidin-1-yl)butyl |
| 16 | 51 | phenyl | 3-(morpholin-4-yl)propyl |
| 17 | 52 | 4-(2-methoxyethoxy)phenyl | 3-(morpholin-4-yl)propyl |
| 18 | 53 | 4-(4-methylpiperazin-1-yl)phenyl | 3-(morpholin-4-yl)propyl |
| 19 | 54 | 4-(2-methoxyethoxy)phenyl | 3-methoxy-3-methylbutyl |
| 20 | 55 | 4-(4-methylpiperazin-1-yl)phenyl | 3-methoxy-3-methylbutyl |
| 21 | 56 | 4-(piperazin-1-yl)phenyl | 3-methoxy-3-methylbutyl |

TABLE 1-continued
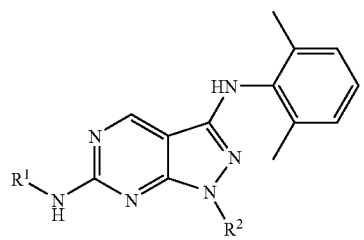
| Example | Compound | R¹ | R² |
|---|---|---|---|
| 22 | 57 | piperidine-N-(CH₂)₃-O-(3-F-phenyl)- | -(CH₂)₃-C(CH₃)₂-OMe |
| 23 | 58 | H₂N- | -(CH₂)₃-C(CH₃)₂-OMe |
| 24 | 59 | phenyl- | -(CH₂)₃-C(CH₃)₂-OMe |
| 25 | 60 | 3,5-dimethylpiperazin-1-yl-phenyl- | -(CH₂)₃-C(CH₃)₂-OMe |
| 26 | 61 | piperazin-1-yl-phenyl- | -CH₂-(tetrahydropyran-4-yl) |
| 27 | 62 | piperidine-N-(CH₂)₃-O-(3-F-phenyl)- | -CH₂-(tetrahydropyran-4-yl) |
| 28 | 63 | phenyl- | -CH₂-(tetrahydropyran-4-yl) |
| 29 | 64 | phenyl- | -CH₂-C(O)-O-ethyl |
| 30 | 65 | 4-F-phenyl- | -(CH₂)₄-(2-methoxymethyl-pyrrolidin-1-yl) |

TABLE 1-continued

| Example | Compound | R¹ | R² |
|---|---|---|---|
| 31 | 66 | phenyl | (2S)-2-(methoxymethyl)pyrrolidin-1-yl propyl |
| 32 | 67 | 4-(piperazin-1-yl)phenyl | (2S)-2-(methoxymethyl)pyrrolidin-1-yl propyl |
| 33 | 68 | H₂N– | (2S)-2-(methoxymethyl)pyrrolidin-1-yl propyl |

Example 13

$N^3$-(2,6-Dimethyl-phenyl)-$N^6$-phenyl-1-(3-piperidin-1-yl-propyl)-1H-pyrazolo[3,4-d]pyrimidine-3,6-diamine 48

$^1$H-NMR (CD$_3$OD) δ 8.36 (s, 1H), 7.72 (d, J=8.54 Hz, 2H), 7.37-7.41 (m, 2H), 7.18 (s, 2H), 7.12-7.16 (m, 2H), 4.22 (t, J=6.311 Hz, 2H), 3.39 (d, J=12 Hz, 2H), 3.13 (t, J=5.78 Hz, 2H), 2.81-2.88 (m, 2H), 2.30 (s, 6H), 2.22-2.27 (m, 2H), 1.85-1.89 (m, 2H), 1.76-1.80 (m, 1H), 1.62-1.71 (m, 2H), 1.45-1.48 (m, 1H). Mass spectrum (ESI) m/e=456.2 (M+1).

Example 14

$N^3$-(2,6-Dimethyl-phenyl)-$N^6$-(4-piperazin-1-yl-phenyl)-1-(3-piperidin-1-yl-propyl)-1H-pyrazolo[3,4-d]pyrimidine-3,6-diamine 49

$^1$H-NMR (CD$_3$OD) δ 8.33 (s, 1H), 7.61 (d, J=8.92 Hz, 2H), 7.17 (s, 3H), 7.08 (d, J=8.92 Hz, 2H), 4.20 (t, J=6.25 Hz, 2H), 3.40 (br, s, 10H), 3.14 (t, J=8.07 Hz, 2H), 2.81-2.87 (m, 2H), 2.29 (s, 6H), 2.23-2.27 (m, 2H), 1.65-1.89 (m, 5H), 1.48-1.51 (m, 1H). Mass Spectrum (ESI) m/e=540.4 (M+1).

Example 15

$N^3$-(2,6-Dimethyl-phenyl)-$N^6$-[4-(4-methyl-piperazin-1-yl)-phenyl]-1-(3-piperidin-1-yl-propyl)-1H-pyrazolo[3,4-d]pyrimidine-3,6-diamine 50

$^1$H-NMR (CD$_3$OD) δ 8.55 (s, 1H), 7.55 (d, J=8.77 Hz, 2H), 7.19 (d, J=8.67 Hz, 2H), 7.17 (s, 3H), 4.19 (t, J=6.30 Hz, 2H), 3.89 (d, J=13.2 Hz, 2H), 3.65 (d, J=11.67 Hz, 2H), 3.44 (d, J=11.72 Hz, 2H), 3.14-3.20 (m, 4H), 3.00 (s, 3H), 2.85 (t, J=12 Hz, 2H), 2.31 (s, 9H), 1.72-1.90 (m, 6H), 1.47-1.50 (m, 1H). Mass Spectrum (ESI) m/e=554.3 (M+1).

Example 16

$N^3$-(2,6-Dimethyl-phenyl)-1-(2-morpholin-4-yl-ethyl)-$N^6$-phenyl-1H-pyrazolo[3,4-d]pyrimidine-3,6-diamine 51

$^1$H-NMR (CD$_3$OD) δ 8.54 (s, 1H), 7.62 (d, J=8.44 Hz, 2H), 7.49 (t, J=8.42 Hz, 2H), 7.30 (t, J=7.43 Hz, 1H), 7.18 (s, 3H), 4.53 (t, J=5.54 Hz, 2H), 3.79 (t, J=12.05 Hz, 2H), 3.59 (t, J=5.34 Hz, 6H), 3.12 (t, J=11.16 Hz, 2H), 2.31 (s, 6H). Mass spectrum (ESI) m/e=444.2 (M+1).

Example 17

$N^3$-(2,6-Dimethyl-phenyl)-$N^6$-[4-(2-methoxy-ethoxy)-phenyl]-1-(2-morpholin-4-yl-ethyl)-1H-pyrazolo[3,4-d]pyrimidine-3,6-diamine 52

$^1$H-NMR (CD$_3$OD) δ 8.53 (s, 1H) 7.48 (d, J=8.94 Hz, 2H), 7.17 (s, 3H), 7.06 (d, J=6.87 Hz, 2H), 4.51 (t, J=5.55 Hz, 2H), 4.17 (t, J=4.63 Hz, 2H), 3.85 (d, J=10.41 Hz, 2H), 3.77 (t, J=4.51 Hz, 2H), 3.57-3.65 (m, 6H), 3.44 (s, 3H), 3.13 (t, J=12.08 Hz, 2H), 2.33 (s, 6H). Mass spectrum (ESI) m/e=518.2 (M+1).

Example 18

$N^3$-(2,6-dimethyl-phenyl)-$N^6$-[4-(4-methyl-piperazin-1-yl)-phenyl]-1-(2-morpholin-4-yl-ethyl)-1H-pyrazolo[3,4-d]pyrimidine-3,6-diamine 53

$^1$H-NMR (CD$_3$OD) δ 8.44 (s, 1H), 7.59 (d, J=8.41 Hz, 2H), 7.18 (s, 3H), 7.07 (d, J=8.49 Hz, 2H), 4.87 (br, s, 2H), 3.81 (br, s, 2H), 3.59-3.63 (m, 8H), 3.32 (m, 3H), 3.09 (m, 2H), 2.99 (s, 3H), 2.30 (s, 6H). Mass spectrum (ESI) m/e=542.3 (M+1).

Example 19

$N^3$-(2,6-Dimethyl-phenyl)-N-6-[4-(2-methoxy-ethoxy)-phenyl]-1-(3-methoxy-3-methyl-butyl)-1H-pyrazolo[3,4-d]pyrimidine-3,6-diamine 54

$^1$H-NMR (CD$_3$OD) δ 8.27 (s, 1H), 7.47 (d, J=8.94 Hz, 2H), 7.18 (s, 3H), 7.04 (d, J=9.01 Hz, 2H), 4.16 (t, J=4.64 Hz, 2H), 4.12 (t, J=7.74 Hz, 2H), 3.77 (t, J=4.52 Hz, 2H), 3.45 (s, 3H), 3.14 (s, 3H), 2.29 (s, 6H), 1.98 (t, J=7.67 Hz, 2H), 1.20 (s, 6H). Mass spectrum (ESI) m/e=505.3 (M+1).

Example 20

$N^3$-(2,6-Dimethyl-phenyl)-1-(3-methoxy-3-methyl-butyl)-N-6-[4-(methylpiperazin-1-yl)phenyl]-1H-pyrazolo[3,4-d]pyrimidine-3,6-diamine 55

$^1$H-NMR (CDCl$_3$) δ 1.25 (s, 6H), 2.05-2.09 (m, 2H), 2.27 (s, 6H), 2.45 (s, 3H), 2.70-2.90 (m, 4H), 3.20-3.30 (m, 7H), 4.21-4.25 (m, 2H), 5.84 (s, 1H), 6.90 (d, J=9.0 Hz, 2H), 6.99 (s, 1H), 7.10-7.15 (m, 3H), 7.35 (s, 1H), 7.56 (d, J=9.0 Hz, 2H). Mass Spectrum (ESI) m/e=529 (M+1).

Example 21

$N^3$-(2,6-Dimethyl-phenyl)-1-(3-methoxy-3-methyl-butyl)-$N^6$-(4-piperazin-1-yl-phenyl)-1H-pyrazolo[3,4-d]pyrimidine-3,6-diamine 56

$^1$H-NMR (CDCl$_3$) δ 1.22 (s, 6H), 2.04 (t, J=9.2 Hz, 2H), 2.26 (s, 6H), 3.00-3.10 (m, 8H), 3.25 (s, 3H), 4.21 (t, J=9.2 Hz, 2H), 6.08 (s, 1H), 6.89 (d, J=8.6 Hz, 2H), 7.10-7.15 (m, 3H), 7.27 (s, 1H), 7.36 (s, 1H), 7.55 (d, J=8.6 Hz, 2H). Mass Spectrum (ESI) m/e=515 (M+1).

Example 22

$N^3$-(2,6-Dimethylphenyl)-$N^6$-[3-fluoro-4-(3-(piperidin-1-yl)propoxy)phenyl 1-1-(3-methoxy-3-methyl-butyl)-1H-pyrazolo[3,4-d]pyrimidine-3,6-diamine 57

$^1$H-NMR (CDCl$_3$) δ 1.26 (s, 6H), 1.45-1.50 (m, 3H), 2.05-2.10 (m, 5H), 2.27 (s, 6H), 2.30-2.60 (m, 6H), 3.27 (s, 3H), 4.07 (t, J=6.3 Hz, 2H), 4.23-4.27 (m, 2H), 5.88 (s, 1H), 6.91 (t, J=9.0 Hz, 1H), 7.05 (d, J=8.9 Hz, 1H), 7.13 (s, 1H), 7.13-7.16 (m, 3H), 7.35 (s, 1H), 7.82 (d, J=9.0 Hz, 2H). Mass Spectrum (ESI) m/e=590 (M+1).

Example 23

$N^3$-(2,6-Dimethylphenyl)-1-(3-methoxy-3-methylbutyl)-1H-indazole-3,6-diamine 58

$^1$H-NMR (CDCl$_3$) δ 1.09 (s, 6H), 1.79-1.83 (m, 2H), 2.19 (S, 6H), 3.16 (s, 3H), 3.92-3.96 (m, 2H), 7.09-7.12 (m, 3H), 7.65 (s, 1H), 8.50 (s, 1H), 8.55 (s, 1H). Mass Spectrum (ESI) m/e=354 (M+1).

Example 24

$N^3$-(2,6-Dimethylphenyl)-1-(3-methoxy-3-methylbutyl))-$N^6$-phenyl-1H-indazole-3,6-diamine 59

$^1$H-NMR (CDCl$_3$) δ 1.24 (s, 6H), 2.03-2.05 (m, 2H), 2.27 (s, 6H), 3.20 (s, 3H), 4.21-4.22 (m, 2H), 5.30 (s, 1H), 6.52 (s, 1H), 7.16-7.21 (m, 3H), 7.33-7.37 (m, 2H), 7.71-7.73 (m, 2H), 10.64 (s, 1H). Mass Spectrum (ESI) m/e=503 (M+1).

Example 25

$N^3$-(2,6-Dimethylphenyl)-1-$N^6$-(4-(3,5-dimethylpiperazin-1-yl)phenyl)-1-(3-methoxy-3-methylbutyl)-1H-indazole-3,6-diamine 60

$^1$H-NMR (CDCl$_3$) δ 1.11 (s, 6H), 1.31 (s, 6H), 1.75-1.78 (m, 2H), 2.20 (s, 6H), 3.08-3.12 (m, 4H), 3.70-3.72 (m, 2H), 7.00-7.02 (m, 2H), 7.10-7.15 (m, 3H), 7.66-7.68 (m, 2H), 8.60 (s, 1H). Mass Spectrum (ESI) m/e=−542 (M+1).

Example 26

$N^3$-(2,6-Dimethylphenyl)-1-$N^6$-(4-piperazin-1-yl)phenyl)-1-((tetrahydro-2H-pyran-4-yl)methyl)-1H-indazole-3,6-diamine 61

$^1$H-NMR (CDCl$_3$) δ 1.45-1.65 (m, 4H), 2.20-2.27 (m, 7H), 3.05-3.18 (m, 6H), 3.37-3.43 (m, 2H), 3.81-3.90 (m, 2H), 3.97-4.04 (m, 2H), 4.12 (d, J=7.1 Hz, 2H), 5.80 (s, 1H), 6.92-6.99 (m, 2H), 7.15-7.21 (m, 3H), 7.40 (s, 1H), 7.50-7.56 (m, 2H). Mass Spectrum (ESI) m/e=513 (M+1).

Example 27

$N^3$-(2,6-Dimethylphenyl)-1-$N^6$-(3-fluoro-4-(piperidin-1-yl)propoxy)phenyl)-1-((tetrahydro-2H-pyran-4-yl)methyl)-1H-indazole-3,6-diamine 62

$^1$H-NMR (CDCl$_3$) δ 1.26-1.51 (m, 10H), 2.05-2.15 (m, 2H), 2.27 (s, 6H), 2.50-2.70 (m, 6H), 3.37-3.42 (m, 2H), 3.96-3.99 (m, 2H), 4.04 (d, J=7.0 Hz, 2H), 4.09 (t, J=6.1 Hz, 2H), 5.86 (s, 1H), 6.94 (t, J=9.0 Hz, 1H), 6.99 (s, 1H), 7.10 (d, J=8.7 Hz, 1H), 7.10-7.15 (m, 3H), 7.41 (s, 1H), 7.71 (dd, J=13.2, 2.4 Hz, 1H). Mass Spectrum (ESI) m/e=588 (M+1).

Example 28

$N^3$-(2,6-Dimethylphenyl)-$N^6$-phenyl-1-((tetrahydro-2H-pyran-4-yl)methyl)-1H-indazole-3,6-diamine 63

$^1$H-NMR (CDCl$_3$) δ 1.44-1.51 (m, 4H), 2.22-2.30 (m, 7H), 3.36-3.42 (m, 2H), 3.96-3.97 (m, 2H), 4.05 (d, J=7.1 Hz, 2H), 6.04 (s, 1H), 7.08 (t, J=7.4 Hz, 1 if), 7.15-7.19 (m, 3H), 7.35 (t, J=7.5 Hz, 2H), 7.41 (s, 1H), 7.67 (d, J=7.7 Hz, 2H), 7.82 (s, 1H). Mass Spectrum (ESI) m/e=429 (M+1).

Example 29

Ethyl-2-(3-(2,6-dimethylphenylamino)-6-(phenylamino)-1H-indazole-1-yl)acetate 64

$^1$H-NMR (CDCl$_3$) δ 1.28 (t, J=7.1 Hz, 3H), 2.29 (s, 6H), 4.24 (q, J=7.1 Hz, 2H), 4.91 (s, 2H), 5.97 (s, 1H), 7.07 (t, J=7.4 Hz, 1H), 7.15-7.20 (m, 3H), 7.33 (t, J=7.5 Hz, 2H), 7.46 (s, 1H), 7.61 (d, J=7.6 Hz, 2H), 7.72 (s, 1H). Mass Spectrum (ESI) m/e=417 (M+1).

Example 30

(R)—$N^3$-(2,6-Dimethylphenyl)-$N^6$-(4-fluorophenyl)-1-(3-(2-(methoxymethyl)pyrrolidin-1-yl)propyl)-1H-indazole-3,6-diamine 65

$^1$H-NMR (DMSO-d$^6$) δ 1.50-2.15 (m, 6H), 2.35 (s, 6H), 2.80-2.90 (m, 1H), 3.15-3.20 (m, 2H), 3.23 (s, 3H), 4.16-4.21

(m, 6H), 7.16-7.23 (m, 5H), 8.00-8.12 (m, 2H), 8.15 (s, 1H), 8.46 (s, 1H), 9.70 (s, 1H). Mass Spectrum (ESI) m/e=504 (M+1).

Example 31

(R)—$N^3$-(2,6-Dimethylphenyl)-1-(3-(2-(methoxymethyl)pyrrolidin-1-yl)propyl)-$N^6$-phenyl-1H-indazole-3,6-diamine 66

$^1$H-NMR (CD$_3$OD) δ 1.76-2.19 (m, 6H), 2.29 (s, 6H), 3.05-3.25 (m, 2H), 3.31 (s, 3H) 3.43-3.53 (m, 2H), 3.53-3.61 (m, 2H), 4.13-4.22 (d, J=8 Hz, 2H), 7.18 (s, 3H), 7.25-7.28 (t, J=8 Hz, 1H), 7.43-7.47 (m, 2H), 7.60-7.62 (m, 2H), 8.46 (s, 1H). Mass Spectrum (ESI) m/e=–485 (M+1).

Example 32

(R)—$N^3$-(2,6-Dimethylphenyl)-1-(3-(2-(methoxymethyl)pyrrolidin-1-yl)propyl)-$N^6$-(4-piperazin-1-yl)phenyl-1H-indazole-3,6-diamine 67

$^1$H-NMR (CD$_3$OD) δ 1.78-2.03 (m, 6H), 2.29 (s, 6H), 3.02-3.09 (m, 2H), 3.34 (s, 3H), 3.42-3.59 (m, 10H), 3.59-3.61 (m, 2H), 4.17 (m, 2H), 7.17-7.19 (m, 5H), 7.52-7.54 (m, 2H), 8.49 (s, 1H). Mass Spectrum (ESI) m/e=–569 (M+1).

Example 33

(R)—$N^3$-(2,6-Dimethylphenyl)-1-(3-(2-(methoxymethyl)pyrrolidin-1-yl)propyl)-1H-indazole-3,6-diamine 68

$^1$H-NMR (CD$_3$OD) δ 1.70-2.25 (m, 6H), 2.30 (s, 6H), 3.02-3.20 (m, 2H), 3.31 (s, 3H), 3.33-3.37 (m, 2H), 3.63-3.65 (m, 2H), 4.13-4.20 (m, 2H), 7.18 (m, 3H), 8.50 (s, 1H). Mass Spectrum (ESI) m/e=–446 (M+1).

Example 34

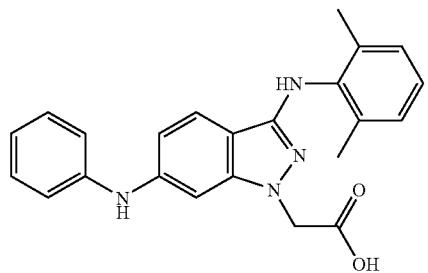

69

Synthesis of 2-(3-(2,6-dimethylphenylamino)-6-(phenylamino)-1H-indazol-1-yl)acetic acid 69

To a stirred solution of 300 mg (0.72 mmol) of ethyl 2-(3-(2,6-dimethylphenylamino)-6-(phenylamino)-1H-indazol-1-yl)acetate 64 (Example 29) in MeOH (10 mL) was added 1 N NaOH solution (4 mL, 4 mmol). The mixture was stirred at room temperature for 8 hours before being concentrated under reduced pressure. The residue was extracted with DCM (5 mL×2) and neutralized with 3 N HCl solution to pH 2. The resulting yellow solid was filtered, washed with water and dried to give the title compound. $^1$H-NMR (DMSO-d$^6$) δ 2.20 (s, 6H), 4.74 (s, 2H), 6.96 (t, J=7.2 Hz, 1H), 7.05-7.09 (m, 3H), 7.28 (t, J=7.7 Hz, 2H), 7.79 (d, J=7.9 Hz, 2H), 8.22 (s, 1H), 8.53 (s, 1H), 9.77 (s, 1H). Mass Spectrum (ESI) m/e=389 (M+1).

Example 35

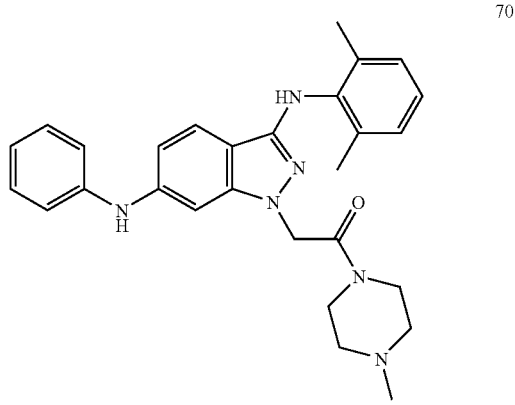

70

Synthesis of 2-(3-(2,6-dimethylphenylamino)-6-(phenylamino)-1H-indazol-1-yl)-1-(4-methylpiperazin-1-yl)ethanone 70

A solution of 100 mg (0.26 mmol) of 2-(3-(2,6-dimethylphenylamino)-6-(phenylamino)-1H-indazol-1-yl)acetic acid 69 (Example 34) in DCM (10 mL) at room temperature was treated with Et$_3$N (43 μL, 1.2 eq) followed with Bop-Cl (73 mg, 1.1 eq) and 1-methylpiperazine (35 μL, 1.2 eq). The mixture was stirred at room temperature for 3 hours before it was quenched with water (5 mL). The organic layer was separated and washed with water, brine, dried over sodium sulfate and filtered. The filtrate was concentrated and purified by column chromatography on silica gel (eluens: DCM:MeOH:NH$_4$OH, 20:1:0.2) to give the title compound 70. $^1$H-NMR (CDCl$_3$) δ 2.28 (s, 6H), 2.32 (s, 3H), 2.35-2.45 (m, 4H), 3.59-3.69 (m, 4H), 4.98 (s, 2H), 5.91 (s, 1H), 7.04 (t, J=7.3 Hz, 1H), 7.08-7.16 (m, 3H), 7.19 (s, 1H), 7.32 (t, J=8.4 Hz, 2H), 7.47 (s, 1H), 7.58 (d, J=7.7 Hz, 2H). Mass Spectrum (ESI) m/e=471 (M+1).

Example 36

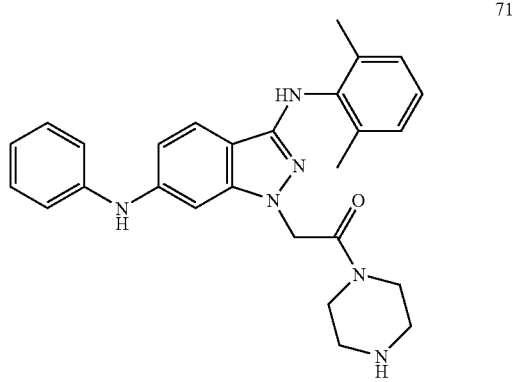

71

Synthesis of 2-(3-(2,6-dimethylphenylamino)-6-(phenylamino)-1H-indazol-1-yl)-1-(piperazin-1-yl)ethanone 71

The title compound was prepared from 2-(3-(2,6-dimethylphenylamino)-6-(phenylamino)-1H-indazol-1-yl)acetic acid 69 (Example 34) as described in Example 35. ¹H-NMR (DMSO-d⁶) δ 2.20 (s, 6H), 3.03-3.75 (m, 8H), 5.02 (s, 2H), 6.98-7.10 (m, 4H), 7.35-7.45 (m, 2H), 7.77-7.78 (m, 2H), 8.30 (s, 1H), 8.69 (s, 1H), 9.23 (s, 2H), 9.87 (s, 1H). Mass Spectrum (ESI) m/e=457 (M+1).

Example 37

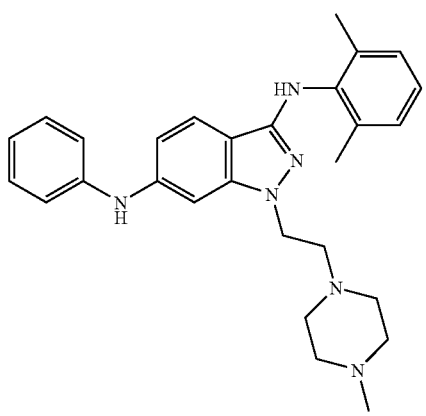

Synthesis of N³-(2,6-dimethylphenyl)-1-(2-(4-methylpiperazin-1-yl)ethyl)-N⁶-phenyl-1H-indazole-3,6-diamine 72

To a solution of 55 mg, (0.12 mmol) of 2-(3-(2,6-dimethylphenylamino)-6-(phenylamino)-1H-indazol-1-yl)-1-(4-methylpiperazin-1-yl)ethanone 70 (Example 35) in THF (2 mL) at room temperature was added LiAlH₄ in THF (1 M, 0.23 mL, 2 eq) dropwise. The reaction mixture was then stirred at this temperature for 2 hours before being quenched with EtOAc (0.5 mL), 1 N NaOH (0.5 mL) and water (0.5 mL) sequentially. The resulting mixture was stirred for 10 minutes before MgSO₄ (50 mg) was added. The suspension was stirred further for 10 minutes and filtered. The filtrate was concentrated and purified by HPLC (Capcell Pak C₁₈ column, gradient of 10% A: 90% B to 90% A: 10% B over 45 minutes; A=0.1% TFA in water, B=0.1% TFA in MeCN) to give a yellow solid 72. ¹H-NMR (DMSO-d⁶) δ 2.23 (s, 6H), 2.77 (s, 3H), 3.23-3.75 (m, 8H), 4.45 (s, 2H), 7.05 (t, J=8.5 Hz, 1H), 7.11-7.13 (m, 3H), 7.38 (t, J=8.5 Hz, 2H), 7.82 (d, J=8.8 Hz, 2H), 8.55 (s, 1H), 8.60 (s, 1H), 10.15 (s, 1H). Mass Spectrum (ESI) m/e=457 (M+1).

By modifying Example 1, Step B and replacing 2,6-dimethylaniline with the appropriately substituted aniline, the following examples of Table 2 were prepared:

TABLE 2

73

| Example | Compound | R¹ | R² |
|---|---|---|---|
| 38 | 74 | phenyl | phenyl |
| 39 | 75 | 4-(4-methylpiperazin-1-yl)phenyl | phenyl |
| 40 | 76 | phenyl | 2,4,6-trimethylphenyl |

TABLE 2-continued

| Example | Compound | R¹ | R² |
|---|---|---|---|
| 41 | 77 | 4-(4-methylpiperazin-1-yl)phenyl | 2,4,6-trimethylphenyl |
| 42 | 78 | phenyl | 4-fluoro-2,6-dimethylphenyl |
| 43 | 79 | 4-(4-methylpiperazin-1-yl)phenyl | 4-fluoro-2,6-dimethylphenyl |
| 44 | 80 | phenyl | 2,6-dichlorophenyl |
| 45 | 81 | 4-(4-Fmoc-piperazin-1-yl)phenyl | 2,6-dichlorophenyl |
| 46 | 82 | 3-fluoro-4-(2-(pyrrolidin-1-yl)ethoxy)phenyl | 2,6-dichlorophenyl |
| 47 | 83 | CH₃ | 2,6-dichlorophenyl |

TABLE 2-continued

| Example | Compound | R¹ | R² |
|---|---|---|---|
| 48 | 84 | 4-(piperazin-1-yl)phenyl | 2,6-dichlorophenyl |

Example 38

1-(3-Methoxy-3-methyl-butyl)-$N^3$, $N^6$-diphenyl-1H-pyrazolo[3,4-d]pyrimidine-3,6-diamine 74

$^1$H-NMR(CD$_3$OD) δ 8.88 (s, 1H), 7.74 (d, J=8.71 Hz, 2H), 7.66 (d, J=8.59 Hz, 2H), 7.41 (t, J=8.51 Hz, 2H), 7.33 (t, J=8.61 Hz, 2H), 7.18 (t, J=7.4 Hz, 1H), 6.98 (t, J=7.38 Hz, 1H), 4.30 (t, J=7.81 Hz, 2H), 3.24 (s, 3H), 2.13 (t, J=7.75 Hz, 2H), 1.28 (s, 6H). Mass spectrum (ESI) m/e=403.1 (M+1).

Example 39

1-(3-Methoxy-3-methyl-butyl)-$N^6$-[4-(4-methyl-piperazin-1-yl)-phenyl-$N^3$-phenyl-1H-pyrazolo[3,4-d]pyrimidine-3,6-diamine 75

$^1$H-NMR (CD$_3$OD) δ 8.73 (s, 1H), 7.61-7.63 (m, 4H), 7.27-7.31 (m, 2H), 6.92-6.99 (m, 3H), 4.18 (t, J=7.78 Hz, 2H), 3.75 (br, s, 2H), 3.58 (br, s, 2H), 3.32 (br, s, 1H), 3.21 (s, 3H), 3.05 (s, 2H), 2.95 (s, 3H), 2.05 (t, J=7.18 Hz, 3H), 1.24 (s, 6H). Mass spectrum (ESI) m/e 501.2 (M+1).

Example 40

1-(3-Methoxy-3-methyl-butyl)-$N^6$-phenyl-$N^3$-(2,4,6-trimethyl-phenyl)-1H-pyrazolo[3,4-d]pyrimidine-3,6-diamine 76

$^1$H-NMR (CD$_3$OD) δ 8.15 (s, 1H), 7.67 (d, J=6.63 Hz, 2H), 7.41 (t, J=7.65 Hz, 2H), 7.22 (t, J=7.42 Hz, 1H), 7.01 (s, 2H), 4.16 (t, J=7.72 Hz, 2H), 3.17 (s, 3H), 2.32 (s, 3H), 2.24 (s, 6H), 2.00 (t, J=7.64 Hz, 2H), 1.20 (s, 6H). Mass spectrum (ESI) m/e=445.3 (M+1).

Example 41

1-(3-Methoxy-3-methyl-butyl)-$N^6$-[4-(4-methyl-piperazin-1-yl)-phenyl-$N^3$-(2,4,6-trimethyl-phenyl)-1H-pyrazolo[3,4-d]pyrimidine-3,6-diamine 77

$^1$H-NMR (CD$_3$OD) δ 8.25 (br, s, 1H), 7.54 (d, J=8.82 Hz, 2H), 7.12 (d, J=9.01 Hz, 2H), 7.00 (s, 2H), 4.12 (t, J=7.72 Hz, 2H), 3.90 (d, J=13.36 Hz, 2H), 3.64 (d, J=11.94 Hz, 2H), 3.14-3.20 (m, 4H), 2.99 (s, 3H), 2.32 (s, 3H), 2.24 (s, 9H), 1.98 (t, J=7.61 Hz, 2H), 1.20 (s, 6H). Mass spectrum (ESI) m/e=543.4 (M+1).

Example 42

$N^3$-(4-Fluoro-2,6-dimethyl-phenyl)-1-(3-methoxy-3-methyl-butyl)-$N^6$-phenyl-1H-pyrazolo[3,4-d]pyrimidine-3,6-diamine 78

$^1$H-NMR (CD$_3$OD) δ 8.45 (s, 1H), 7.66 (d, J=8.35 Hz, 2H), 7.43 (t, J=7.78 Hz, 2H), 7.23 (t, J=10.5 Hz, 1H), 6.92 (d, J=9.16 Hz, 2H), 4.15 (t, J=7.78 Hz, 2H), 3.16 (s, 3H), 2.29 (s, 6H), 1.20 (s, 6H). Mass spectrum (ESI) m/e=449.2 (M+1).

Example 43

$N^3$-(4-Fluoro-2,6-dimethyl-phenyl)-1-(3-methoxy-3-methyl-butyl)-$N^6$-[4-(4-methyl-piperazin-1-yl)-phenyl]-1H-pyrazolo[3,4-d]pyrimidine-3,6-diamine 79

$^1$H-NMR (CD$_3$OD) δ 8.52 (br, s, 1H), 7.57 (d, J=7.58 Hz, 2H), 7.16 (d, J=7.48 Hz, 2H), 6.92 (d, J=8.77 Hz, 2H), 4.10 (t, J=6.45 Hz, 2H), 3.88 (d, J=12.46 Hz, 2H), 3.66 (d, J=10.93 Hz, 2H), 3.32-3.35 (m, 2H), 3.21 (t, J=12.66 Hz, 2H), 3.14 (s, 3H), 3.00 (s, 3H), 2.29 (s, 6H), 1.95 (t, J=6.40 Hz, 2H), 1.19 (s, 6H). Mass spectrum (ESI) m/e=547.3 (M+1).

Example 44

$N^3$-(2,6-dichlorophenyl)-1-(3-methoxy-3-methylbutyl)-$N^6$-[4-(4-methyl-piperazin-1-yl)-phenyl]-1H-indazole-3,6-diamine 80

$^1$H-NMR (CD$_3$OD) δ 1.23 (s, 6H), 2.04-2.09 (m, 2H), 3.22 (s, 3H), 4.28-4.32 (m, 2H), 6.35 (s, 1H), 7.03-7.14 (m, 2H), 7.26-7.46 (m, 4H), 7.71-7.73 (m, 2H), 8.04 (s, 1H). Mass Spectrum (ESI) m/e=469 (M+1).

Example 45

(9H-Fluoren-9-yl)methyl 4-(4-(3-(2,6-dichlorophenylamino)-1-(3-methoxy-3-methyl-butyl)-1H-indazol-6-ylamino)phenyl)piperazine-1-carboxylate 81

$^1$H-NMR (CDCl$_3$) δ 1.23 (s, 6H), 2.04-2.09 (m, 2H), 3.22 (s, 3H), 4.28-4.32 (m, 2H), 6.35 (s, 1H), 7.03-7.14 (m, 2H), 7.26-7.46 (m, 4H), 7.71-7.73 (m, 2H), 8.04 (s, 1H). Mass Spectrum (ESI) m/e=469 (M+1).

Example 46

N$^3$-(2,6-Dichlorophenyl)-N$^6$-(3-fluoro-4-(2-(pyrrolidin-1-yl)ethoxy)phenyl)-1-(3-methoxy-3-methylbutyl)-1H-pyrazolo[3,4-d]pyrimidine-3,6-diamine 82

$^1$H-NMR (CDCl$_3$) δ 1.24 (s, 6H), 2.03-2.21 (m, 6H), 3.01-3.09 (m, 2H), 3.20 (s, 3H), 3.58 (t, J=4.4 Hz, 2H), 3.91-3.98 (m, 2H), 4.24-4.30 (m, 2H), 4.42 (t, J=4.4 Hz, 2H), 6.65 (s, 1H), 6.95 (t, J=8.9 Hz, 1H), 7.40 (d, J=8.5 Hz, 1H), 7.46 (d, J=8.1 Hz, 2H), 7.81 (dd, J=13.0 Hz, 2.5 Hz, 1H), 7.84 (s, 1H), 11.70 (s, 1H). Mass Spectrum (ESI) m/e=602.2 (M+1).

Example 47

N$^3$-(2,6-dichlorophenyl)-1-(3-methoxy-3-methylbutyl)-N$^6$-methyl-1H-pyrazolo[3,4-d]pyrimidine-3,6-diamine 83

A sealed tube containing 55 mg (0.13 mmol) of 6-chloro-N-(2,6-dichlorophenyl)-1-(3-methoxy-3-methylbutyl)-1H-pyrazolo[3,4-d]pyrimidin-3-amine (prepared as described in Example 1, Step B), 650 µl (2.0 M, 1.3 mmol) of a THF solution of dimethylamine and 120 µl (1.6 mmol) of TFA in 3 mL 1,4-dioxane was heated at 100° C. for 21 h. After this time, 650 µl (2.0 M, 1.3 mmol) of a THF solution of dimethylamine and 120 µl (1.6 mmol) of TFA were added, and heating was continued at 100° C. for an additional 23 h. The orange solution was concentrated, and the residue was purified by HPLC (Capcell Pak C$_{18}$ 5 µm, gradient of 80% A:20% B to 30% A:70% B over 45 min; A=0.5% TFA in water, B=0.5% TFA in acetonitrile) to give the title compound. $^1$H-NMR (CDCl$_3$) δ 1.25 (s, 6H), 2.01-2.08 (m, 2H), 3.05 (s, 3H), 3.22 (s, 3H), 4.19-4.26 (m, 2H), 6.60 (s, 1H), 7.24 (t, J=8.4 Hz, 1H), 7.46 (d, J=8.1 Hz, 2H), 7.77 (s, 1H), 9.49 (s, 1H). Mass Spectrum (ESI) m/e=409.1.

Example 48

N$^3$-(2,6-dichlorophenyl)-1-(3-methoxy-3-methylbutyl)-N$^6$-[4-piperazin-1-yl)-phenyl]-1H-indazole-3,6-diamine 84

(9H-Fluoren-9-yl)methyl 4-(4-(3-(2,6-dichlorophenylamino)-1-(3-methoxy-3-methyl-butyl)-1H-indazol-6-ylamino)phenyl)piperazine-1-carboxylate 81 (Example 45) was treated with 50% piperidine in DCM (2 mL) at room temperature for 1 h. Removal of solvents followed by column chromatography on silica gel (eluents: DCM/MeOH/NH$_4$OH, 20/1/0.2) gave the title compound. $^1$H-NMR (CD$_3$OD) δ 1.23 (s, 6H), 1.96-1.99 (m, 2H), 3.14 (s, 3H), 3.43-3.45 (m, 4H), 3.51-3.53 (m, 4H), 4.13-4.16 (m, 2H), 7.17-7.19 (m, 2H), 7.31-7.34 (m, 1H), 7.52-7.53 (m, 2H), 7.58-7.60 (m, 2H), 8.83 (s, 1H). Mass Spectrum (ESI) m/e=553 (M+1).

Example 49

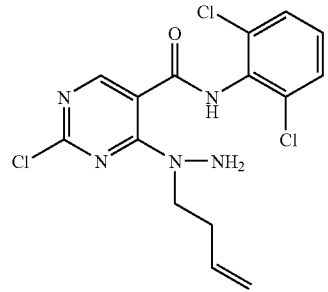

85

Step A. Synthesis of 4-(1-(but-3-enyl)hydrazinyl)-2-chloro-N-(2,6-dichlorophenyl)pyrimidine-5-carboxamide 85

A solution of 230 mg (2.7 mmol) of 3-butenylhydrazine in 10.5 mL of THF was cooled to 0° C. and treated sequentially with 800 mg (2.4 mmol) of 2,4-dichloro-N-(2,6-dichlorophenyl)pyrimidine-5-carboxamide and 370 µl (2.6 mmol) of triethylamine. The resulting yellow slurry was warmed to room temperature and stirred for 25 h. The reaction mixture was quenched with saturated aqueous ammonium chloride (15 mL) and extracted with CH$_2$Cl$_2$ (3×20 mL). The combined organic layers were dried over Na$_2$SO$_4$, filtered, and the filtrate was purified by chromatography on silica gel (eluens CH$_2$Cl$_2$:MeOH, 99.5:0.5) to give the title compound 85. $^1$H-NMR (DMSO-d$_6$) δ 3.17 (d, J=5.2 Hz, 2H), 3.31 (s, 2H), 3.80 (t, J=7.3 Hz, 2H), 5.04 (d, J=10.3 Hz, 1H), 5.13 (d, J=17.1 Hz, 1H), 5.77-5.88 (m, 1H), 7.35 (t, J=8.3 Hz, 1H), 7.55 (d, J=8.2 Hz, 2H), 8.15 (s, 1H), 10.19 (s, 1H). Mass Spectrum (ESI) m/e=385.9 (M+1).

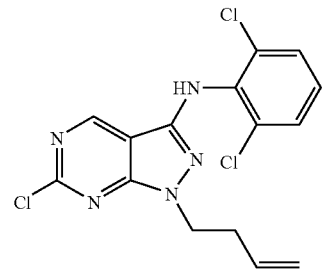

86

Step B. Synthesis of 1-(but-3-enyl)-6-chloro-N-(2,6-dichlorophenyl)-1H-pyrazolo[3,4-d]pyrimidin-3-amine 86

The title compound was prepared as described in Example 1, Step D. $^1$H-NMR (CDCl$_3$) δ 2.63 (q, J=7.1 Hz, 7.1 Hz, 2H), 4.35 (t, J=7.2 Hz, 2H), 4.99 (dd, J=10.3 Hz, 1.6 Hz, 1H), 5.05 (dd, J=17.1 Hz, 1.6 Hz, 1H), 5.72-5.83 (m, 1H), 6.33 (s, 1H), 7.17 (t, J=8.1 Hz, 1H), 7.43 (d, J=8.1 Hz, 2H), 8.27 (s, 1H). Mass Spectrum (ESI) m/e=367.9 (M+1).

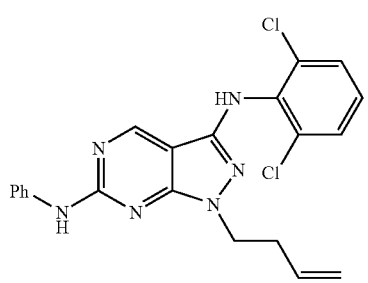

Step C. 1-(But-3-enyl)-N³-(2,6-dichlorophenyl)-N⁶-phenyl-1H-pyrazolo[3,4-d]pyrimidine-3,6-diamine 87

The title compound was prepared as described in Example 1, Step B. ¹H-NMR (CDCl₃) δ 2.62-2.71 (q, J=6.7 Hz, 2H), 4.28 (t, J=6.9 Hz, 2H), 5.02 (d, J=10.8 Hz, 1H), 5.11 (d, J=17.0 Hz, 1H), 5.75-5.88 (m, 1H), 6.27 (s, 1H), 7.03-7.17 (m, 2H), 7.30-7.42 (m, 4H), 7.70 (d, J=8.1 Hz, 2H), 8.11 (s, 1H). Mass Spectrum (ESI) m/e=425.0 (M+1).

Example 50

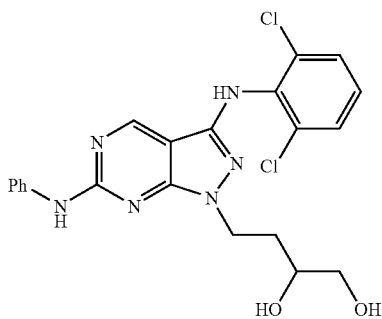

Synthesis of 4-(3-(2,6-dichlorophenylamino)-6-(phenylamino)-1H-pyrazolo[3,4-d]pyrimidin-1-yl)butane-1,2-diol 88

The title compound 88 was prepared as described in Example 2. ¹H-NMR (DMSO-d₆) δ 1.56-1.68 (m, 1H), 1.87-1.99 (m, 1H), 3.19-3.27 (m, 1H), 3.38-3.47 (m, 1H), 4.04-4.18 (m, 3H), 4.46 (t, J=5.7 Hz, 1H), 4.54 (d, J=5.0 Hz, 1H), 6.96 (t, J=7.3 Hz, 1H), 7.22-7.31 (m, 3H), 7.55 (d, J=8.1 Hz, 2H), 7.87 (d, J=8.2 Hz, 2H), 8.70 (d, J=5.5 Hz, 2H), 9.67 (s, 1H). Mass Spectrum (ESI) m/e=459.0 (M+1).

Example 51

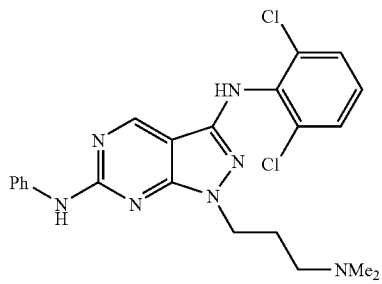

Synthesis of N³-(2,6-Dichlorophenyl)-1-(3-(dimethylamino)propyl)-N⁶-phenyl-1H-pyrazolo[3,4-d]pyrimidine-3,6-diamine 89

The title compound was prepared according to the procedures described in Example 4 and Example 5. ¹H-NMR (CD₃OD) δ 2.00-2.10 (m, 2H), 2.34 (s, 6H), 2.56 (t, J=7.7 Hz, 2H), 4.23 (t, J=6.5 Hz, 2H), 7.02 (t, J=7.4 Hz, 1H), 7.23 (t, J=8.1 Hz, 1H), 7.32 (t, J=8.0 Hz, 2H), 7.47 (d, J=8.1 Hz, 2H), 7.78 (d, J=7.8 Hz, 2H), 8.60 (s, 1H). Mass Spectrum (ESI) m/e=456.1 (M+1).

Example 52

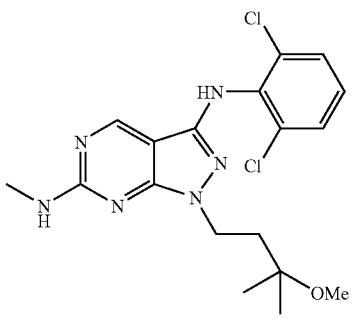

Synthesis of N³-(2,6-dichlorophenyl)-1-(3-methoxy-3-methylbutyl)-N⁵-methyl-1H-pyrazolo[3,4-d]pyrimidine-3,6-diamine 90

A sealed tube containing 55 mg (0.13 mmol) of 6-chloro-N-(2,6-dichlorophenyl)-1-(3-methoxy-3-methylbutyl)-1H-pyrazolo[3,4-d]pyrimidin-3-amine (prepared as described in Example 1, Step D), 650 µl (2.0 M, 1.3 mmol) of a THF solution of dimethylamine and 120 µl (1.6 mmol) of TFA in 3 mL 1,4-dioxane was heated at 100° C. for 21 h. After this time, 650 µl (2.0 M, 1.3 mmol) of a THF solution of dimethylamine and 120 µl (1.6 mmol) of TFA were added, and heating was continued at 100° C. for an additional 23 h. The orange solution was concentrated, and the residue was purified by HPLC (Capcell Pak C₁₈ 5 µm, gradient of 80% A:20% B to 30% A:70% B over 45 min; A=0.5% TFA in water, B=0.5% TFA in acetonitrile) to give the title compound 90. ¹H-NMR (CDCl₃) δ 1.25 (s, 6H), 2.01-2.08 (m, 2H), 3.05 (s, 3H), 3.22 (s, 3H), 4.19-4.26 (m, 2H), 6.60 (s, 1H), 7.24 (t, J=8.4 Hz, 1H), 7.46 (d, J=8.1 Hz, 2H), 7.77 (s, 1H), 9.49 (s, 1H). Mass Spectrum (ESI) m/e=409.1 (M+1).

Example 53

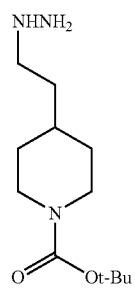

Step A. Synthesis of tert-butyl 4-(2-hydrazinylethyl)piperidine-1-carboxylate 91

A solution of 8.15 g (31 mmol) of triphenylphosphine and 2.56 g (38 mmol) of imidazole in 100 mL CH$_2$Cl$_2$ was cooled to 0° C. and treated with 7.77 g (31 mmol) of iodine. The resulting orange slurry was stirred at 0° C. for 1.25 h, and then 5.0 mL (97%, 22 mmol) of N-Boc-4-piperidineethanol was added quickly dropwise. The orange slurry was warmed to room temperature and stirred for 24 h. The reaction mixture was poured into a mixture of hexane (300 mL) and ether (150 mL) and directly eluted through a large silica gel column (hexane:ether, 2:1) to give the iodide.

A solution of 7.26 g (21 mmol) of the iodide in 10 mL absolute EtOH was treated with 6.7 mL (215 mmol) of hydrazine hydrate. The resulting yellow solution was heated at reflux for 6.5 h, and then was concentrated. The aqueous residue was extracted with ether (3×30 mL), and the combined organic layers were dried over KOH pellets, filtered, and the filtrate was purified by chromatography on silica gel (CH$_2$Cl$_2$:MeOH, 95:5 grading to CH$_2$Cl$_2$: MeOH, 94:6) to give the title compound 91. $^1$H-NMR (CDCl$_3$) δ 1.45 (s, 9H), 1.61-1.85 (m, 8H), 2.62-2.77 (m, 2H), 3.99-4.16 (m, 2H).

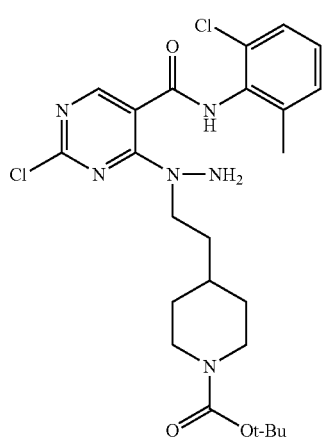

92

Step B. Synthesis of tert-butyl 4-(2-(2-chloro-5-((2,6-dichlorophenyl)carbamoyl)pyrimidin-4-ylhydrazinyl)ethyl)piperidine-1-carboxylate 92

A solution of 618 mg (2.5 mmol) of tert-butyl 4-(2-hydrazinylethyl)piperidine-1-carboxylate in 10 mL THF was cooled to 0° C. and treated sequentially with 763 mg (2.3 mmol) of 2,4-dichloro-N-(2,6-dichlorophenyl)pyrimidine-5-carboxamide and 355 µl (2.5 mmol) of triethylamine. The resulting yellow slurry was warmed to room temperature and stirred for 66 h. The reaction mixture was quenched with saturated aqueous ammonium chloride (20 mL) and extracted with CH$_2$Cl$_2$ (3×30 mL). The combined organic layers were dried over Na$_2$SO$_4$, filtered, and the filtrate was purified by chromatography on silica gel (CH$_2$Cl$_2$:MeOH, 99.5:0.5 grading to CH$_2$Cl$_2$:MeOH, 98:2) to give the title compound 92. $^1$H-NMR (CDCl$_3$) δ 1.08-1.23 (m, 3H), 1.45 (s, 9H), 1.58-1.66 (m, 2H), 1.72-1.79 (m, 2H), 2.61-2.75 (m, 2H), 3.87 (t, J=7.1 Hz, 2H), 3.99-4.14 (m, 4H), 7.24 (t, J=8.4 Hz, 1H), 7.43 (d, J=8.1 Hz, 2H), 7.48 (s, 1H), 8.40 (s, 1H). Mass Spectrum (ESI) m/e=543.1 (M+1).

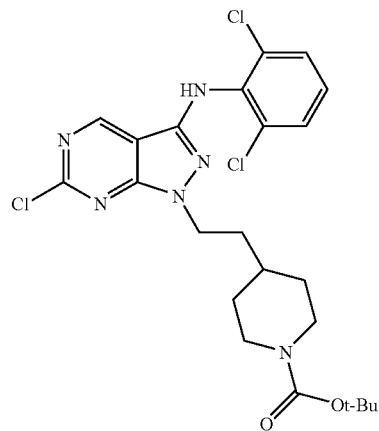

Step C. Synthesis of tert-butyl 4-(2-(6-chloro-3-(2,6-dichlorophenylamino)-1H-pyrazolo[3,4-d]pyrimidin-1-yl)ethyl)piperidine-1-carboxylate 93

A mixture of 655 mg (1.2 mmol) of tert-butyl 4-(2-(2-chloro-5-((2,6-dichlorophenyl)carbamoyl)pyrimidin-4-yl-hydrazinyl)ethyl)piperidine-1-carboxylate 92 in 15 mL of toluene was treated with 270 mg (95%, 1.2 mmol) of phosphorus pentachloride. The resulting bright yellow slurry was heated to 100° C. for 1.25 h, and then was concentrated. The residue was dissolved in a mixture of CH$_2$Cl$_2$ (75 mL) and MeOH (5 mL) and washed with saturated aqueous sodium bicarbonate solution (45 mL). The aqueous layer was extracted with more CH$_2$Cl$_2$ (50 mL). The combined organic layers were dried over Na$_2$SO$_4$, filtered, and the filtrate was purified by chromatography on silica gel (eluens CH$_2$Cl$_2$: MeOH, 99:1) to give the title compound 93. $^1$H-NMR (CDCl$_3$) δ 1.08-1.22 (m, 3H), 1.45 (s, 9H), 1.67-1.76 (m, 2H), 1.77-1.86 (m, 2H), 2.62-2.70 (m, 2H), 3.97-4.12 (m, 2H), 4.31 (t, J=7.11 Hz, 2H), 6.34 (s, 1H), 7.18 (t, J=8.1 Hz, 1H), 7.43 (d, J=8.1 Hz, 2H), 8.32 (s, 1H). Mass Spectrum (ESI, negative mode) m/e=523.2 (M−1).

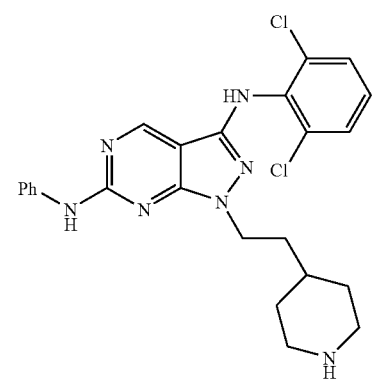

Step D. Synthesis of $N^3$-(2,6-dichlorophenyl)-$N^6$-phenyl-1-(2-(piperidin-4-yl)ethyl)-1H-pyrazolo[3,4-d]pyrimidine-3,6-diamine 94

A solution of 48.5 mg (0.09 mmol) of tert-butyl 4-(2-(6-chloro-3-(2,6-dichlorophenylamino)-1H-pyrazolo[3,4-d]pyrimidin-1-yl)ethyl)piperidine-1-carboxylate 93 in 5 mL 1,4-dioxane was treated sequentially with 17 µl (0.2 mmol) of aniline and 525 µl (7.1 mmol) of TFA. The resulting orange solution was heated at reflux for 22 h, and then was concentrated. The residue was purified by chromatography on silica gel ($CH_2Cl_2$:MeOH, 9:1) to give the title compound 94. $^1$H-NMR ($CD_3OD$) δ 1.22-1.45 (m, 3H), 1.66-1.78 (m, 2H), 1.91-2.02 (m, 2H), 2.10 (s, 1H), 2.62-2.74 (m, 2H), 3.10-3.23 (m, 2H), 4.15 (t, J=6.3 Hz, 2H), 6.99 (t, J=8.0 Hz, 1H), 7.19 (t, J=8.1 Hz, 1H), 7.23-7.31 (m, 2H), 7.42 (t, J=8.5 Hz, 2H), 7.71 (d, J=8.5 Hz, 2H), 8.56 (s, 1H). Mass Spectrum (ESI) m/e=482.0 (M+1).

Analytical Methods

HPLC Methods

Unless otherwise indicated all HPLC analyses were run on an HP-1000 or HP-1050 system with an HP Zorbax SB-C18 (5µ) reverse phase column (4.6×150 mm) run at 30° C. with a flow rate of 1.00 mL/min. The mobile phase used solvent A ($H_2O$/0.1% TFA) and solvent B ($CH_3CN$/0.1% TFA) with a 20 min gradient from 10% to 90% $CH_3CN$. The gradient was followed by a 2 min return to 10% $CH_3CN$ and a 3 min flush.

LC-MS Methods

Unless otherwise noted, the LC-MS analysis of exemplary compounds, intermediates and starting materials described here were conducted using one or both of the following two methods:

Method A: Samples were run on an HP-1100 system with a Cellpak-$Cl_8$ (5µ) reverse phase column (4.6×50 mm) run at 30° C. with a flow rate of 3 mL/min. The mobile phase used solvent A ($H_2O$/0.1% AcOH) and solvent B ($CH_3CN$/0.1% AcOH) with a 4 min gradient from 10% to 90% $CH_3CN$. The gradient was followed by a 1 min return to 10% $CH_3CN$ and a 1 min flush.

Method B: Samples were run on an HP-1100 system with an HP Zorbax SB-$Cl_8$ (5µ) reverse phase column (4.6×50 mm) run at 30° C. with a flow rate of 3 mL/min. The mobile phase used solvent A ($H_2O$/0.1% AcOH) and solvent B ($CH_3CN$/0.1% AcOH) with a 4 min gradient from 10% to 90% $CH_3CN$. The gradient was followed by a 0.5 min return to 10% $CH_3CN$ and a 1.5 min flush.

Proton NMR Spectra

Unless otherwise indicated all $^1$H NMR spectra were run on a Bruker 400 MHz instrument. All observed protons are reported as parts per million (ppm) downfield from tetramethylsilane (TMS) or other internal reference in the appropriate solvent indicated.

Biological Assays

The following assays can be employed to determine the degree of activity of a compound as a protein kinase inhibitor. Compounds described herein have been tested in one or more of these assays, and have shown activity. Representative compounds of the invention were tested and found to exhibit $IC_{50}$ values of at least <10 µM in any one of the described assays, thereby demonstrating and confirming the utility of the compounds of the invention as protein kinase inhibitors and in the prophylaxis and treatment of immune diseases, hyperproliferative disorders, etc.

LCK-Homogeneous Time Resolved Fluorescent (HTRF) Kinase Assay

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 10 µL of compound in 100% DMSO, 15 µL of ATP and biotinylated Gastrin, and 15 µL of LCK KD GST (225-509) for a final volume of 40 µL. The final concentration of gastrin is 1.2 µM. The final concentration of ATP is 0.5 µM (Km app=0.6+/−0.1 µM) and the final concentration of LCK is 250 pM. Buffer conditions are as follows: 50 mM HEPES pH 7.5, 50 mM NaCl, 20 mM $MgCl_2$, 5 mM $MnCl_2$, 2 mM DTT, 0.05% BSA.

The assay is quenched and stopped with 160 µL of a detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final concentration in the assay of 0.0004 mg/mL, and europilated anti-phosphotyrosine Ab (Eu-anti-PY) at a final concentration of 0.025 nM.

The assay plate is read in either a Discovery or a RubyStar. The eu-anti-PY is excited at 320 nm and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Human Mixed Lymphocyte Reaction (huMLR)

The purpose of this assay is to test the potency of T cell activation inhibitors in an in vitro model of allogeneic T cell stimulation. Human peripheral blood lymphocytes (hPBL; $2 \times 10^5$/well) are incubated with mitomycin C-treated B lymphoblastoid cells (JY cell line; $1 \times 10^5$/well) as allogeneic stimulators in the presence or absence of dilutions of potential inhibitor compound in 96-well round-bottom tissue culture plates. These cultures are incubated at 37° C. in 5% $CO_2$ for 6 days total. The proliferative response of the hPBL is measured by $^3$H-thymidine incorporation overnight between days 5 and 6 after initiation of culture. Cells are harvested onto glass fiber filters and $^3$H-thymidine incorporation into DNA is analyzed by liquid scintillation counter.

Jurkat Proliferation/Survival Assay

The purpose of this assay is to test the general anti-proliferative/cytotoxic effect of compounds on the Jurkat human T cell line. Jurkat cells ($1 \times 10^5$/well) are plated in 96-well flat-bottom tissue culture plates with or without compound dilutions and cultured for 72 h at 37° C. in 5% $CO_2$. Viable cell number is determined during the last 4 h of culture by adding 10 µL/well WST-1 dye. WST-1 dye conversion relies on active mitochondrial electron transport for reduction of the tetrazolium dye. The dye conversion is read by OD at 450-600 nm.

Anti-CD3/CD28-Induced T cell IL-2 Secretion and Proliferation Assay

The purpose of this assay is to test the potency of T cell receptor (TCR; CD3) and CD28 signaling pathway inhibitors in human T cells. T cells are purified from human peripheral blood lymphocytes (hPBL) and pre-incubated with or without compound prior to stimulation with a combination of an anti-CD3 and an anti-CD28 antibody in 96-well tissue culture plates ($1 \times 10^5$ T cells/well). Cells are cultured for ~20 h at 37° C. in 5% $CO_2$, then secreted IL-2 in the supernatants is quantified by cytokine ELISA (Pierce/Endogen). The cells remaining in the wells are then pulsed with $^3$H-thymidine overnight to assess the T cell proliferative response. Cells are harvested onto glass fiber filters and $^3$H-thymidine incorporation into DNA is analyzed by liquid scintillation counter. For comparison purposes, phorbol myristic acid (PMA) and calcium ionophore can be used in combination to induce IL-2 secretion from purified T cells. Potential inhibitor compounds can be tested for inhibition of this response as described above for anti-CD3 and -CD28 antibodies.

ACK1 Enzymatic Assay $IC_{50}$ values of compounds of the invention may be assessed as follows. The ACK1 kinase assay utilizes a protein expressed in baculovirus infected Hi-5 cells (a fusion of an N-terminal (His)$_6$ Tag with amino acids 117 to 489 of ACK1) purified by affinity chromatography on a Ni-NTA column. The substrate for the reaction is ACK1 itself (autophosphorylation) and poly-Glutamic acid-Tyrosine (PGT (4:1), Sigma catalog #PO275). The PGT is coated to Nunc 96 well plates at 80 μg/mL overnight at 4° C. The morning after coating, the plates are washed twice, and 80 mL reaction buffer (10 mM Hepes, pH 7.6; 20 mM $MgCl_2$; 75 mM NaCl, 0.125% TWEEN20 (polyoxyethylene sorbitan monolaurate); 1 mM DTT) with 5 μM ATP are added to each well. Test compounds are added in 10 mL DMSO, and the reaction is started by addition of 10 mL kinase in assay buffer. The reaction proceeds for 2 h at room temperature. Next, the plates are washed four times, and the level of tyrosine phosphorylation in a given well is quantified by standard ELISA assay utilizing a phosphotyrosine antibody (PY20, Pierce). The above compounds that have been evaluated exhibited an $IC_{50}$ value of less than about 30 μM with respect to ACK1.

ACK1 Cell Based Assay

The ACK1 cell based assay is designed to find inhibitors of ACK1 kinase activity which would be prime candidates for the development of anticancer drugs. The assay is based on the dependence of certain transformed cell lines (e.g., C8 cells, a Ras and E1A transformed fibroblast line) on ACK1 for survival under low serum conditions, whereas other cell lines (e.g., HeLa) do not. This dependency was confirmed utilizing ACK1 specific siRNAs.

For this assay, test (C8) and control (HeLa) cell lines are seeded in 96 well tissue culture plates (BD Falcon) at a density of 2 to 4×10$^4$ in DMEM/F12 (C8) or DMEM (HeLa) with 0.125% FCS in the presence of ACK1 inhibitors (final DMSO concentration is 0.5%, all tissue culture media are from Cellgro). After 20 to 24 h incubation at 37° C. and 5% $CO_2$, cell viability is determined using the Cytotox One kit (Promega) according to the manufacturer's instructions.

Compounds of the invention having useful activity as measured by $K_i$ and $IC_{50}$ are shown in Table 3.

TABLE 3

| Compound | Name | Ack1 $K_i$ | ACK1 Cell-based $IC_{50}$ | Lck $K_i$ |
|---|---|---|---|---|
| 33 | 1-(but-3-enyl)-N$^3$-(2,6-dimethylphenyl)-N$^6$-phenyl-1H-pyrazolo[3,4-d]pyrimidine-3,6-diamine | ++ | + | +++ |
| 34 | 4-(3-(2,6-dimethylphenylamino)-6-(phenylamino)-1H-pyrazolo[3,4-d]pyrimidin-1-yl)butane-1,2-diol | ++ | ++ | +++ |
| 35 | 1-(2-(1,3-dioxolan-4-yl)ethyl)-N3-(2,6-dimethylphenyl)-N6-phenyl-1H-pyrazolo[3,4-d]pyrimidine-3,6-diamine | ++ | + | +++ |
| 37 | 3-(3-(2,6-dimethylphenylamino)-6-(phenylamino)-1H-pyrazolo[3,4-d]pyrimidin-1-yl)propan-1-ol | ++ | + | +++ |
| 38 | 1-(3-(dimethylamino)propyl)-N3-(2,6-dimethylphenyl)-N6-phenyl-1H-pyrazolo[3,4-d]pyrimidine-3,6-diamine | ++ | ++ | +++ |
| 39 | N$^3$-(2,6-dimethylphenyl)-1-(3-(methylamino)propyl)-N$^6$-phenyl-1H-pyrazolo[3,4-d]pyrimidine-3,6-diamine | ++ | + | +++ |
| 40 | 1-(3-(diethylamino)propyl)-N$^3$-(2,6-dimethylphenyl)-N$^6$-phenyl-1H-pyrazolo[3,4-d]pyrimidine-3,6-diamine | ++ | + | +++ |
| 41 | N$^3$-(2,6-dimethylphenyl)-N$^6$-phenyl-1-(3-(pyrrolidin-1-yl)propyl)-1H-pyrazolo[3,4-d]pyrimidine-3,6-diamine | ++ | + | +++ |
| 43 | 1-(dimethylamino)-4-(3-(2,6-dimethylphenylamino)-6-(phenylamino)-1H-pyrazolo[3,4-d]pyrimidin-1-yl)butan-2-ol | ++ | + | +++ |
| 44 | 1-(diethylamino)-4-(3-(2,6-dimethylphenylamino)-6-(phenylamino)-1H-pyrazolo[3,4-d]pyrimidin-1-yl)butan-2-ol | + | + | +++ |
| 45 | 4-(3-(2,6-dimethylphenylamino)-6-(phenylamino)-1H-pyrazolo[3,4-d]pyrimidin-1-yl)-1-(pyrrolidin-1-yl)butan-2-ol | + | + | +++ |
| 46 | 4-(3-(2,6-dimethylphenylamino)-6-(phenylamino)-1H-pyrazolo[3,4-d]pyrimidin-1-yl)butan-2-ol | ++ | + | +++ |
| 48 | N$^3$-(2,6-dimethyl-phenyl)-N$^6$-phenyl-1-(3-piperidin-1-yl-propyl)-1H-pyrazolo[3,4-d]pyrimidine-3,6-diamine | + | + | +++ |
| 49 | N$^3$-(2,6-dimethyl-phenyl)-N$^6$-(4-piperazin-1-yl-phenyl)-1-(3-piperidin-1-yl-propyl)-1H-pyrazolo[3,4-d]pyrimidine-3,6-diamine | ++ | + | +++ |
| 50 | N$^3$-(2,6-dimethyl-phenyl)-N$^6$-[4-(4-methyl-piperazin-1-yl)-phenyl]-1-(3-piperidin-1-yl-propyl)-1H-pyrazolo[3,4-d]pyrimidine-3,6-diamine | ++ | ++ | +++ |
| 51 | N$^3$-(2,6-dimethyl-phenyl)-1-(2-morpholin-4-yl-ethyl)-N$^6$-phenyl-1H-pyrazolo[3,4-d]pyrimidine-3,6-diamine | ++ | + | +++ |
| 52 | N$^3$-(2,6-dimethyl-phenyl)-N$^6$-[4-(2-methoxy-ethoxy)-phenyl]-1-(2-morpholin-4-yl-ethyl)-1H-pyrazolo[3,4-d]pyrimidine-3,6-diamine | ++ | + | +++ |
| 53 | N$^3$-(2,6-dimethyl-phenyl)-N$^6$-[4-(4-methyl-piperazin-1-yl)-phenyl]-1-(2-morpholin-4-yl-ethyl)-1H-pyrazolo[3,4-d]pyrimidine-3,6-diamine | ++ | + | +++ |
| 54 | N$^3$-(2,6-dimethyl-phenyl)-N$^6$-[4-(2-methoxy-ethoxy)-phenyl]-1-(3-methoxy-3-methyl-butyl)-1H-pyrazolo[3,4-d]pyrimidine-3,6-diamine | ++ | + | +++ |
| 55 | N$^3$-(2,6-dimethyl-phenyl)-1-(3-methoxy-3-methyl-butyl)-N$^6$-[4-(methylpiperazin-1-yl)phenyl]-1H-pyrazolo[3,4-d]pyrimidine-3,6-diamine | +++ | ++ | +++ |

TABLE 3-continued

| Compound | Name | Ack1 $K_i$ | ACK1 Cell-based $IC_{50}$ | Lck $K_i$ |
|---|---|---|---|---|
| 56 | $N^3$-(2,6-dimethyl-phenyl)-1-(3-methoxy-3-methylbutyl)-$N^6$-(4-piperazin-1-yl-phenyl)-1H-pyrazolo[3,4-d]pyrimidine-3,6-diamine | +++ | +++ | +++ |
| 57 | $N^3$-(2,6-dimethylphenyl)-$N^6$-[3-fluoro-4-(3-(piperidin-1-yl)propoxy)phenyl1-1-(3-methoxy-3-methylbutyl)-1H-pyrazolo[3,4-d]pyrimidine-3,6-diamine | ++ | ++ | ++ |
| 58 | $N^3$-(2,6-dimethylphenyl)-1-(3-methoxy-3-methylbutyl)-1H-indazole-3,6-diamine | + | + | +++ |
| 59 | $N^3$-(2,6-dimethylphenyl)-1-(3-methoxy-3-methylbutyl))-$N^6$-phenyl-1H-indazole-3,6-diamine | +++ | ++ | +++ |
| 60 | $N^3$-(2,6-dimethylphenyl)-1-$N^6$-(4-(3,5-dimethylpiperazin-1-yl)phenyl)-1-(3-methoxy-3-methylbutyl)-1H-indazole-3,6-diamine | +++ | ++ | +++ |
| 61 | $N^3$-(2,6-dimethylphenyl)-1-$N^6$-(4-piperazin-1-yl)phenyl)-1-((tetrahydro-2H-pyran-4-yl)methyl)-1H-indazole-3,6-diamine | +++ | +++ | +++ |
| 62 | $N^3$-(2,6-dimethylphenyl)-1-$N^6$-(3-fluoro-4-(piperidin-1-yl)propoxy)phenyl)-1-((tetrahydro-2H-pyran-4-yl)methyl)-1H-indazole-3,6-diamine | +++ | ++ | +++ |
| 63 | $N^3$-(2,6-dimethylphenyl)-$N^6$-phenyl-1-((tetrahydro-2H-pyran-4-yl)methyl)-1H-indazole-3,6-diamine | ++ | + | +++ |
| 64 | ethyl-2-(3-(2,6-dimethylphenylamino)-6-(phenylamino)-1H-indazole-1-yl)acetate | ++ | + | +++ |
| 65 | (R)-$N^3$-(2,6-dimethylphenyl)-$N^6$-(4-fluorophenyl)-1-(3-(2-(methoxymethyl)pyrrolidin-1-yl)propyl)-1H-indazole-3,6-diamine | + | + | +++ |
| 66 | (R)-$N^3$-(2,6-dimethylphenyl)-1-(3-(2-(methoxymethyl)pyrrolidin-1-yl)propyl)-$N^6$-phenyl-1H-indazole-3,6-diamine | + | + | +++ |
| 67 | (R)-$N^3$-(2,6-dimethylphenyl)-1-(3-(2-(methoxymethyl)pyrrolidin-1-yl)propyl)-$N^6$-(4-piperazin-1-yl)phenyl-1H-indazole-3,6-diamine | +++ | ++ | +++ |
| 68 | (R)-$N^3$-(2,6-dimethylphenyl)-1-(3-(2-(methoxymethyl)pyrrolidin-1-yl)propyl)-1H-indazole-3,6-diamine | + | + | ++ |
| 69 | 2-(3-(2,6-dimethylphenylamino)-6-(phenylamino)-1H-indazol-1-yl)acetic acid | ++ | + | +++ |
| 70 | 2-(3-(2,6-dimethylphenylamino)-6-(phenylamino)-1H-indazo1-1-yl)-1-(4-methylpiperazin-1-yl)ethanone | + | + | +++ |
| 71 | 2-(3-(2,6-dimethylphenylamino)-6-(phenylamino)-1H-indazol-1-yl)-1-(piperazin-1-yl)ethanone | + | + | +++ |
| 72 | $N^3$-(2,6-dimethylphenyl)-1-(2-(4-methylpiperazin-1-yl)ethyl)-$N^6$-phenyl-1H-indazole-3,6-diamine | ++ | + | +++ |
| 74 | 1-(3-methoxy-3-methyl-butyl)-$N^3$,$N^6$-diphenyl-1H-pyrazolo[3,4-d]pyrimidine-3,6-diamine | + | + | + |
| 75 | 1-(3-methoxy-3-methyl-butyl)-$N^6$-[4-(4-methyl-piperazin-1-yl)-phenyl-$N^3$-phenyl-1H-pyrazolo[3,4-d]pyrimidine-3,6-diamine | + | + | ++ |
| 76 | 1-(3-methoxy-3-methyl-butyl)-$N^6$-phenyl-$N^3$-(2,4,6-trimethyl-phenyl)-1H-pyrazolo[3,4-d]pyrimidine-3,6-diamine | + | + | +++ |
| 77 | 1-(3-methoxy-3-methyl-butyl)-$N^6$-[4-(4-methyl-piperazin-1-yl)-phenyl-$N^3$-(2,4,6-trimethyl-phenyl)-1H-pyrazolo[3,4-d]pyrimidine-3,6-diamine | ++ | ++ | +++ |
| 78 | $N^3$-(4-fluoro-2,6-dimethyl-phenyl)-1-(3-methoxy-3-methyl-butyl)-$N^6$-phenyl-1H-pyrazolo[3,4-d]pyrimidine-3,6-diamine | ++ | + | +++ |
| 79 | $N^3$-(4-fluoro-2,6-dimethyl-phenyl)-1-(3-methoxy-3-methyl-butyl)-$N^6$-[4-(4-methyl-piperazin-1-yl)-phenyl]-1H-pyrazolo[3,4-d]pyrimidine-3,6-diamine | ++ | ++ | +++ |
| 80 | $N^3$-(2,6-dichlorophenyl)-1-(3-methoxy-3-methylbutyl)-$N^6$-[4-(4-methyl-piperazin-1-yl)-phenyl]-1H-indazole-3,6-diamine | +++ | ++ | +++ |
| 81 | (9H-fluoren-9-yl)methyl 4-(4-(3-(2,6-dichlorophenylamino)-1-(3-methoxy-3-methyl-butyl)-1H-indazol-6-ylamino)phenyl)piperazine-1-carboxylate | ++ | + | +++ |
| 82 | $N^3$-(2,6-dichlorophenyl)-$N^6$-(3-fluoro-4-(2-(pyrrolidin-1-yl)ethoxy)phenyl)-1-(3-methoxy-3-methylbutyl)-1H-pyrazolo[3,4-d]pyrimidine-3,6-diamine | +++ | ++ | +++ |
| 83 | $N^3$-(2,6-dichlorophenyl)-1-(3-methoxy-3-methylbutyl)-$N^6$-methyl-1H-pyrazolo[3,4-d]pyrimidine-3,6-diamine | + | + | +++ |
| 84 | $N^3$-(2,6-dichlorophenyl)-1-(3-methoxy-3-methyl-butyl)-$N^6$-[4-piperazin-1-yl)-phenyl]-1H-indazole-3,6-diamine | ++ | ++ | +++ |
| 87 | 1-(but-3-enyl)-$N^3$-(2,6-dichlorophenyl)-$N^6$-phenyl-1H-pyrazolo[3,4-d]pyrimidine-3,6-diamine | ++ | + | +++ |
| 88 | 4-(3-(2,6-dichlorophenylamino)-6-(phenylamino)-1H-pyrazolo[3,4-d]pyrimidin-1-yl)butane-1,2-diol | ++ | ++ | +++ |
| 89 | $N^3$-(2,6-dichlorophenyl)-1-(3-(dimethylamino)propyl)-$N^6$-phenyl-1H-pyrazolo[3,4-d]pyrimidine-3,6-diamine | +++ | ++ | +++ |
| 90 | $N^3$-(2,6-dichlorophenyl)-1-(3-methoxy-3-methylbutyl)-$N^6$-methyl-1H-pyrazolo[3,4-d]pyrimidine-3,6-diamine | + | + | +++ |
| 94 | $N^3$-(2,6-dichlorophenyl)-$N^6$-phenyl-1-(2-(piperidin-4-yl)ethyl)-1H-pyrazolo[3,4-d]pyrimidine-3,6-diamine | ++ | + | +++ |

Legend:
+ represents: $IC_{50}$ value > 0.1 μM
++ represents: 0.1 μM > $IC_{50}$ value > 0.01 μM
+++ represents: $IC_{50}$ value < 0.01 μM Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of Formula I

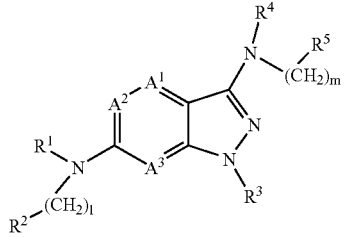

or a stereomer, a tautomer, or a pharmaceutically acceptable salt thereof, wherein $A^1$ is $CR^6$;

$A^2$ and $A^3$ are both N;

$R^1$ is hydrogen, optionally substituted $C_{1-6}$ alkyl, optionally substituted $C_{2-6}$ alkenyl, optionally substituted $C_{2-6}$ alkynyl, wherein the substituents are selected from halo, cyano, $C_{1-6}$ alkyl, $C_{1-6}$ haloalkyl and $C_{1-6}$ alkoxy;

$R^2$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $R^7$, $NR^8R^9$, $OR^{10}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$;

$R^3$ is optionally substituted alkyl, optionally substituted alkenyl or optionally substituted alkynyl, wherein the substituents are selected from $R^{17}$, $NR^8R^9$, $OR^{10}$, $SR^{11}$, $COOR^{12}$, $C(O)R^{13}$, $OC(O)R^{13}$, $R^{13}OR^{10}$, $C(O)NR^8R^9$, $C(S)NR^8R^9$, $NR^{14}C(O)R^{15}$, $NR^{14}C(S)R^{15}$, $NR^{14}C(O)NR^8R^9$, $NR^{14}C(S)NR^8R^9$, $NR^{14}(COOR^{12})$, $OC(O)NR^8R^9$, $S(O)_2R^8$, $S(O)_2NR^8R^9$, $NR^{14}S(O)_2NR^8R^9$, and $NR^8S(O)_2R^9$;

$R^4$ is hydrogen, optionally substituted $C_{1-6}$ alkyl, optionally substituted $C_{2-6}$ alkenyl, optionally substituted $C_{2-6}$ alkynyl, wherein the substituents are selected from halo, $NO_2$, cyano, $C_{1-6}$ alkyl, $C_{1-6}$ haloalkyl and $C_{1-6}$ alkoxy;

$R^5$ is optionally substituted aryl, optionally substituted cycloalkyl, optionally substituted heterocycloalkyl, or optionally substituted heteroaryl, wherein the substituents are selected from $R^7$, $NR^8R^9$, $OR^{10}$, $R^{10}OR^{11}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ and $NR^{17}S(O)_2R^{16}$;

$R^6$ is hydrogen, halogen or optionally substituted $C_{1-6}$ alkyl, wherein the substituents are selected from H, halo, haloalkyl, CN, $NO_2$, OH and $NR^8R^9$;

l and m are independently 0, 1, 2, 3, or 4;

$R^7$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, wherein each of the $C_{1-10}$-alkyl, $C_{2-10}$-alkenyl, $C_{2-10}$-alkynyl, $C_{3-10}$-cycloalkyl and $C_{4-10}$-cycloalkenyl optionally consisting of 1-4 heteroatoms selected from N, O and S, or $R^7$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $C_{1-8}$-alkyl, $C_{2-8}$-alkenyl, $C_{2-8}$-alkynyl, $NR^8R^9$, $OR^{10}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$;

$R^8$ and $R^9$ are each independently H, $C_{1-8}$-alkyl, $C_{3-8}$-cycloalkyl, $C_{2-8}$-alkenyl, $C_{2-8}$-alkynyl, $C_{1-8}$-alkylamino-, $C_{1-8}$-alkoxyl, $C_{1-8}$-thioalkyl, $C_{1-8}$-alkoxy-$C_{1-8}$-alkyl, aryl, heteroaryl, or heterocyclyl;

$R^{10}$, $R^{11}$, and $R^{16}$ are each independently H, $C_{1-8}$-alkyl, $C_{2-8}$-alkenyl, $C_{2-8}$-alkynyl, $C_{1-8}$-alkoxy-$C_{3-8}$-cycloalkyl, aryl, heterocyclyl, $C_{1-8}$-alkyl-heterocyclyl or heterocyclyl-$C_{1-8}$-alkyl;

$R^{12}$, $R^{13}$, $R^{14}$, and $R^{15}$ are each independently H, $C_{1-8}$-alkyl, $C_{3-8}$-cycloalkyl, $C_{2-8}$-alkenyl, $C_{2-8}$-alkynyl, $C_{1-8}$-alkylamino-, $C_{1-8}$-dialkylamino-, $C_{1-8}$-alkoxyl, $C_{1-8}$-thioalkyl, aryl, heteroaryl, heterocyclyl or alkylheterocyclyl; and $R^{17}$ is H, halo, CN, $NO_2$, or Cy;

Cy is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $C_{1-8}$-alkyl, $C_{2-8}$-alkenyl, $C_{2-8}$-alkynyl, $NR^8R^9$, $OR^{10}$, $SR^{11}$, $COOR^{12}$, $C(O)R^{13}$, $R^{13}OR^{10}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$.

2. The compound of claim 1, or a stereomer, a tautomer, or a pharmaceutically acceptable salt thereof, wherein l and m are both 0.

3. The compound of claim 2, or a stereomer, a tautomer, or a pharmaceutically acceptable salt thereof, wherein $R^1$ is H.

4. The compound of claim 1 or a stereomer, a tautomer, or a pharmaceutically acceptable salt thereof, wherein $R^2$ is phenyl.

5. The compound of claim 1, or a stereomer, a tautomer, or a pharmaceutically acceptable salt thereof, wherein $R^2$ is phenylene and $R^7$ is halogen.

6. The compound of claim 1, or a stereomer, a tautomer, or a pharmaceutically acceptable salt thereof, wherein $R^2$ is phenylene-$OR^{10}$.

7. The compound of claim 6, or a stereomer, a tautomer, or a pharmaceutically acceptable salt thereof, wherein $R^{10}$ is heterocyclyl, $C_{1-8}$-alkyl-heterocyclyl or heterocyclyl-$C_{1-8}$-alkyl.

8. The compound of claim 6, or a stereomer, a tautomer, or a pharmaceutically acceptable salt thereof, wherein $R^{10}$ is piperazinyl, methylpiperazinylene, piperazinylalkylene, pyrrolidinyl, or dimethylpiperazinyl.

9. The compound of claim 1 or a stereomer, a tautomer, or a pharmaceutically acceptable salt thereof, wherein $R^3$ is optionally substituted alkyl or alkenyl.

10. The compound of claim 9, or a stereomer, a tautomer, or a pharmaceutically acceptable salt thereof, wherein $R^3$ is alkyl substituted with one or more $OR^{10}$.

11. The compound of claim 10, or a stereomer, a tautomer, or a pharmaceutically acceptable salt thereof, wherein $R^{10}$ is hydrogen or $C_{1-8}$-alkyl.

12. The compound of claim 9, or a stereomer, a tautomer, or a pharmaceutically acceptable salt thereof, wherein $R^3$ is alkyl substituted with one or more $R^{17}$.

13. The compound of claim 12, or a stereomer, a tautomer, or a pharmaceutically acceptable salt thereof, wherein $R^{17}$ is Cy.

14. The compound of claim 12, or a stereomer, a tautomer, or a pharmaceutically acceptable salt thereof, wherein $R^{17}$ is optionally substituted pyrrolidinyl, furanyl, thiophenyl, 2H-pyrrolyl, pyrrolyl, 2-pyrrolinyl, 3-pyrrolinyl, 1,3-dioxolanyl, oxazolyl, thiazolyl, imidazolyl, 2-imidazolinyl, imidazolidinyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, pyridinyl, piperidinyl, 1,4-dioxanyl, morpholinyl, 1,4-dithianyl, thiomorpholinyl, pyridazinyl, pyrimidinyl, pyrazinyl, 1,3,5-triazinyl or 1,3,5-trithianyl.

15. The compound of claim 9, or a stereomer, a tautomer, or a pharmaceutically acceptable salt thereof, wherein $R^3$ is alkyl substituted with one or more $NR^8R^9$.

16. The compound of claim 15, or a stereomer, a tautomer, or a pharmaceutically acceptable salt thereof, wherein $R^8$ and $R^9$ are independently hydrogen or $C_{1-8}$-alkyl.

17. The compound of claim 9, or a stereomer, a tautomer, or a pharmaceutically acceptable salt thereof, wherein $R^3$ is alkyl substituted with one or more $COOR^{12}$.

18. The compound of claim 9, or a stereomer, a tautomer, or a pharmaceutically acceptable salt thereof, wherein $R^3$ is alkyl substituted with one or more $C(O)R^{13}$.

19. The compound of claim 9, or a stereomer, a tautomer, or a pharmaceutically acceptable salt thereof, wherein $R^3$ is alkyl substituted with one or more $C(O)NR^8R^9$.

20. The compound of claim 1, or a stereomer, a tautomer, or a pharmaceutically acceptable salt thereof, wherein $R^4$ is hydrogen or optionally substituted $C_{1-6}$ alkyl.

21. The compound of claim 1, or a stereomer, a tautomer, or a pharmaceutically acceptable salt thereof, wherein $R^4$ is hydrogen and $R^5$ is optionally substituted aryl.

22. A compound of Formula II

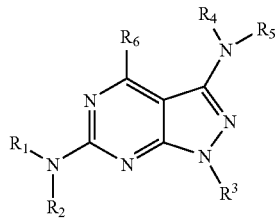

II or a stereomer, a tautomer, or a pharmaceutically acceptable salt thereof, wherein $R^1$ is hydrogen or $C_{1-6}$ alkyl optionally substituted with 1-3 substituents of halo, cyano, $C_{1-6}$ alkyl, $C_{1-6}$ haloalkyl or $C_{1-6}$ alkoxy;

$R^2$ is $C_{3-10}$-cycloalkyl, phenyl, naphthyl, pyridyl, pyrimidinyl, pyridazinyl, triazinyl, piperidinyl, piperazinyl, pyrrolyl, imidazolyl, pyrazolyl, triazolyl, pyrrolidinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, phthalazinyl, morpholinyl, thiophenyl, furyl, dihydrofuryl, tetrahydrofuryl, thiazolyl, oxazolyl, isoxazolyl, isothiazolyl, indolyl, isoindolyl, indolinyl, benzofuranyl, dihydrobenzofuranyl, benzothiophenyl, benzimidazolyl, benzoxazolyl, benzisoxazolyl or benzothiazolyl, each of which is optionally substituted independently with 1-3 substituents of $R^7$, $NR^8R^9$, $OR^{10}$, $SR^{11}$, C(O) $R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$;

$R^3$ is optionally substituted alkyl, optionally substituted alkenyl or optionally substituted alkynyl, wherein the substituents are selected from $R^{17}$, $NR^8R^9$, $OR^{10}$, $SR^{11}$, $COOR^{12}$, $C(O)R^{13}$, $OC(O)R^{13}$, $R^{13}OR^{10}$, $C(O)NR^8R^9$, $C(S)NR^8R^9$, $NR^{14}C(O)R^{15}$, $NR^{14}C(S)R^{15}$, $NR^{14}C(O)NR^8R^9$, $NR^{14}C(S)NR^8R^9$, $NR^{14}(COOR^{12})$, $OC(O)NR^8R^9$, $S(O)_2R^8$, $S(O)_2NR^8R^9$, $NR^{14}S(O)_2NR^8R^9$, and $NR^8S(O)_2R^9$;

$R^4$ is hydrogen or $C_{1-6}$ alkyl optionally substituted with 1-3 substituents of halo, cyano, $C_{1-6}$ alkyl, $C_{1-6}$ haloalkyl or $C_{1-6}$ alkoxy;

$R^5$ is $C_{3-10}$-cycloalkyl, phenyl, naphthyl, pyridyl, pyrimidinyl, pyridazinyl, triazinyl, piperidinyl, piperazinyl, pyrrolyl, imidazolyl, pyrazolyl, triazolyl, pyrrolidinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, phthalazinyl, morpholinyl, thiophenyl, furyl, dihydrofuryl, tetrahydrofuryl, thiazolyl, oxazolyl, isoxazolyl, isothiazolyl, indolyl, isoindolyl, indolinyl, indazolyl, benzofuranyl, dihydrobenzofuranyl, benzothiophenyl, benzimidazolyl, benzoxazolyl, benzisoxazolyl or benzothiazolyl, each of which is optionally substituted independently with 1-3 substituents of $R^7$, $NR^8R^9$, $OR^{10}$, $R^{10}OR^{11}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ and $NR^{17}S(O)_2R^{16}$;

$R^6$ is hydrogen, halogen or $C_{1-6}$ alkyl optionally substituted with 1-3 substituents of halo, haloalkyl, CN, $NO_2$, OH and $NR^8R^9$;

$R^7$ is halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, wherein each of the $C_{1-10}$-alkyl, $C_{2-10}$-alkenyl, $C_{2-10}$-alkynyl, $C_{3-10}$-cycloalkyl and $C_{4-10}$-cycloalkenyl optionally consisting of 1-4 heteroatoms selected from N, O and S, or $R^7$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $C_{1-8}$-alkyl, $C_{2-8}$-alkenyl, $C_{2-8}$-alkynyl, $NR^8R^9$, $OR^{10}$, $SR^{11}$, $C(O)R^{12}$, $COOR^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$;

$R^8$ and $R^9$ are each independently H, $C_{1-8}$-alkyl, $C_{3-8}$-cycloalkyl, $C_{2-8}$-alkenyl, $C_{2-8}$-alkynyl, $C_{1-8}$-alkylamino-, $C_{1-8}$-dialkylamino-, $C_{1-8}$-alkoxyl, $C_{1-8}$-thioalkyl, $C_{1-8}$-alkoxy-$C_{1-8}$-alkyl, aryl, heteroaryl, or heterocyclyl;

$R^{10}$, $R^{11}$, and $R^{16}$ are each independently H, $C_{1-8}$-alkyl, $C_{2-8}$-alkenyl, $C_{2-8}$-alkynyl, $C_{1-8}$-alkoxy-$C_{1-8}$-alkyl, $C_{3-8}$-cycloalkyl, aryl, heterocyclyl, $C_{1-8}$-alkyl-heterocyclyl or heterocyclyl-$C_{1-8}$-alkyl;

$R^{12}$, $R^{13}$, $R^{14}$ and $R^{15}$ are each independently H, $C_{1-8}$-alkyl, $C_{3-8}$-cycloalkyl, $C_{2-8}$-alkenyl, $C_{2-8}$-alkynyl, $C_{1-8}$-alkylamino-, $C_{1-8}$-dialkylamino-, $C_{1-8}$-alkoxyl, $C_{1-8}$-thioalkyl, aryl, heteroaryl, heterocyclyl or alkyl-heterocyclyl; and $R^{17}$ is halo, CN, $NO_2$, or ring selected from $C_{3-10}$-cycloalkyl, phenyl, naphthyl, pyridyl, pyrimidinyl, pyridazinyl, triazinyl, piperidinyl, piperazinyl, pyrrolyl, imidazolyl, pyrazolyl, triazolyl, pyrrolidinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, phthalazinyl, morpholinyl, thiophenyl, furyl, dihydrofuryl, tetrahydrofuryl, thiazolyl, oxazolyl, isoxazolyl, isothiazolyl, indolyl, isoindolyl, indolinyl, benzofuranyl, dihydrobenzofuranyl, benzothiophenyl, benzimidazolyl, benzoxazolyl, benzisoxazolyl and benzothiazolyl, each ring of which is optionally substituted independently with 1-3 substituents of halo, haloalkyl, CN, $NO_2$, $NH_2$, OH, $C_{1-8}$-alkyl, $C_{2-8}$-alkenyl, $C_{2-8}$-alkynyl, $C_{1-8}$-alkylamino-, $C_{1-8}$-alkoxyl or $C_{1-8}$-thioalkyl.

23. The compound of claim 22 or a stereomer, a tautomer, or a pharmaceutically acceptable salt thereof, wherein $R^1$ is hydrogen; and $R^2$ is phenyl, naphthyl, pyridyl, pyrimidinyl, pyridazinyl, triazinyl, pyrrolyl, imidazolyl, pyrazolyl, triazolyl, quinolinyl, isoquinolinyl, quinazolinyl, isoquinazolinyl, phthalazinyl, thiophenyl, furyl, thiazolyl, oxazolyl, isoxazolyl, isothiazolyl, indolyl, isoindolyl, indolinyl, benzofuranyl, benzothiophenyl, benzimidazolyl, benzoxazolyl, benzisoxazolyl or benzothiazolyl, each of which is optionally substituted independently with 1-3 substituents of $R^7$, $NR^8R^9$, $OR^{10}$, $SR^{11}$, $COOR^{12}$, $C(O)R^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{14}S(O)_2R^{16}$.

24. The compound of claim 22 or a stereomer, a tautomer, or a pharmaceutically acceptable salt thereof, wherein $R^4$ is hydrogen; and $R^5$ is phenyl, naphthyl, pyridyl, pyrimidinyl, pyridazinyl, triazinyl, pyrrolyl, imidazolyl, pyrazolyl, triazolyl, quinolinyl, isoquinolinyl, quinazolinyl, isoquinazolinyl, phthalazinyl, thiophenyl, furyl, thiazolyl, oxazolyl, isoxazolyl, isothiazolyl, indolyl, isoindolyl, indolinyl, benzofuranyl, benzothiophenyl, benzimidazolyl, benzoxazolyl, benzisoxazolyl or benzothiazolyl, each of which is optionally substituted independently with 1-3 substituents of $R^7$, $NR^8R^9$, $OR^{10}$, $SR^{11}$, $COOR^{12}$, $C(O)R^{13}$, $C(O)NR^8R^9$, $NR^{14}C(O)R^{15}$, $NR^{14}C(O)NR^8R^9$, $OC(O)NR^8R^9$, $S(O)_2R^{16}$, $S(O)_2NR^8R^9$ or $NR^{17}S(O)_2R^{16}$.

25. The compound of claim 22 or a stereomer, a tautomer, or a pharmaceutically acceptable salt thereof, wherein $R^3$ is optionally substituted alkyl or optionally substituted alkenyl.

26. A compound and pharmaceutically acceptable salts thereof selected from the group consisting of:

1-(but-3-enyl)-$N^3$-(2,6-dimethylphenyl)-$N^6$-phenyl-1H-pyrazolo[3,4-d]pyrimidine-3,6-diamine;

4-(3-(2,6-dimethylphenylamino)-6-(phenylamino)-1H-pyrazolo[3,4-d]pyrimidin-1-yl)butane-1,2-diol;

1-(2-(1,3-dioxolan-4-yl)ethyl)-N3-(2,6-dimethylphenyl)-N6-phenyl-1H-pyrazolo[3,4-d]pyrimidine-3,6-diamine;

3-(3-(2,6-dimethylphenylamino)-6-(phenylamino)-1H-pyrazolo[3,4-d]pyrimidin-1-yl)propan-1-ol;

1-(3-(dimethylamino)propyl)-N3-(2,6-dimethylphenyl)-N6-phenyl-1H-pyrazolo[3,4-d]pyrimidine-3,6-diamine;

$N^3$-(2,6-dimethylphenyl)-1-(3-(methylamino)propyl)-$N^6$-phenyl-1H-pyrazolo[3,4-d]pyrimidine-3,6-diamine;

1-(3-(diethylamino)propyl)-$N^3$-(2,6-dimethylphenyl)-$N^6$-phenyl-1H-pyrazolo[3,4-d]pyrimidine-3,6-diamine;

$N^3$-(2,6-dimethylphenyl)-$N^6$-phenyl-1-(3-(pyrrolidin-1-yl)propyl)-1H-pyrazolo[3,4-d]pyrimidine-3,6-diamine;

1-(dimethylamino)-4-(3-(2,6-dimethylphenylamino)-6-(phenylamino)-1H-pyrazolo[3,4-d]pyrimidin-1-yl)butan-2-ol;

4-(3-(2,6-dimethylphenylamino)-6-(phenylamino)-1H-pyrazolo[3,4-d]pyrimidin-1-yl)-1-(pyrrolidin-1-yl)butan-2-ol;

4-(3-(2,6-dimethylphenylamino)-6-(phenylamino)-1H-pyrazolo[3,4-d]pyrimidin-1-yl)butan-2-ol;

$N^3$-(2,6-dimethyl-phenyl)-$N^6$-phenyl-1-(3-piperidin-1-yl-propyl)-1H-pyrazolo[3,4-d]pyrimidine-3,6-diamine;

$N^3$-(2,6-dimethyl-phenyl)-$N^6$-(4-piperazin-1-yl-phenyl)-1-(3-piperidin-1-yl-propyl)-1H-pyrazolo[3,4-d]pyrimidine-3,6-diamine;

$N^3$-(2,6-dimethyl-phenyl)-$N^6$-[4-(4-methyl-piperazin-1-yl)-phenyl]-1-(3-piperidin-1-yl-propyl)-1H-pyrazolo[3,4-d]pyrimidine-3,6-diamine;

$N^3$-(2,6-dimethyl-phenyl)-1-(2-morpholin-4-yl-ethyl)-$N^6$-phenyl-1H-pyrazolo[3,4-d]pyrimidine-3,6-diamine;

$N^3$-(2,6-dimethyl-phenyl)-$N^6$-[4-(2-methoxy-ethoxy)-phenyl]-1-(2-morpholin-4-yl-ethyl)-1H-pyrazolo[3,4-d]pyrimidine-3,6-diamine;

$N^3$-(2,6-dimethyl-phenyl)-$N^6$-[4-(4-methyl-piperazin-1-yl)-phenyl]-1-(2-morpholin-4-yl-ethyl)-1H-pyrazolo[3,4-d]pyrimidine-3,6-diamine;

$N^3$-(2,6-dimethyl-phenyl)-$N^6$-[4-(2-methoxy-ethoxy)-phenyl]-1-(3-methoxy-3-methyl-butyl)-1H-pyrazolo[3,4-d]pyrimidine-3,6-diamine;

$N^3$-(2,6-dimethyl-phenyl)-1-(3-methoxy-3-methyl-butyl)-$N^6$-[4-(methylpiperazin-1-yl)phenyl]-1H-pyrazolo[3,4-d]pyrimidine-3,6-diamine;

$N^3$-(2,6-dimethyl-phenyl)-1-(3-methoxy-3-methylbutyl)-$N^6$-(4-piperazin-1-yl-phenyl)-1H-pyrazolo[3,4-d]pyrimidine-3,6-diamine;

$N^3$-(2,6-dimethylphenyl)-$N^6$-[3-fluoro-4-(3-(piperidin-1-yl)propoxy)phenyl]-1-(3-methoxy-3-methylbutyl)-1H-pyrazolo[3,4-d]pyrimidine-3,6-diamine;

1-(3-methoxy-3-methyl-butyl)-$N^3$—$N^6$-diphenyl-1H-pyrazolo[3,4-d]pyrimidine-3,6-diamine;

1-(3-methoxy-3-methyl-butyl)-$N^6$-[4-(4-methyl-piperazin-1-yl)-phenyl-$N^3$-phenyl-1H-pyrazolo[3,4-d]pyrimidine-3,6-diamine;

1-(3-methoxy-3-methyl-butyl)-$N^6$-phenyl-$N^3$-(2,4,6-trimethyl-phenyl)-1H-pyrazolo[3,4-d]pyrimidine-3,6-diamine;

$N^3$-(4-fluoro-2,6-dimethyl-phenyl)-1-(3-methoxy-3-methyl-butyl)-$N^6$-phenyl-1H-pyrazolo[3,4-d]pyrimidine-3,6-diamine;

$N^3$-(4-fluoro-2,6-dimethyl-phenyl)-1-(3-methoxy-3-methyl-butyl)-$N^6$-[4-(4-methyl-piperazin-1-yl)-phenyl]-1H-pyrazolo[3,4-d]pyrimidine-3,6-diamine;

$N^3$-(2,6-dichlorophenyl)-$N^6$-(3-fluoro-4-(2-(pyrrolidin-1-yl)ethoxy)phenyl)-1-(3-methoxy-3-methylbutyl)-1H-pyrazolo[3,4-d]pyrimidine-3,6-diamine and $N^3$-(2,6-dichlorophenyl)-1-(3-methoxy-3-methylbutyl)-$N^6$-methyl-1H-pyrazolo[3,4-d]pyrimidine-3,6-diamine.

27. A pharmaceutical composition comprising a pharmaceutically acceptable carrier and a compound as set forth in claim 1 or a stereomer, a tautomer, or a pharmaceutically acceptable salt thereof.

28. A pharmaceutical composition comprising a pharmaceutically acceptable carrier and a compound as set forth in claim 2 or a stereomer, a tautomer, or a pharmaceutically acceptable salt thereof.

29. A pharmaceutical composition comprising a pharmaceutically acceptable carrier and a compound as set forth in claim 4 or a stereomer, a tautomer, or a pharmaceutically acceptable salt thereof.

30. A pharmaceutical composition comprising a pharmaceutically acceptable carrier and a compound as set forth in claim 9 or a stereomer, a tautomer, or a pharmaceutically acceptable salt thereof.

31. A pharmaceutical composition comprising a pharmaceutically acceptable carrier and a compound as set forth in claim 21 or a stereomer, a tautomer, or a pharmaceutically acceptable salt thereof.

32. A pharmaceutical composition comprising a pharmaceutically acceptable carrier and a compound as set forth in claim 22 or a stereomer, a tautomer, or a pharmaceutically acceptable salt thereof.

33. A pharmaceutical composition comprising a pharmaceutically acceptable carrier and a compound as set forth in claim 24 or a stereomer, a tautomer, or a pharmaceutically acceptable salt thereof.

34. A method of manufacturing a medicament comprising combining a pharmaceutically acceptable carrier with a compound of claim 1 or a stereomer, a tautomer, or a pharmaceutically acceptable salt thereof.

\* \* \* \* \*